(12) United States Patent
Pyle et al.

(10) Patent No.: US 12,421,257 B2
(45) Date of Patent: Sep. 23, 2025

(54) COMPOSITIONS AND METHODS FOR INHIBITING GROUP II INTRON RNA

(71) Applicant: YALE UNIVERSITY, New Haven, CT (US)

(72) Inventors: Anna Marie Pyle, New Haven, CT (US); Olga Fedorova, New Haven, CT (US); Erik Jagdmann, New Haven, CT (US); Michael Van Zandt, New Haven, CT (US); Lin Yuan, New Haven, CT (US); Albert DeBerardinis, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 18/456,819

(22) Filed: Aug. 28, 2023

(65) Prior Publication Data

US 2024/0018169 A1  Jan. 18, 2024

Related U.S. Application Data

(62) Division of application No. 16/964,621, filed as application No. PCT/US2019/015086 on Jan. 25, 2019, now Pat. No. 11,739,104.

(60) Provisional application No. 62/622,287, filed on Jan. 26, 2018.

(51) Int. Cl.

| | |
|---|---|
| C07C 233/65 | (2006.01) |
| A61P 31/10 | (2006.01) |
| C07C 49/84 | (2006.01) |
| C07C 233/73 | (2006.01) |
| C07C 243/38 | (2006.01) |
| C07D 207/08 | (2006.01) |
| C07D 211/16 | (2006.01) |
| C07D 217/04 | (2006.01) |
| C07D 233/64 | (2006.01) |
| C07D 239/26 | (2006.01) |
| C07D 277/24 | (2006.01) |
| C07D 277/26 | (2006.01) |
| C07D 277/66 | (2006.01) |
| C07D 295/192 | (2006.01) |
| C07D 295/215 | (2006.01) |
| C07D 307/52 | (2006.01) |
| C07D 307/80 | (2006.01) |
| C07D 307/83 | (2006.01) |
| C07D 405/04 | (2006.01) |
| C07D 405/12 | (2006.01) |
| C07D 413/04 | (2006.01) |
| C07F 5/02 | (2006.01) |

(52) U.S. Cl.
CPC .............. *C07F 5/027* (2013.01); *A61P 31/10* (2018.01); *C07C 49/84* (2013.01); *C07C 233/65* (2013.01); *C07C 233/73* (2013.01); *C07C 243/38* (2013.01); *C07D 207/08* (2013.01); *C07D 211/16* (2013.01); *C07D 217/04* (2013.01); *C07D 233/64* (2013.01); *C07D 239/26* (2013.01); *C07D 277/24* (2013.01); *C07D 277/26* (2013.01); *C07D 277/66* (2013.01); *C07D 295/192* (2013.01); *C07D 295/215* (2013.01); *C07D 307/52* (2013.01); *C07D 307/80* (2013.01); *C07D 307/83* (2013.01); *C07D 405/04* (2013.01); *C07D 405/12* (2013.01); *C07D 413/04* (2013.01)

(58) Field of Classification Search
CPC .... C07C 233/65; C07C 233/73; C07C 243/38
See application file for complete search history.

(56) References Cited

U.S. PATENT DOCUMENTS

| | | | |
|---|---|---|---|
| 5,900,406 A | 5/1999 | Von et al. | |
| 9,731,001 B2 | 8/2017 | Gilbert et al. | |
| 2011/0189306 A1* | 8/2011 | Kartner | A61K 31/59 424/676 |
| 2012/0022121 A1 | 1/2012 | Dalton et al. | |

OTHER PUBLICATIONS

Ilango et al. Trop. J. Pharm. Res., Apr. 2011, 10(2), 219-229 (Year: 2011).*
Hu et al. RSC Adv. 2017, 7, 29697-29701 (Year: 2017).*
CAS Registry No. 664311-01-7, which entered STN on Mar. 18, 2004 (Year: 2004).*
CAS Registry No. 544659-64-5, which entered STN on Jul. 9, 2003 (Year: 2003).*
Tavis et al. PLoS Pathogens 2013, 9, e1003125 (Year: 2013).*
CAS Registry No. 1266127-15-4, which entered STN on Mar. 3, 2011 (Year: 2011).*
CAS Registry No. 549518-60-7, which entered STN on Jul. 17, 2003 (Year: 2003).*
Carcelli et al. Nature: Scientific Reports, 2016, 6, 31500 (Year: 2016).*

(Continued)

*Primary Examiner* — Matthew P Coughlin

(74) *Attorney, Agent, or Firm* — Saul Ewing LLP; Domingos Silva

(57) ABSTRACT

The present invention provides compositions and methods for inhibiting group II intron splicing for treating or preventing a disease or disorder associated with an organism harboring an active group II intron. The present invention also provides compositions and methods for inhibiting group II intron splicing for inhibiting, preventing or reducing growth of an organism harboring an active group II intron.

5 Claims, 21 Drawing Sheets

Specification includes a Sequence Listing.

(56) References Cited

OTHER PUBLICATIONS

International Search Report and Written Opinion for PCT International Application No. PCT/US2019/015086 issued Jun. 10, 2019.
Bernat, et al., "RNA structures as mediators of neurological diseases and as drug targets", Neuron. 87(1), Jul. 2015, 28-46.
Disney, "Rational design of chemical genetic probes of RNA function and lead therapeutics targeting repeating transcripts", Drug Discov Today. 18(23-24), Dec. 2013, 1228-1236.
Miletti, et al., "Pentamidine inhibition of group I intron splicing in Candida albicans correlates with growth inhibition", Antimicrob Agents Chemother. 44(4), Apr. 2000, 958-966.
Zhao, et al., "Structural Insights into the Mechanism of Group II Intron Splicing", Trends Biochem Sci. 42(6), Jun. 2017, 470-482.
Sato et al. Plant Science 2001, 160, 229-236 (Year: 2001).
Aswathanarayanappa et al. Med Chem Res 2013, 22, 78-87 (Year: 2013).
Romagnoli et al. Bioorg. Med. Chem. 2009, 17, 6862-6871 (Year: 2009).
Schenck et al. Tetrahedron Letters 1968, 19, 2379-2381 (Year: 1968).
Bose et al. Tetrahedron Letters 2001, 42, 8907-8909 (Year: 2001).

\* cited by examiner

SEQ ID NO:9
SEQ ID NO:10

Substrate: 5' CGU GGU GGG ACA UUU (X) CGA (BHQ-2)
Non-hydrolyzable substrate: 5' CGU GGU GGG ACA UUU (X) (CH₂)₁₂ (BHQ-2)

(X) = aminomodifier C6dT, labeled post-synthetically with Alexa Fluor 555
(BHQ-2) = Black Hole Quencher 2

S. cerevisiae (ai5Y)  SEQ ID NO:11
C. parapsilosis  SEQ ID NO:12

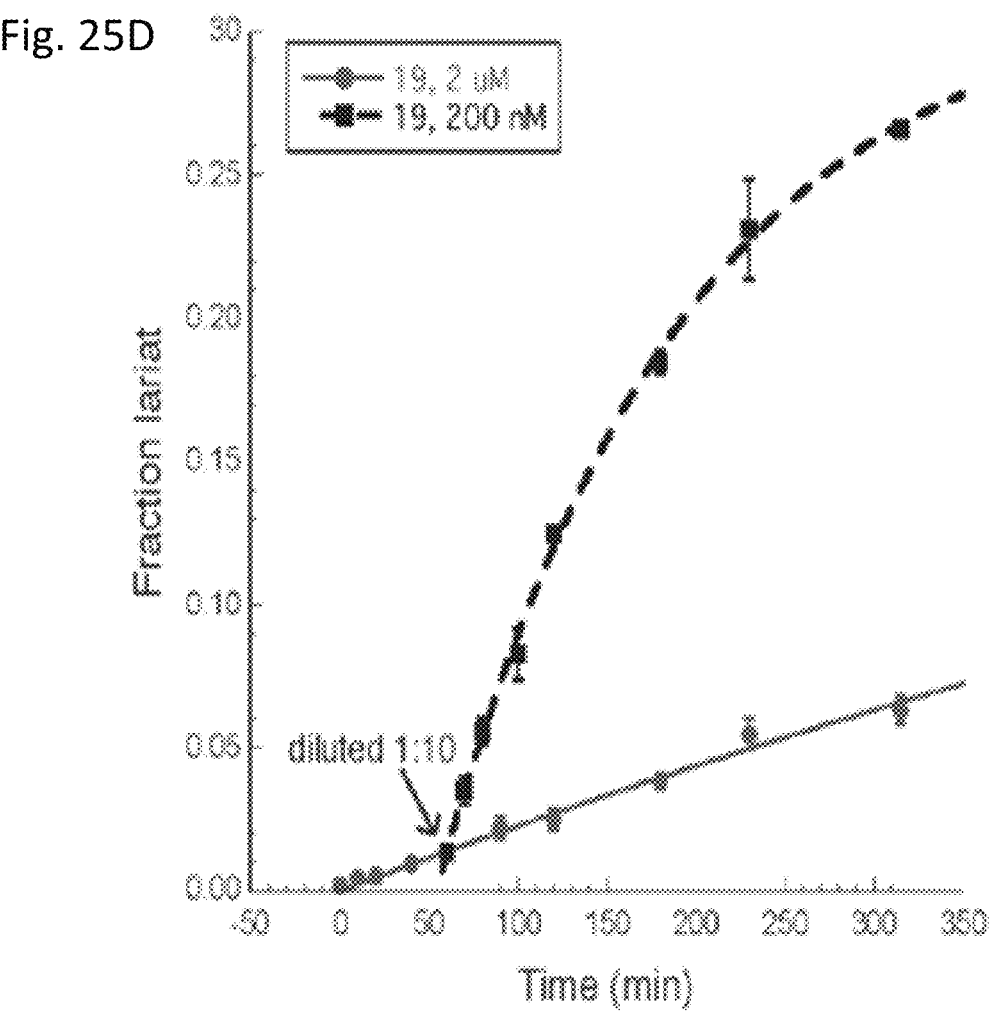

SEQUENCE LISTING

```
Sequence total quantity: 19
SEQ ID NO: 1              moltype = DNA   length = 21
FEATURE                   Location/Qualifiers
misc_feature              1..21
                          note = Chemically Synthesized
source                    1..21
                          mol_type = other DNA
                          organism = synthetic construct
SEQUENCE: 1
tcgaacaaga aatgcaaacc g                                                21
```

```
SEQ ID NO: 2               moltype = DNA  length = 21
FEATURE                    Location/Qualifiers
misc_feature               1..21
                           note = Chemically Synthesized
source                     1..21
                           mol_type = other DNA
                           organism = synthetic construct
SEQUENCE: 2
ggcagattcc aaacccaaaa c                                           21

SEQ ID NO: 3               moltype = DNA  length = 20
FEATURE                    Location/Qualifiers
misc_feature               1..20
                           note = Chemically Synthesized
source                     1..20
                           mol_type = other DNA
                           organism = synthetic construct
SEQUENCE: 3
tgtcttggct tctcacttgg                                             20

SEQ ID NO: 4               moltype = DNA  length = 20
FEATURE                    Location/Qualifiers
misc_feature               1..20
                           note = Chemically Synthesized
source                     1..20
                           mol_type = other DNA
                           organism = synthetic construct
SEQUENCE: 4
ttcaacttct ggaccgacac                                             20

SEQ ID NO: 5               moltype = DNA  length = 23
FEATURE                    Location/Qualifiers
misc_feature               1..23
                           note = Chemically Synthesized
source                     1..23
                           mol_type = other DNA
                           organism = synthetic construct
SEQUENCE: 5
tggtatgcct agaagaattc ctg                                         23

SEQ ID NO: 6               moltype = DNA  length = 30
FEATURE                    Location/Qualifiers
misc_feature               1..30
                           note = Chemically Synthesized
source                     1..30
                           mol_type = other DNA
                           organism = synthetic construct
SEQUENCE: 6
agaataatga taatagtgca atgaatgaac                                  30

SEQ ID NO: 7               moltype = DNA  length = 21
FEATURE                    Location/Qualifiers
misc_feature               1..21
                           note = Chemically Synthesized
source                     1..21
                           mol_type = other DNA
                           organism = synthetic construct
SEQUENCE: 7
cttactacgt ggtgggacat t                                           21

SEQ ID NO: 8               moltype = DNA  length = 26
FEATURE                    Location/Qualifiers
misc_feature               1..26
                           note = Chemically Synthesized
source                     1..26
                           mol_type = other DNA
                           organism = synthetic construct
SEQUENCE: 8
gtcattacag cttagcatat ttatgt                                      26

SEQ ID NO: 9               moltype = RNA  length = 19
FEATURE                    Location/Qualifiers
misc_feature               1..19
                           note = Chemically Synthesized
misc_feature               16
                           note = aminomodifier C6dT nucleotide
source                     1..19
                           mol_type = other RNA
```

```
                           organism = synthetic construct
SEQUENCE: 9
cgtggtggga catttncga                                                    19

SEQ ID NO: 10              moltype = RNA   length = 16
FEATURE                    Location/Qualifiers
misc_feature               1..16
                           note = Chemically Synthesized
misc_feature               16
                           note = aminomodifier C6dT nucleotide
source                     1..16
                           mol_type = other RNA
                           organism = synthetic construct
SEQUENCE: 10
cgtggtggga catttn                                                       16

SEQ ID NO: 11              moltype = DNA   length = 34
FEATURE                    Location/Qualifiers
misc_feature               1..34
                           note = Chemically Synthesized
source                     1..34
                           mol_type = other DNA
                           organism = synthetic construct
SEQUENCE: 11
gagccgtatg cgatgaaagt cgcacgtacg gttc                                   34

SEQ ID NO: 12              moltype = DNA   length = 34
FEATURE                    Location/Qualifiers
misc_feature               1..34
                           note = Chemically Synthesized
source                     1..34
                           mol_type = other DNA
                           organism = synthetic construct
SEQUENCE: 12
gagccgtatg cagggtgact tgcacgtacg gttc                                   34

SEQ ID NO: 13              moltype = DNA   length = 20
FEATURE                    Location/Qualifiers
misc_feature               1..20
                           note = Chemically Synthesized
source                     1..20
                           mol_type = other DNA
                           organism = synthetic construct
SEQUENCE: 13
tggatgggtc ttgattgtgg                                                   20

SEQ ID NO: 14              moltype = DNA   length = 21
FEATURE                    Location/Qualifiers
misc_feature               1..21
                           note = Chemically Synthesized
source                     1..21
                           mol_type = other DNA
                           organism = synthetic construct
SEQUENCE: 14
gtcaaattca aagacacccg g                                                 21

SEQ ID NO: 15              moltype = DNA   length = 22
FEATURE                    Location/Qualifiers
misc_feature               1..22
                           note = Chemically Synthesized
source                     1..22
                           mol_type = other DNA
                           organism = synthetic construct
SEQUENCE: 15
ggtgctgtag atatggcatt tg                                                22

SEQ ID NO: 16              moltype = DNA   length = 24
FEATURE                    Location/Qualifiers
misc_feature               1..24
                           note = Chemically Synthesized
source                     1..24
                           mol_type = other DNA
                           organism = synthetic construct
SEQUENCE: 16
gcactaattg atgatagtgg agga                                              24

SEQ ID NO: 17              moltype = DNA   length = 22
FEATURE                    Location/Qualifiers
misc_feature               1..22
```

```
                      note = Chemically Synthesized
source                1..22
                      mol_type = other DNA
                      organism = synthetic construct
SEQUENCE: 17
tgttcttgtt actggtcatg ct                                          22

SEQ ID NO: 18         moltype = DNA  length = 23
FEATURE               Location/Qualifiers
misc_feature          1..23
                      note = Chemically Synthesized
source                1..23
                      mol_type = other DNA
                      organism = synthetic construct
SEQUENCE: 18
agcacttact aactgttcac gtc                                         23

SEQ ID NO: 19         moltype = RNA  length = 30
FEATURE               Location/Qualifiers
misc_feature          1..30
                      note = Chemically Synthesized
source                1..30
                      mol_type = other RNA
                      organism = synthetic construct
SEQUENCE: 19
agcagttccc ctgcataagg atgaaccgct                                  30
```

COMPOSITIONS AND METHODS FOR INHIBITING GROUP II INTRON RNA

CROSS REFERENCE TO RELATED APPLICATIONS

This application is a divisional of, and claims priority to, U.S. Application No. patent application Ser. No. 16/964,621 filed Jul. 24, 2020, now allowed, which is a 35 U.S.C. § 371 national phase application from, and claims priority to, International Application No. PCT/US2019/015086, filed Jan. 25, 2019, and published under PCT Article 21(2) in English, which claims priority under 35 U.S.C. § 119(e) to U.S. Provisional Application No. 62/622,287, filed Jan. 26, 2018, all of which applications are incorporated herein by reference in their entireties.

STATEMENT REGARDING FEDERALLY SPONSORED RESEARCH OR DEVELOPMENT

This invention was made with government support under AI115951 and GM050313 awarded by National Institutes of Health. The government has certain rights in the invention.

SEQUENCE LISTING

This disclosure contains one or more sequences in a computer readable format in an accompanying .xml file entitled "047162-7290US2_Seq Listing.XML", which is 25.3 KBytes in size and was created on Aug. 22, 2023, the contents of which are incorporated herein by reference in their entirety.

BACKGROUND OF THE INVENTION

It is becoming increasingly clear that large, highly structured RNA molecules are essential for most metabolic functions. There has been corresponding interest in developing small molecules that target specific RNA structures and thereby modulate gene expression for the treatment of various diseases. Previous studies on bacterial riboswitches have demonstrated that folded RNA molecules can contain high affinity pockets for the binding of small molecules such as metabolites, and these ligands have been optimized in efforts to develop new antibiotics (Blount and Breaker, 2006, Nat Biotechnol, 24:1558-1564). Indeed, antibacterial compounds have long been known to target ribosomal RNA (Wallis and Schroeder, 1997, Prog Biophys Mol Biol, 67:141-154; Schroeder et al., 2000, EMBO J, 19:1-9) and, given availability of high resolution structural data, these have been the subject of continuing optimization (Wilson, 2009, Crit Rev Biochem Mol Biol, 44:393-433; Wilson, 2014, Nature reviews. Microbiology, 12:35-48; Blaha et al., 2012, Current opinion in structural biology, 22:750-758). While these studies provide important precedents, they were conducted on RNA molecules that were already known to bind classes of small molecules. De-novo RNA targeting efforts have been limited, and they have focused primarily on small molecules that bind RNA secondary structural elements, such as RNA hairpins from triplet repeat diseases and stem-loops in viral RNA genomes (Bernat and Disney, 2015, Neuron, 87:28-46; Disney, 2013, Drug discovery today, 18:1228-1236). Thus far, RNA tertiary structures have not been successfully targeted de-novo using high throughput screening and lead optimization techniques that are typical of medicinal chemistry programs for the development of protein inhibitors. With the exception of bacterial riboswitch inhibitors, there are no new classes of antimicrobial compounds that have been developed to target RNA, and none that are designed to target eukaryotic pathogens.

Diseases involving pathogenic yeasts have become an increasing threat, particularly for recipients of implanted devices, for neonatal patients, cancer patients and others with compromised immune systems (Kett et al., 2011, Crit Care Med, 39:665-670). Specifically, there has been a marked increase in pathologies associated with non-albican strains, particularly *Candida parapsdosis* (Guinea, 2014, Clin Microbiol Infect, 20 Suppl 6:5-10). The most common treatment for critically ill patients with candidaemia is Amphotericin B (AmpB), which is extremely toxic, causing numerous adverse effects. Azole derivatives and echinocandins have been developed as alternatives to AmpB, but their use has been complicated by rapid resistance to *Candida* strains (Jensen et al., 2015, Antimicrobial agents and chemotherapy, 60:1500-1508; Arendrup and Perlin, 2014, Curr Opin Infect Dis, 27:484-492). The availability of potent antifungals that lack toxicity in mammals is therefore a major unmet medical need, and of value for industrial and agricultural applications. Importantly, the development of new antifungals is challenging because, as eukaryotes, fungi and yeast cells share enzymes and biochemical pathways that are structurally and functionally similar to those of humans. However, fungal RNA metabolism differs significantly, thereby providing a potential route toward new therapeutics.

Thus, there is a need in the art for compositions and methods for targeting specific RNA structures for inhibiting and preventing the growth of organisms that harbor RNA capable of forming the target structure. The present invention satisfies this need.

BRIEF SUMMARY OF THE INVENTION

In one embodiment, the invention relates to a composition comprising an inhibitor of group II intron splicing.

In one embodiment, the inhibitor of group II intron splicing is at least one selected from the group consisting of a protein, a peptide, a peptidomimetic, an antibody, a ribozyme, a small molecule chemical compound, a nucleic acid, an aptamer, a modified nucleic acid, a vector, a genome editing system and an antisense nucleic acid molecule.

In one embodiment, the inhibitor of group II intron splicing is a small molecule chemical compound.

In one embodiment, the inhibitor of group II intron splicing is a small molecule chemical compound of Formula (I) or a salt thereof;

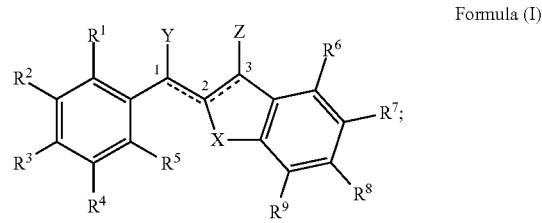

Formula (I)

wherein in Formula (I):
X is O, S, or NR$^{10}$;
R$^1$, R$^2$, R$^3$, R$^4$, R$^5$, R$^6$, R$^7$, R$^8$, R$^9$, and R$^{10}$ are each independently selected from the group consisting of H, —C$_1$-C$_6$ alkyl, —C$_1$-C$_6$ fluoroalkyl, —C$_1$-C$_6$ heteroalkyl, aryl, heteroaryl, cycloalkyl, heterocycloalkyl, F, Cl, Br, I, —CN, —NO₂, —OH, —OR¹¹, —SR¹¹, —S(=O)R¹¹, —S(=O)₂R¹¹, —NHS(=O)₂R¹¹, —C(=O)R¹¹, —OC(=O)R¹¹, —CO₂R¹¹, —OCO₂R¹¹, —CH(R¹¹)₂, —N(R¹¹)₂, —C(=O)N(R¹¹)₂, —C(=O)NHR¹¹, —OC(=O)N(R¹¹)₂, —NHC(=O)NH(R¹¹), —NHC(=O)R¹¹, —NHC(=O)OR¹¹, —C(OH)(R¹¹)₂, and —C(NH₂)(R¹¹)₂, and combinations thereof;

or optionally two adjacent R¹-R⁵ or R⁶-R⁹ are joined to form a ring;

each occurrence of R¹¹ is independently selected from the group consisting of H, —C₁-C₆ alkyl, —C₁-C₆ fluoroalkyl, —C₁-C₆ heteroalkyl, aryl, heteroaryl, cycloalkyl, heterocycloalkyl, F, Cl, Br, I, —CN, —NO₂, —OH, and combinations thereof; and wherein only one of the two following conditions is met:
condition 1, wherein the bond between carbons 1 and 2 is a single bond, the bond between carbons 2 and 3 is a double bond, Y is (=O), and Z is H; or
condition 2, wherein the bond between carbons 1 and 2 is a double bond, the bond between carbons 2 and 3 is a single bond, Y is H, and Z is (=O).

In one embodiment, the small molecule chemical compound of Formula (I) is a compound of Formula (II);

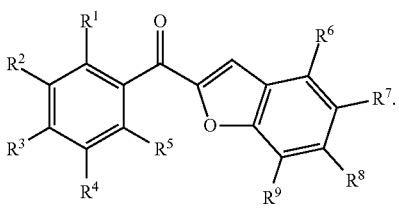

Formula (II)

In one embodiment, the small molecule chemical compound of Formula (I) is a compound of Formula (III);

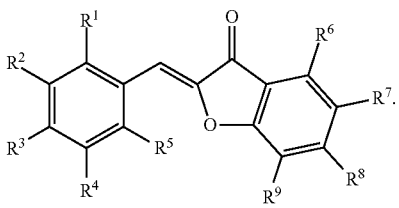

Formula (III)

In one embodiment, R², R³, and R⁴ are OH. In one embodiment, R⁷ is represented by Formula (IV):

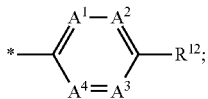

Formula (IV)

wherein in Formula (IV):
* represents the attachment to Formula (I);
A¹, A², A³, and A⁴ are CR¹³ or N;
R¹² is selected from the group consisting of H, C₁-C₆ alkyl, C₁-C₆ fluoroalkyl, C₁-C₆ perfluoroalkyl, C₁-C₆ heteroalkyl, aryl, heteroaryl, cycloalkyl, heterocycloalkyl, F, Cl, Br, I, —CN, —NO₂, —OH, —OR¹⁴, —SR¹⁴, —S(=O)R¹⁴, —S(=O)₂R¹⁴, —S(=O)₂NHR¹⁴, —S(=O)₂N(R¹⁴)₂, —NHS(=O)₂R¹⁴, —C(=O)R¹⁴, —OC(=O)R¹⁴, —CO₂R¹⁴, —OCO₂R¹⁴, —CH(R¹⁴)₂, —N(R¹⁴)₂, —C(=O)N(R¹⁴)₂, —C(=O)NHR¹⁴, —OC(=O)N(R¹⁴)₂, —NHC(=O)NH(R¹⁴), —NHC(=O)R¹⁴, —NHC(=O)OR¹⁴, —C(OH)(R¹⁴)₂, and —C(NH₂)(R¹⁴)₂, and combinations thereof;

each occurrence of R¹³ is independently selected from the group consisting of H, C₁-C₆ alkyl, F, Cl, Br, I, —CN, —NO₂, —OH, —CF₃, C₁-C₆ heteroalkyl, aryl-(C₁-C₃) alkyl, and cycloalkyl; or optionally two adjacent R¹³ are joined to form a ring;

each occurrence of R¹⁴ is independently selected from the group consisting of H, C₁-C₆ alkyl, F, Cl, Br, I, —CN, —NO₂, —OH, —CF₃, C₁-C₆ heteroalkyl, aryl-(C₁-C₃) alkyl, and cycloalkyl;

or optionally two R¹⁴ on the same atom may together form a ring.

In one embodiment, R⁸ is —C(=O)NHR¹⁰.

In one embodiment, the compound of Formula (I) is selected one of:

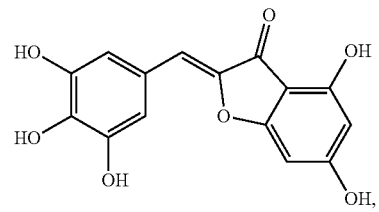

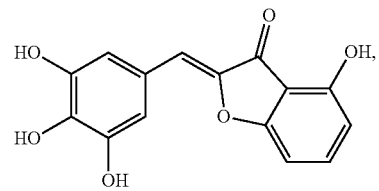

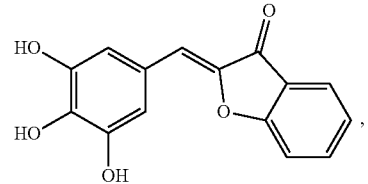

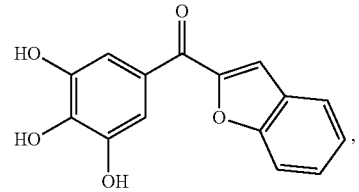

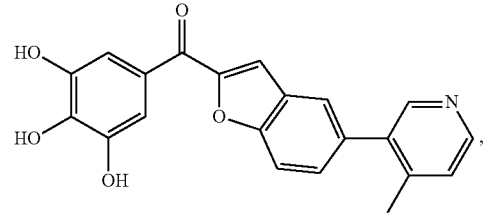

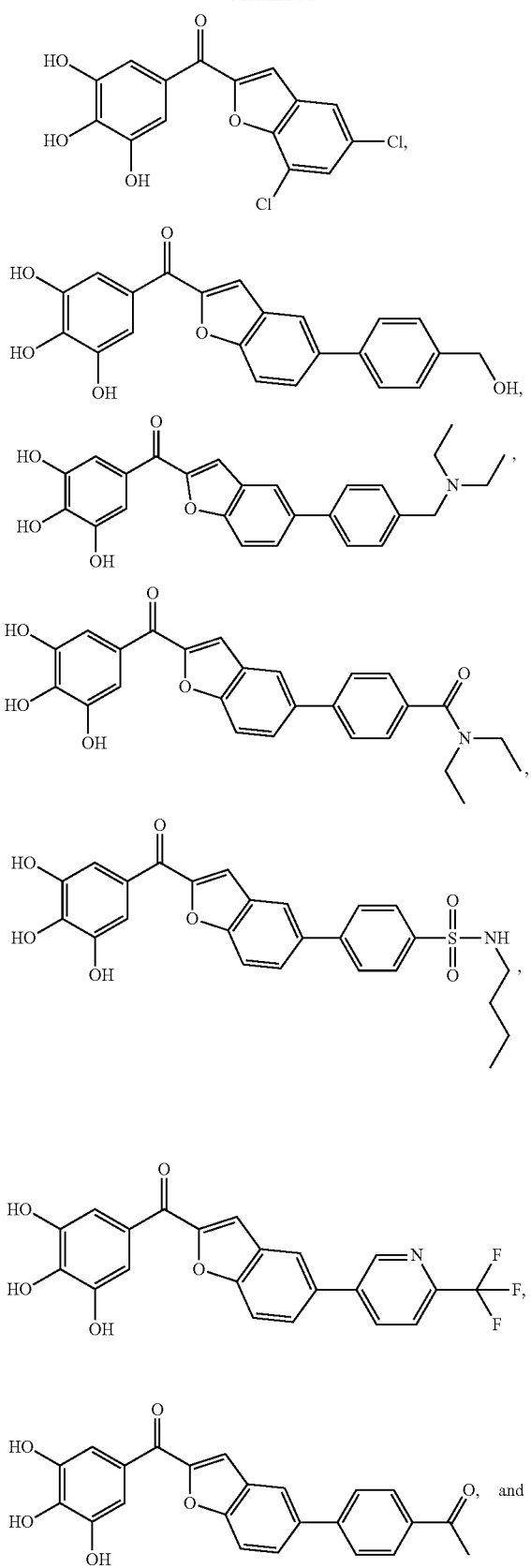

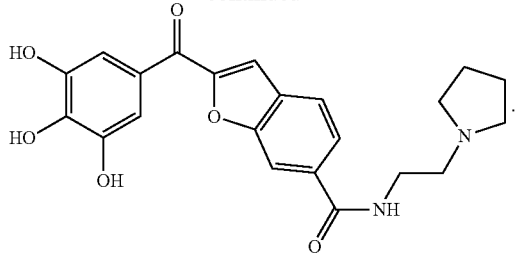

In one embodiment, the inhibitor of group II intron splicing is a small molecule chemical compound of Formula (V) or a salt thereof;

Formula (V)

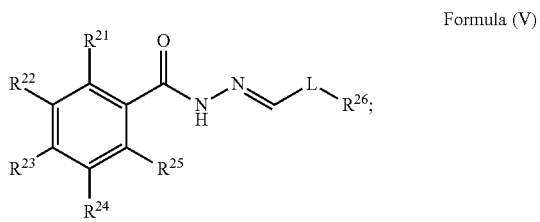

wherein in Formula (V):
L is a divalent linking group selected from the group consisting of a single bond and ethylene;
$R^{21}$, $R^{22}$, $R^{23}$, $R^{24}$, and $R^{25}$ are each independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$OR^{27}$, —$SR^{27}$, —S(=O)$R^{27}$, —S(=O)$_2R^{27}$, —NHS(=O)$_2R^{27}$, —C(=O)$R^{27}$, —OC(=O)$R^{27}$, —$CO_2R^{27}$, —$OCO_2R^{27}$, —CH($R^{27}$)$_2$, —N($R^{27}$)$_2$, —C(=O)N($R^{27}$)$_2$, —C(=O)NH$R^{27}$, —OC(=O)N($R^{27}$)$_2$, —NHC(=O)NH($R^{27}$), —NHC(=O)$R^{27}$, —NHC(=O)O$R^{27}$, —C(OH)($R^{27}$)$_2$, and —C($NH_2$)($R^{27}$)$_2$, and combinations thereof;
or optionally two adjacent $R^{21}$-$R^{25}$ are joined to form a ring;
each occurrence of $R^{27}$ is independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, and combinations thereof; and
$R^{26}$ is selected from the group consisting of an aryl group and a heteroaryl group, wherein the aryl or heteroaryl group may be optionally substituted. In one embodiment, the $R^{22}$, $R^{23}$, and $R^{24}$ are OH. In one embodiment, $R^{26}$ is a group of Formula (VI):

Formula (VI)

wherein in Formula (VI):
* represents the attachment to Formula (V);
$Z^1$, $Z^2$, $Z^3$, $Z^4$, and $Z^5$ are $CR^{28}$ or N;
each occurrence of $R^{28}$ is independently selected from the group consisting of H, $C_1$-$C_6$ alkyl, F, Cl, Br, I, —CN, —$NO_2$, —OH, —$CF_3$, —$OR^{29}$, —N($R^{29}$)$_2$, —C(=O)

$R^{29}$, $C_1$-$C_6$ heteroalkyl, aryl-($C_1$-$C_3$)alkyl, cycloalkyl, alkynyl, and combinations thereof; or optionally two adjacent $R^{28}$ are joined together to form a ring; and
$R^{29}$ is selected from the group consisting of H, $C_1$-$C_6$ alkyl, and heteroaryl-($C_1$-$C_3$)alkyl.
In one embodiment, the compound of Formula (V) is one of:
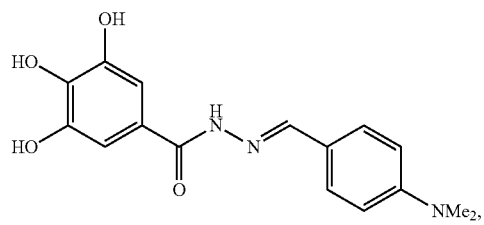
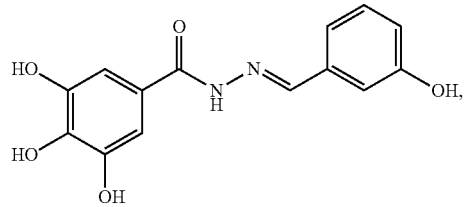
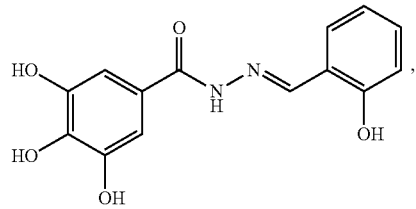
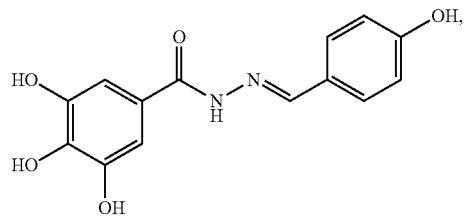
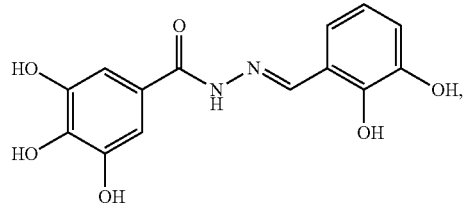
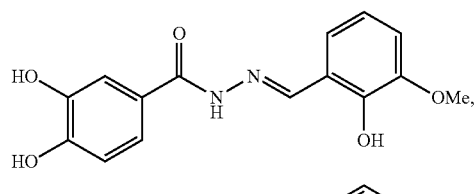
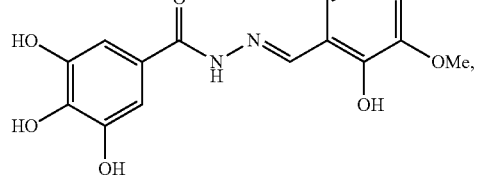
-continued
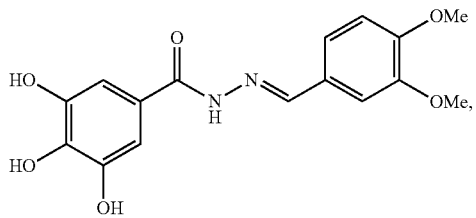
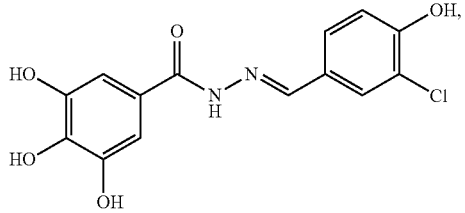
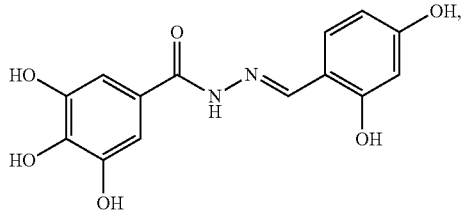
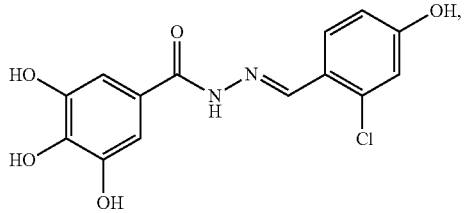
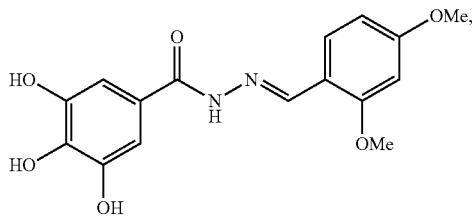
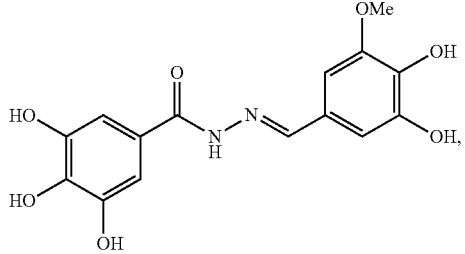
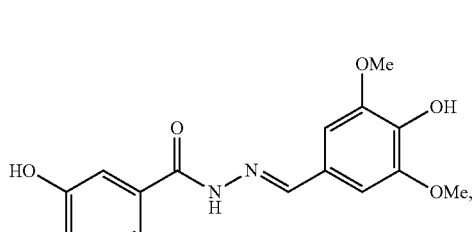

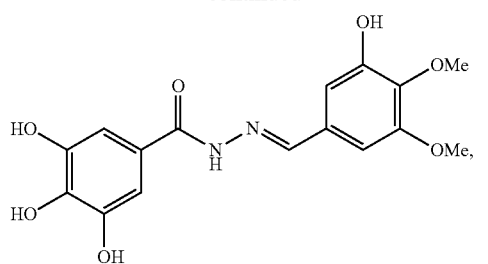

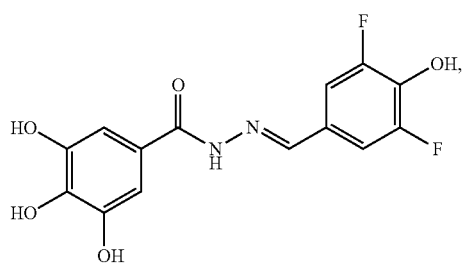

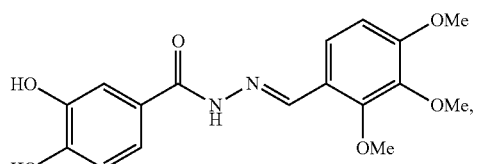

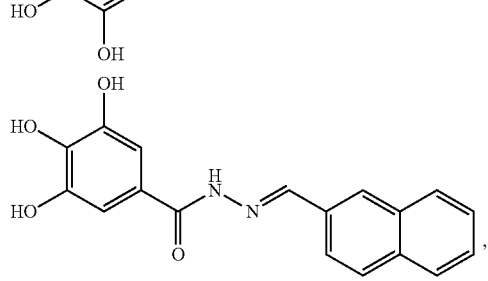

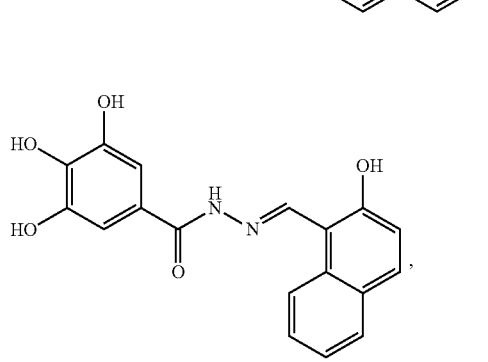

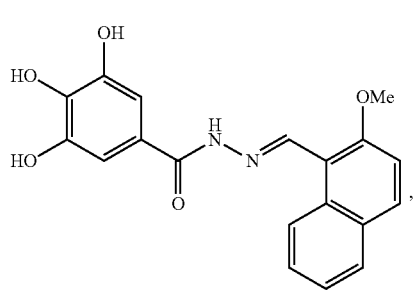

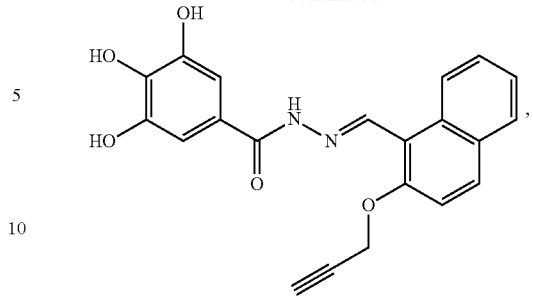

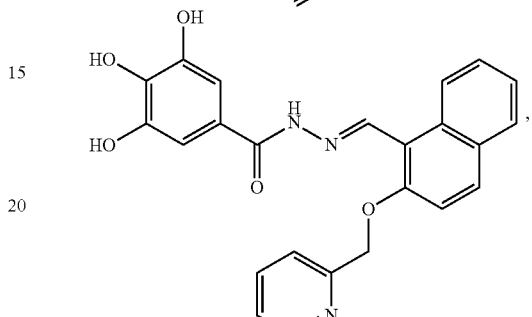

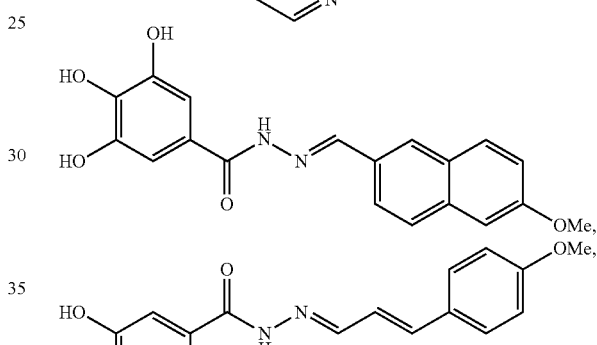

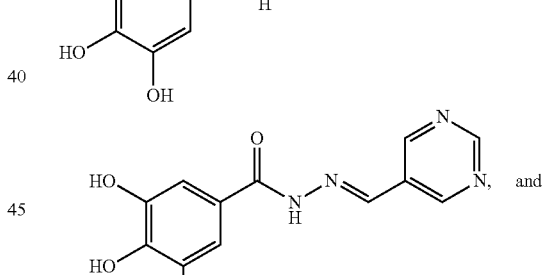

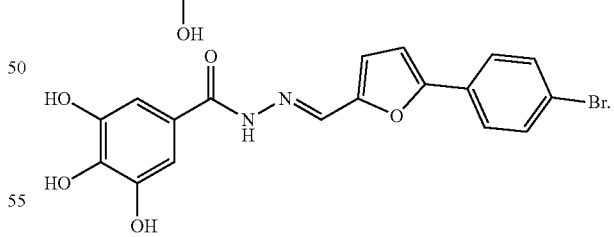

In one embodiment, the invention relates to a method of reducing or preventing growth of an organism harboring an active group II intron comprising contacting an organism harboring an active group II intron with an effective amount of an inhibitor of group II intron splicing.

In one embodiment, the inhibitor of group II intron splicing is at least one selected from the group consisting of a protein, a peptide, a peptidomimetic, an antibody, a ribozyme, a small molecule chemical compound, a nucleic acid, an aptamer, a modified nucleic acid, a vector, and an antisense nucleic acid molecule.

In one embodiment, the inhibitor of group II intron splicing is a small molecule chemical compound.

In one embodiment, the inhibitor of group II intron splicing is a small molecule chemical compound of Formula (I) or a salt thereof;

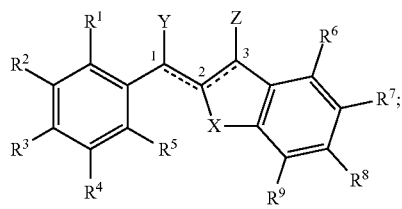

Formula (I)

wherein in Formula (I):

X is O, S, or $NR^{10}$;

$R^1$, $R^2$, $R^3$, $R^4$, $R^5$, $R^6$, $R^7$, $R^8$, $R^9$, and $R^{10}$ are each independently selected from the group consisting of H, $-C_1$-$C_6$ alkyl, $-C_1$-$C_6$ fluoroalkyl, $-C_1$-$C_6$ heteroalkyl, aryl, heteroaryl, cycloalkyl, heterocycloalkyl, F, Cl, Br, I, $-CN$, $-NO_2$, $-OH$, $-OR^{11}$, $-SR^{11}$, $-S(=O)R^{11}$, $-S(=O)_2R^{11}$, $-NHS(=O)_2R^{11}$, $-C(=O)R^{11}$, $-OC(=O)R^{11}$, $-CO_2R^{11}$, $-OCO_2R^{11}$, $-CH(R^{11})_2$, $-N(R^{11})_2$, $-C(=O)N(R^{11})_2$, $-C(=O)NHR^{11}$, $-OC(=O)N(R^{11})_2$, $-NHC(=O)NH(R^{11})$, $-NHC(=O)R^{11}$, $-NHC(=O)OR^{11}$, $-C(OH)(R^{11})_2$, and $-C(NH_2)(R^{11})_2$, and combinations thereof;

or optionally two adjacent $R^1$-$R^5$ or $R^6$-$R^9$ are joined to form a ring;

each occurrence of $R^{11}$ is independently selected from the group consisting of H, $-C_1$-$C_6$ alkyl, $-C_1$-$C_6$ fluoroalkyl, $-C_1$-$C_6$ heteroalkyl, aryl, heteroaryl, cycloalkyl, heterocycloalkyl, F, Cl, Br, I, $-CN$, $-NO_2$, $-OH$, and combinations thereof; and wherein only one of the two following conditions is met:
condition 1, wherein the bond between carbons 1 and 2 is a single bond, the bond between carbons 2 and 3 is a double bond, Y is (=O), and Z is H; or
condition 2, wherein the bond between carbons 1 and 2 is a double bond, the bond between carbons 2 and 3 is a single bond, Y is H, and Z is (=O).

In one embodiment, the inhibitor of group II intron splicing is a small molecule chemical compound of Formula (V) or a salt thereof;

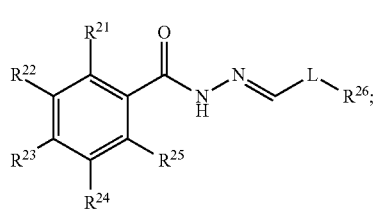

Formula (V)

wherein in Formula (V):

L is a divalent linking group selected from the group consisting of a single bond and ethylene;

$R^{21}$, $R^{22}$, $R^{23}$, $R^{24}$, and $R^{25}$ are each independently selected from the group consisting of H, $-C_1$-$C_6$ alkyl, $-C_1$-$C_6$ fluoroalkyl, $-C_1$-$C_6$ heteroalkyl, aryl, heteroaryl, cycloalkyl, heterocycloalkyl, F, Cl, Br, I, $-CN$, $-NO_2$, $-OH$, $-SR^{27}$, $-S(=O)R^{27}$, $-S(=O)_2R^{27}$, $-NHS(=O)_2R^{27}$, $-C(=O)R^{27}$, $-OC(=O)R^{27}$, $-CO_2R^{27}$, $-OCO_2R^{27}$, $-CH(R^{27})_2$, $-N(R^{27})_2$, $-C(=O)N(R^{27})_2$, $-C(=O)NHR^{27}$, $-OC(=O)N(R^{27})_2$, $-NHC(=O)NH(R^{27})$, $-NHC(=O)R^{27}$, $-NHC(=O)OR^{27}$, $-C(OH)(R^{27})_2$, and $-C(NH_2)(R^{27})_2$, and combinations thereof;

or optionally two adjacent $R^{21}$-$R^{25}$ are joined to form a ring;

each occurrence of $R^{27}$ is independently selected from the group consisting of H, $-C_1$-$C_6$ alkyl, $-C_1$-$C_6$ fluoroalkyl, $-C_1$-$C_6$ heteroalkyl, aryl, heteroaryl, cycloalkyl, heterocycloalkyl, F, Cl, Br, I, $-CN$, $-NO_2$, $-OH$, and combinations thereof; and $R^{26}$ is selected from the group consisting of an aryl group and a heteroaryl group, wherein the aryl or heteroaryl group may be optionally substituted.

In one embodiment, the invention relates to a method of inhibiting, treating or preventing a disease associated with an organism harboring an active group II intron in a subject comprising administering an effective amount of a composition comprising an inhibitor of group II intron splicing to a subject in need thereof. In one embodiment, the disease or disorder is selected from the group consisting of a bacterial infection, a yeast infection, a fungal infection, and a parasite infection. In one embodiment, the subject is a mammal. In one embodiment, the mammal is a human. In one embodiment, the inhibitor of group II intron splicing is at least one of a protein, a peptide, a peptidomimetic, an antibody, a ribozyme, a small molecule chemical compound, a nucleic acid, an aptamer, a modified nucleic acid, a vector, and an antisense nucleic acid molecule.

In one embodiment, the inhibitor of group II intron splicing is a small molecule chemical compound.

In one embodiment, the inhibitor of group II intron splicing is a small molecule chemical compound of Formula (I) or a salt thereof;

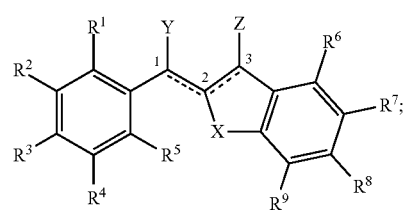

Formula (I)

wherein in Formula (I):

X is O, S, or $NR^{10}$;

$R^1$, $R^2$, $R^3$, $R^4$, $R^5$, $R^6$, $R^7$, $R^8$, $R^9$, and $R^{10}$ are each independently selected from the group consisting of H, $-C_1$-$C_6$ alkyl, $-C_1$-$C_6$ fluoroalkyl, $-C_1$-$C_6$ heteroalkyl, aryl, heteroaryl, cycloalkyl, heterocycloalkyl, F, Cl, Br, I, $-CN$, $-NO_2$, $-OH$, $-OR^{11}$, $-SR^{11}$, $-S(=O)R^{11}$, $-S(=O)_2R^{11}$, $-NHS(=O)_2R^{11}$, $-C(=O)R^{11}$, $-OC(=O)R^{11}$, $-CO_2R^{11}$, $-OCO_2R^{11}$, $-CH(R^{11})_2$, $-N(R^{11})_2$, $-C(=O)N(R^{11})_2$, $-C(=O)NHR^{11}$, $-OC(=O)N(R^{11})_2$, $-NHC(=O)NH(R^{11})$, $-NHC(=O)R^{11}$, $-NHC(=O)OR^{11}$, $-C(OH)(R^{11})_2$, and $-C(NH_2)(R^{11})_2$, and combinations thereof;

or optionally two adjacent $R^1$-$R^5$ or $R^6$-$R^9$ are joined to form a ring;

each occurrence of $R^{11}$ is independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, and combinations thereof; and wherein only one of the two following conditions is met:
condition 1, wherein the bond between carbons 1 and 2 is a single bond, the bond between carbons 2 and 3 is a double bond, Y is (═O), and Z is H; or
condition 2, wherein the bond between carbons 1 and 2 is a double bond, the bond between carbons 2 and 3 is a single bond, Y is H, and Z is (═O).

In one embodiment, the inhibitor of group II intron splicing is a small molecule chemical compound of Formula (V) or a salt thereof;

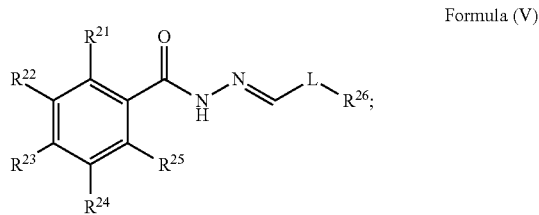

Formula (V)

wherein in Formula (V):
L is a divalent linking group selected from the group consisting of a single bond and ethylene;
$R^{21}$, $R^{22}$, $R^{23}$, $R^{24}$, and $R^{25}$ are each independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$SR^{27}$, —S(═O)$R^{27}$, —S(═O)$_2R^{27}$, —NHS(═O)$_2R^{27}$, —C(═O)$R^{27}$, —OC(═O)$R^{27}$, —$CO_2R^{27}$, —$OCO_2R^{27}$, —CH($R^{27}$)$_2$, —N($R^{27}$)$_2$, —C(═O)N($R^{27}$)$_2$, —C(═O)NH$R^{27}$, —OC(═O)N($R^{27}$)$_2$, —NHC(═O)NH($R^{27}$), —NHC(═O)$R^{27}$, —NHC(═O)O$R^{27}$, —C(OH)($R^{27}$)$_2$, and —C($NH_2$)($R^{27}$)$_2$, and combinations thereof;
or optionally two adjacent $R^{21}$-$R^{25}$ are joined to form a ring;
each occurrence of $R^{27}$ is independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, and combinations thereof; and
$R^{26}$ is selected from the group consisting of an aryl group and a heteroaryl group, wherein the aryl or heteroaryl group may be optionally substituted.

In one embodiment, the organism is selected from the group consisting of a bacteria, a yeast, a fungus, a protist, a parasite, and a plant.

In one embodiment, administration of the inhibitor reduces or prevents at least one of biofilm and algae formation.

BRIEF DESCRIPTION OF THE DRAWINGS

FIG. 1A depicts the sequences of exemplary fluorescently labeled hydrolysable (SEQ ID NO:9) and non-hydrolyzable (SEQ ID NO:10) substrates used in this study. FIG. 1B depicts a schematic of the fluorescent assay used for high throughput screening (HTS) and for determination of the $IC_{50}$ values shown in Table 2. FIG. 1C depicts exemplary experimental results demonstrating that fluorescence is only observed when the ribozyme is incubated with the substrate under proper reaction conditions (in the presence of magnesium ions). FIG. 1D depicts examples of hits identified by HTS.

FIG. 22A depicts a crystal structure of the *Oceaonobacillus iheyensis* (O.i.) group II intron. The active site domain of the ribozyme is shown in black, and the scaffolding domains in gray. Cavities in the molecule (identified by the PyMol Molecular Graphics System, version 1.8 Schroedinger, LLC) shown as potential sites for binding of small molecules, are indicated with space filling. FIG. 22B (top), depicts a schematic of the fluorescent assay used for HTS and for the $IC_{50}$ determination, and (bottom) representative $IC_{50}$ values (Table 2) were obtained by plotting relative fluorescence vs the inhibitor concentration. FIG. 22C (top), depicts the schematic of the self-splicing assay used to determine $K_i$ values for the group II intron splicing inhibitors, and (bottom) representative $K_i$ values (FIG. 24, Table 2) were determined by plotting the rate constants ($k_{obs}$ values) versus inhibitor concentration.

FIG. 23A depicts a diagram of the secondary structure of the ai5γ *S. cerevisiae* group II intron with short exons. Long-range tertiary contacts are indicated by Greek letters. FIG. 23B depicts an alignment of the catalytic Domain 5 from the ai5γ group II intron from *S. cerevisiae* (SEQ ID NO:11) and from the group II intron from *Candida parapsilosis* (SEQ ID NO:12).

FIGS. 25A-25D depict exemplary experimental results demonstrating the determination of $K_i$ values for compounds of interest. FIG. 25A depicts representative gels showing lariat intron formation in the absence (top) and in the presence of indicated concentrations of APY-024. FIG. 25A depicts representative time courses of lariat intron formation in the presence and in the absence of APY-024 at indicated concentrations ranging from 5 nM to 1 mM. Fraction of lariat intron was quantified at each time point and plotted vs time to determine $k_{obs}$ for each concentration of the inhibitor. These values were then plotted vs the inhibitor concentration to determine the Ki values for each inhibitor (Table 1). FIG. 25C depicts representative plots of $k_{obs}$ versus the inhibitor concentrations for different inhibitors, which were then used to determine the Ki values (Table 1). FIG. 25D depicts representative time courses of lariat intron formation before and after ten-fold dilution of inhibitor (Intronistat B (NED-2020)). All experiments were repeated twice to ensure reproducibility. Error bars=s.e.m.

FIG. 26A depicts a comparison of wild-type (WT) and intronless *S. cerevisiae* strain growth in the presence of APY-101 (Intronistat A). From left to right, approximately 22,500, 4,500, and 900 cells of the indicated strains were plated on either YP 2% glucose or YP 3% glycerol 3% ethanol media containing DMSO vehicle or APY-101 (Intronistat A) at 128 µg/mL for growth at 30° C. FIG. 26B depicts experimental results demonstrating that active compounds inhibit splicing of COX1 aI5 g group II intron in vivo. *S. cerevisiae* were grown in the presence of DMSO vehicle, active compounds NED-2020 (Intronistat B), APY-101 (Intronistat A), and APY-081, inactive compound APY-014, or amphotericin B (AmphB). Relative levels of total and unspliced levels of COX1 indicated by qRT-PCR quantification of amplicons covering the eighth exon (total) or the intron-exon junction from the group IIA introns aI1 and aI2, the group I introns aI5α and aI5β, or the group IIB intron aI5γ. Levels of total and unspliced nuclear-encoded YRA1 and MTR2 indicated by quantification of amplicons covering an exon (total) or intron-exon junction of the splicesomal targeted intron. Mean values and s.e.m. from n=4 independent experiments are shown with ACT1 as a standard.

FIG. 27A depicts a comparison of wild-type (WT) and intronless *S. cerevisiae* strain growth in the presence of active compound Intronistat A. From left to right, approximately 22,500, 4,500, and 900 cells of the indicated strains were plated on YP 3% glycerol 3% ethanol media containing Intronistat A at 64 µg/mL for growth at 30° C. FIG. 27B depicts that active compounds inhibit splicing of COX1 aI5γ group II intron in vivo. *S. cerevisiae* were grown in the presence of DMSO vehicle, active compound NED-2020 (Intronistat B), APY-101 (Intronistat A), and APY-081, inactive APY-014, or amphotericin B (AmphB). Relative levels of total and unspliced levels of COX1 indicated by qRT-PCR quantification of amplicons covering the eighth exon (total) or the intron-exon junction from the group IIA introns aI1 and aI2, the group I introns aI5α and aI5β, or the group IIB intron aI5γ. Levels of total and unspliced nuclear-encoded YRA1 and MTR2 indicated by quantification of amplicons covering an exon (total) or intron-exon junction of the splicesomal targeted intron. Mean values and s.e.m. from n=4 independent experiments are shown with PGK1 as a standard.

FIG. 28A depicts the inhibition of the ai5γ group II intron splicing in the presence of excess of different RNAs: unlabeled SE RNA, intronic domains D1, D3 and D56, yeast U2-U6 hairpin and yeast $tRNA_{Phe}$. The average and s.e.m. (error bars) are calculated from n=3 independent experiments. FIG. 28B depicts group I intron splicing is unaffected by the most potent inhibitor of group IIB intron splicing, Intronistat B. Representative time courses of Azoarcus pre-tRNA (Ile) group I intron splicing in the absence and in the presence of the inhibitor Intronistat B at indicated concentrations. Fraction of precursor was quantified at each time point, plotted vs time and fit to a double-exponential equation to determine the reaction rate constants (1 $min_{-1}$ for the fast population and 0.02 $min_{-1}$ for the slow population). Data represent average of n=3 independent experiments, error bars are s.e.m.

FIG. 29A depicts that HEK-293T cells were grown in the presence of compounds at concentrations ranging from 0.125 µg/ml to 128 µg/ml (0.031 µg/ml to 32 µg/ml for Terfenadine, which was used as a cytotoxic control). After 24 hours, viability was assessed with the luminescent Cell Titer Glo cell viability assay and $IC_{50}$ values (Table 2) were determined by fitting the data to a 4-parameter logistic function. FIG. 29B depicts cells were grown as in (FIG. 29A), but analyzed for viability after 72 hours growth in the presence of compounds as described in Methods. $IC_{50}$ values for compounds APY-081, APY-084 and Intronistat A after 72-hour incubation were 0.79±0.09 µg/ml, 1.00±0.04 µg/ml and 1.3±0.1 µg/ml, respectively. Data represent average of n=4 independent experiments for APY-081, Intronistat A and Intronisat B, and n=3 independent experiments for APY-084. Error bars=s.e.m.

DETAILED DESCRIPTION

Figure 1A:
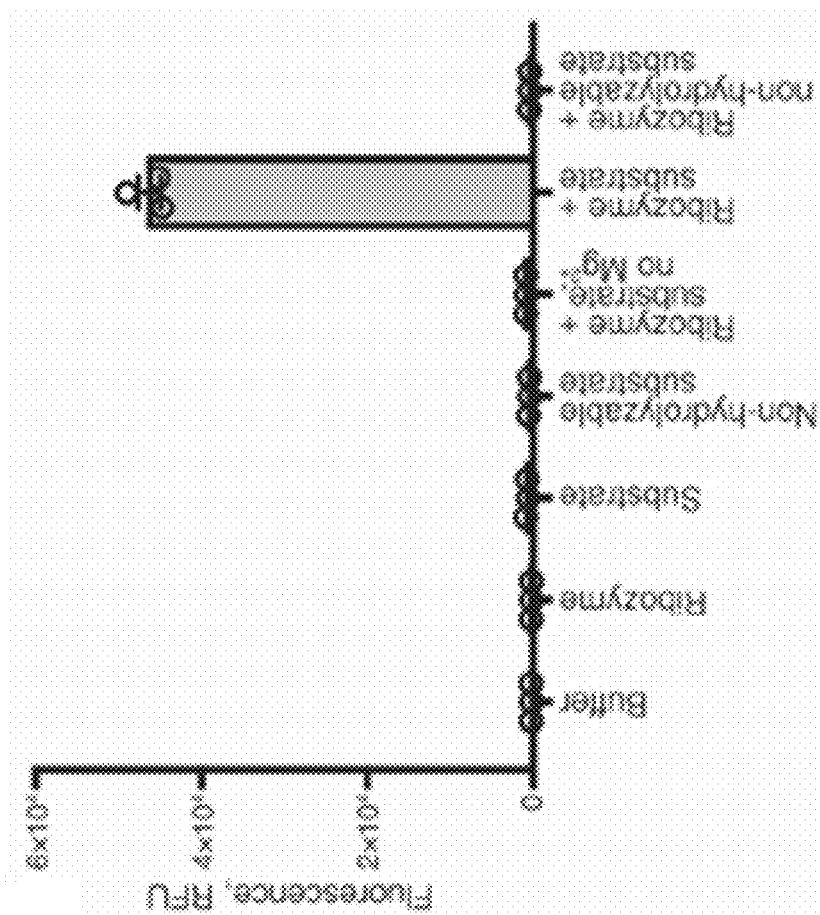
FIGS. 1A-1D depict a fluorescent assay developed to screen inhibitors of group II intron splicing.
Figure 1B:
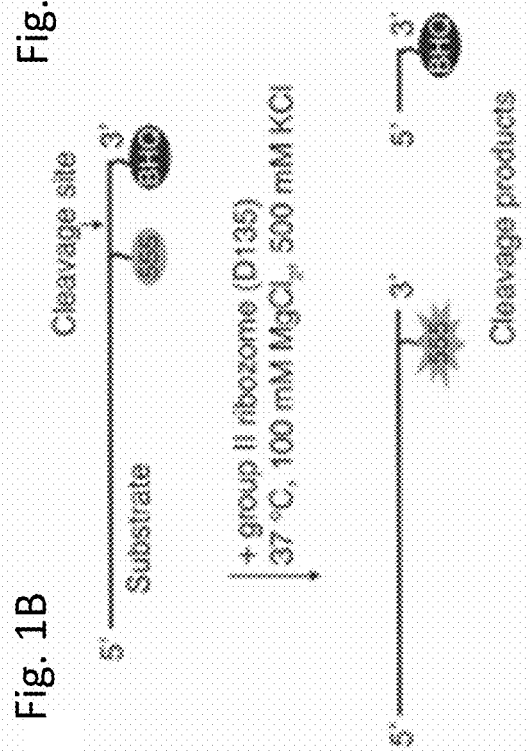
Figure 1C:
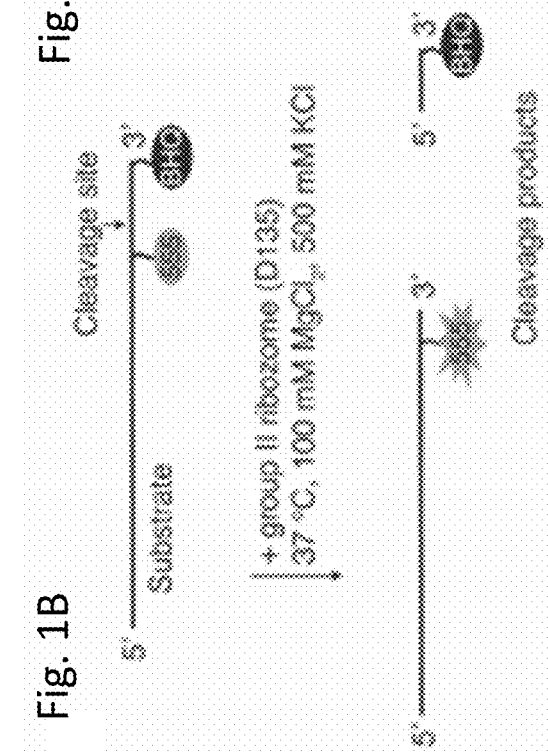
Figure 1D:
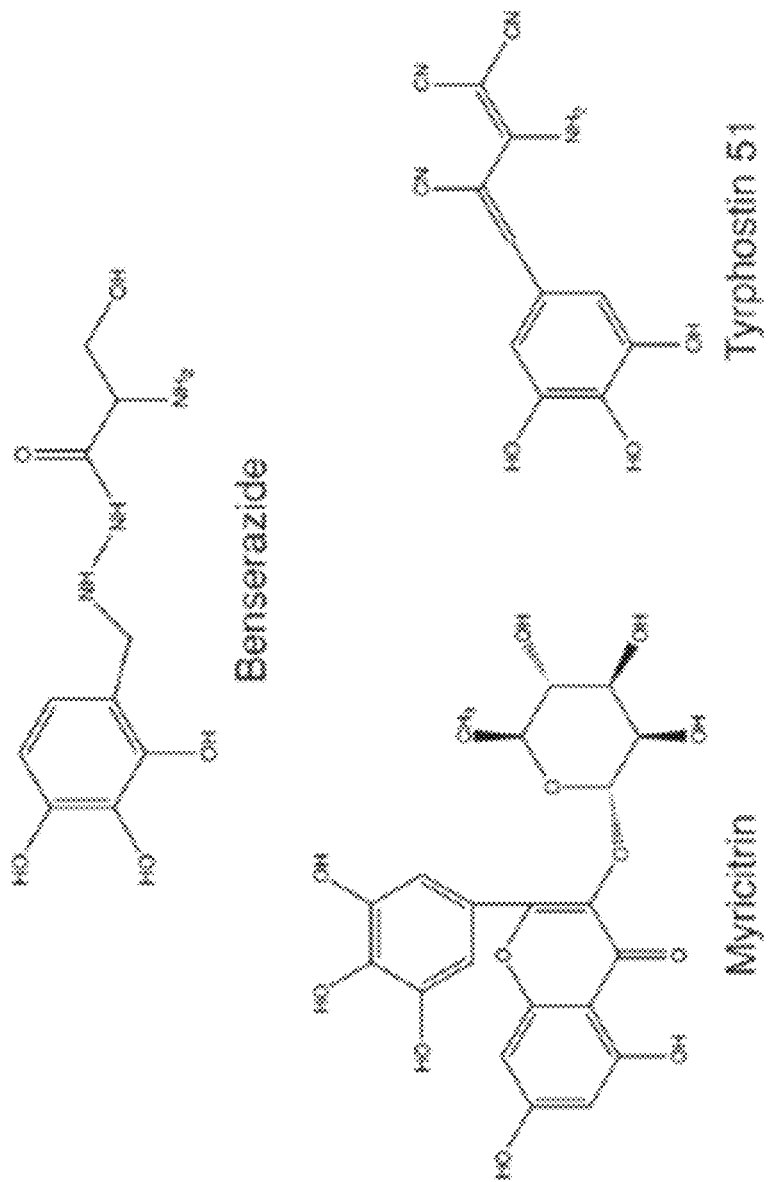

The present invention relates to compositions and methods for inhibiting group II intron splicing. In some embodiments, the invention relates to compositions and methods for inhibiting group II intron splicing for use as anti-microbial and anti-fungal agents. The invention is based, in part, on the unexpected discovery that group II introns fold into a structure that can be targeted to prevent the intron from splicing. Moreover, small molecule inhibitors of group II intron splicing have been identified as potential therapeutic compounds that can prevent growth of organisms that harbor group II introns.

In one embodiment, the composition of the invention comprises an inhibitor of group II intron splicing. In one embodiment, the inhibitor of group II intron splicing is any compound, molecule, or agent that reduces, inhibits, or prevents the self-splicing or ribozyme function of a group II intron.

In one embodiment, the method of the present invention comprises inhibiting group II intron splicing. In one embodiment, the invention provides a method for preventing, inhibiting, or disrupting the growth of organisms that harbor group II introns.

In one embodiment, the method is useful for treating or preventing a disease associated with an organism that harbors a group II intron. In one embodiment, the method comprises administering to a subject an effective amount of a composition comprising an inhibitor of group II intron splicing.

In one embodiment, the method is useful for inhibiting or disrupting growth of organisms that harbor group II introns. For example, the method can be used to inhibit or disrupt growth of organisms that harbor group II introns in a commercial, industrial, or marine setting. For example, in certain embodiments, the method can be used to inhibit or disrupt growth of organisms that harbor group II introns on a kitchen, bathroom, or pool surface. In certain embodiments, the method can be used to inhibit or disrupt growth of organisms that harbor group II introns on marine surfaces, including, but not limited to, piers, docks, boats, buoys, and the like.

Definitions

Unless defined otherwise, all technical and scientific terms used herein have the same meaning as commonly understood by one of ordinary skill in the art to which this invention belongs. Any methods and materials similar or equivalent to those described herein can be used in the practice or testing of the present invention.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, NY, and Ausubel et al., 2002, Current Protocols in Molecular Biology, John Wiley & Sons, NY), which are provided throughout this document.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of a compound which is sufficient to provide a beneficial effect to the subject to which the compound is administered.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The terms "patient," "subject," "individual," and the like are used interchangeably herein, and refer to any animal, or cells thereof whether in vitro or in vivo, amenable to the methods described herein. In some non-limiting embodiments, the patient, subject or individual is a human.

A "therapeutic" treatment is a treatment administered to a subject who exhibits signs or symptoms of a disease or disorder, for the purpose of diminishing or eliminating those signs or symptoms.

As used herein, "treating a disease or disorder" means reducing the severity and/or frequency with which a sign or symptom of the disease or disorder is experienced by a patient.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific.

In some instances, the terms "specific binding" or "specifically binding," can be used in reference to the interaction of an antibody, a protein, a peptide, or a nucleic acid (e.g., RNA or DNA) with a second chemical species, to mean that the interaction is dependent upon the presence of a particular sequence or structure (e.g., a specific nucleotide sequence or epitope) on the chemical species; for example, an siRNA or riboswitch recognizes and binds to a specific nucleotide sequence rather than to nucleic acid molecules generally. If a siRNA is specific for sequence "A", the siRNA will specifically bind to a molecule containing sequence A.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In one embodiment, all nucleotide residues of the first portion are capable of base pairing with nucleotide residues in the second portion.

The term "DNA" as used herein is defined as deoxyribonucleic acid.

The term "RNA" as used herein is defined as ribonucleic acid.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "fusion polypeptide" refers to a chimeric protein containing a protein of interest (e.g., luciferase) joined to a heterologous sequence (e.g., a non-luciferase amino acid or protein).

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

The term "operably linked" as used herein refers to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in an inducible manner.

An "inducible" promoter is a nucleotide sequence which, when operably linked with a polynucleotide which encodes or specifies a gene product, causes the gene product to be produced substantially only when an inducer which corresponds to the promoter is present.

A "constitutive" promoter is a nucleotide sequence which, when operably linked with a polynucleotide which encodes or specifies a gene product, causes the gene product to be produced in a cell under most or all physiological conditions of the cell.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, a "peptidomimetic" is a compound containing non-peptidic structural elements that is capable of mimicking the biological action of a parent peptide. A peptidomimetic may or may not comprise peptide bonds.

The term "RNA" as used herein is defined as ribonucleic acid.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

The term "recombinant polypeptide" as used herein is defined as a polypeptide produced by using recombinant DNA methods.

As used herein, "conjugated" refers to covalent attachment of one molecule to a second molecule.

As used herein, the term "transdominant negative mutant" refers to a nucleic acid encoding a polypeptide or protein product that prevents other copies of the same gene or gene product, which have not been mutated (i.e., which have the wild-type sequence) from functioning properly (e.g., by inhibiting wild type protein function). The product of a transdominant negative mutant nucleic acid is referred to herein as "dominant negative" or "DN" (e.g., a dominant negative protein, or a DN protein).

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The phrase "anti-bacterial agent," "antibiotic" as used herein means a compound or composition useful in reducing or preventing the viability or proliferation of a bacteria; or in treating or preventing a bacterial infection.

The phrase "anti-fungal agent," as used herein means a compound or composition useful in reducing or preventing the viability or proliferation of a fungus or yeast; or in treating or preventing a fungal infection.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —NH$_2$, amino, azido, —N(CH$_3$)$_2$, —C(=O)OH, trifluoromethyl, —C(=O)O(C$_1$-C$_4$)alkyl, —C(=O)NH$_2$, —SO$_2$NH$_2$, —C(=NH)NH$_2$, and —NO$_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include:
—O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

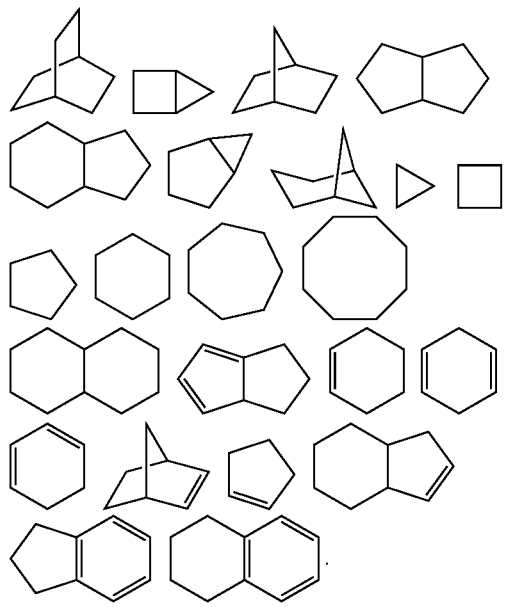

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heterocycloalkyl" or "heterocyclyl" refers to a cyclic group containing one to four ring heteroatoms each selected from O, S, and N. In one embodiment, each heterocycloalkyl group has from 4 to 10 atoms in its ring system, with the proviso that the ring of said group does not contain two adjacent 0 atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine.

Other non-limiting examples of heterocycloalkyl groups are:

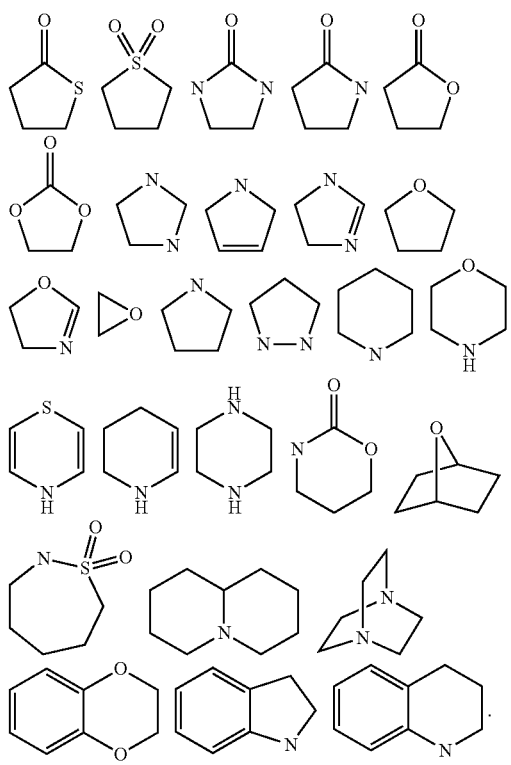

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$— phenyl, —$CH_2$-phenyl (benzyl), aryl-$CH_2$— and aryl-CH ($CH_3$)—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —$CH_2CH_2$-pyridyl. The term "substituted heteroaryl-($C_1$-$C_3$)alkyl" means a heteroaryl-($C_1$-$C_3$)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

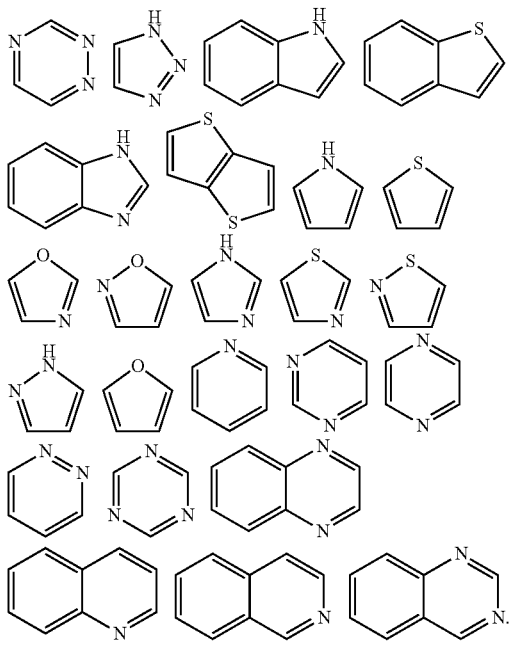

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —$NH_2$, —OH, —$NH(CH_3)$, —$N(CH_3)_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O) 2 alkyl, S(=O) 2 N[H, alkyl, or aryl], —C(=O)NH[substituted or unsubstituted alkyl, or substituted or unsubstituted phenyl], —C(=O)N[H or substituted or unsubstituted alkyl or aryl]$_2$, —OC(=O)N[substituted or unsubstituted alkyl]$_2$, —NHC(=O)NH[substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C($NH_2$)[substituted or unsubstituted alkyl]$_2$. In another embodiment, by way of example, an optional substituent is selected from oxo, fluorine, chlorine, bromine, iodine, —CN, —NH 2, —OH, —$NH(CH_3)$, —$N(CH_3)_2$, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$OCH_2CF_3$, —$S(=O)_2$—$CH_3$, —$C(=O)NH_2$, —C(=O)—$NHCH_3$, —$NHC(=O)NHCH_3$, —$C(=O)CH_3$, —$ON(O)_2$, and —C(=O)OH. In yet one embodiment, the substituents are independently selected from the group consisting of $C_{1-6}$ alkyl, —OH, $C_{1-6}$ alkoxy, halo, amino, acetamido, oxo and nitro. As used herein, where a substituent is an alkyl or alkoxy group, the carbon chain may be branched, straight or cyclic.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

In eukaryotes, the self-splicing group II intron is a RNA tertiary structure that is absent in vertebrates but essential for respiration in plants, fungi, yeast, bacteria, ichthyosporea and worms. In yeast and some fungi, it is located in mitochondria and it interrupts housekeeping genes essential for respiration. In plants, group II introns can be located in genes within the chloroplast and/or the mitochondrial genome, where they frequently interrupt genes important for respiration and other metabolic functions. Without being bound by any particular theory, it is believed that group II introns are important for gene expression in a diversity of unicellular and multicellular eukaryotic organisms, including parasites. The invention is based, in part, on the discovery that inhibition of group II introns results in the growth inhibition of pathogenic and nonpathogenic yeast species and that high affinity compounds can be generated that specifically, inhibit group II intron splicing in-vitro and in-vivo and that lack toxicity in human cells. For example, it is demonstrated herein that the compounds are potent growth inhibitors of the pathogen *Candida parapsilosis*, displaying antifungal activity comparable with amphotericin B.

In one embodiment, the present invention relates to compositions and methods for inhibiting group II introns, including inhibiting group II intron splicing. In some embodiments, the invention relates to preventing, inhibiting, or disrupting the growth of an organism harboring an active group II intron (i.e., a group II intron that is capable of self-splicing).

In some embodiments, the invention relates to treating or preventing a disease or disorder associated with an organism harboring an active group II intron. In one embodiment, the group II intron splicing inhibitor of the invention is used as a therapeutic agent for treatment of a disease or disorder. In one embodiment, the disease or disorder is selected from the group consisting of a fungal infection, a yeast infection, and a bacterial infection. In one embodiment, the disease or disorder is associated with a fungal infection, a yeast infection, or a bacterial infection.

In one embodiment, the present invention relates to compositions and methods for reducing or preventing the growth of an organism that harbors a group II intron. Therefore, in one embodiment, the group II intron splicing inhibitor of the invention is used to reduce or prevent the growth of a plant, a fungus, a yeast, a bacteria or a protist.

In one embodiment, the present invention provides a composition comprising an inhibitor of group II intron splicing. In one embodiment, the inhibitor of group II intron splicing is selected from a protein, a peptide, a peptidomimetic, an antibody, a ribozyme, a small molecule chemical compound, a nucleic acid, a vector, and an antisense nucleic acid molecule.

In one embodiment, the inhibitor of group II intron splicing is a small molecule chemical compound. Exemplary small molecule chemical compounds include aurones, 2-benzoylbenzofurans, and benzoyl hydrazones.

In one embodiment, the invention provides methods for treating or preventing a disease or disorder associated with an organism harboring an active group II intron. In one embodiment, the method comprises administering a composition comprising an inhibitor of group II intron splicing to a subject in need thereof. In one embodiment, the subject is a vertebrate animal. In another embodiment, the vertebrate animal is a human.

In one embodiment, the invention provides methods for reducing growth of an organism harboring an active group II intron. In one embodiment, the method comprises contacting an organism harboring an active group II intron with a composition comprising an inhibitor of group II intron splicing.

In one embodiment, the invention provides methods for preventing growth of an organism harboring an active group II intron on a surface or substrate. In one embodiment, the method comprises contacting a surface or substrate with a composition comprising an inhibitor of group II intron splicing.

In one embodiment, the inhibitor of group II intron splicing is at least one of the group consisting of a chemical compound, a protein, a peptide, a peptidomimetic, an antibody, a ribozyme, a small molecule chemical compound, a nucleic acid, a vector, an antisense nucleic acid molecule.
Inhibitors In one embodiment, the present invention provides a composition comprising an inhibitor of group II intron splicing. In one embodiment, an inhibitor of group II intron splicing is any compound, molecule, or agent that reduces, inhibits, or prevents the self-splicing or ribozyme function of group II introns. In one embodiment, an inhibitor of group II intron splicing comprises a nucleic acid, a peptide, a small molecule chemical compound, a siRNA, a ribozyme, an antisense nucleic acid, an antagonist, an aptamer, a peptidomimetic, or any combination thereof.
Small Molecule Inhibitors In various embodiments, the inhibitor is a small molecule chemical compound, including, but limited to, an aurone, a 2-benzoylbenzofuran, or a benzoyl hydrazone.

In one embodiment, the small molecule chemical compound is a compound of Formula (I) or a salt thereof;

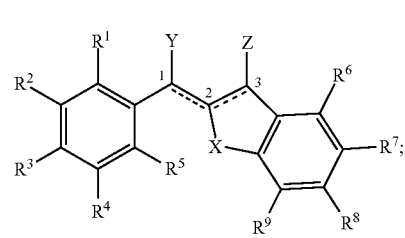

Formula (I)

wherein in Formula (I):
X is O, S, or NR$^{10}$;
R$^1$, R$^2$, R$^3$, R$^4$, R$^5$, R$^6$, R$^7$, R$^8$, R$^9$, and R$^{10}$ are each independently selected from the group consisting of H, —C$_1$-C$_6$ alkyl, —C$_1$-C$_6$ fluoroalkyl, —C$_1$-C$_6$ heteroalkyl, aryl, heteroaryl, cycloalkyl, heterocycloalkyl, F, Cl, Br, I, —CN, —NO$_2$, —OH, —OR$^{11}$, —SR$^{11}$, —S(=O)R$^{11}$, —S(=O)$_2$R$^{11}$, —NHS(=O)$_2$R$^{11}$, —C(=O)R$^{11}$, —OC(=O)R$^{11}$, —CO$_2$R$^{11}$, —OCO$_2$R$^{11}$, —CH(R$^{11}$)$_2$, —N(R$^{11}$)$_2$, —C(=O)N(R$^{11}$)$_2$, —C(=O)NHR$^{11}$, —OC(=O)N(R$^{11}$)$_2$, —NHC(=O)NH(R$^{11}$), —NHC(=O)R$^{11}$, —NHC(=O)OR$^{11}$, —C(OH)(R$^{11}$)$_2$, and —C(NH$_2$)(R$^{11}$)$_2$, and combinations thereof
or optionally two adjacent R$^1$-R$^5$ or R$^6$-R$^9$ are joined to form a ring;
each occurrence of R$^{11}$ is independently selected from the group consisting of H, —C$_1$-C$_6$ alkyl, —C$_1$-C$_6$ fluoroalkyl, —C$_1$-C$_6$ heteroalkyl, aryl, heteroaryl, cycloalkyl, heterocycloalkyl, F, Cl, Br, I, —CN, —NO$_2$, —OH, and combinations thereof; and
wherein only one of the two following conditions is met:

condition 1, wherein the bond between carbons 1 and 2 is a single bond, the bond between carbons 2 and 3 is a double bond, Y is (═O), and Z is H; or condition 2, wherein the bond between carbons 1 and 2 is a double bond, the bond between carbons 2 and 3 is a single bond, Y is H, and Z is (═O).

In one embodiment, the small molecule chemical compound of Formula (I) is a compound of Formula (II):

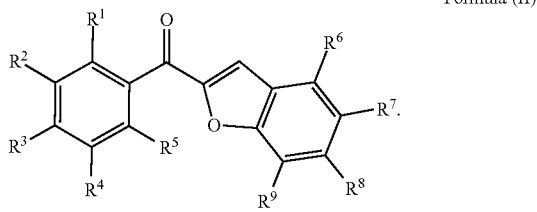

Formula (II)

In one embodiment, the compound of Formula (I) is a compound of Formula (III):

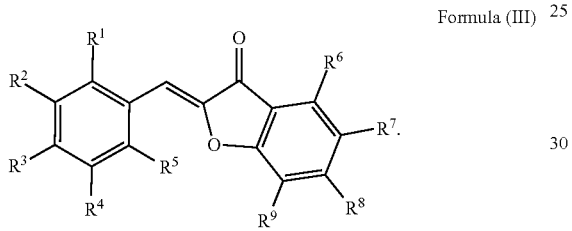

Formula (III)

In one embodiment, $R^2$, $R^3$, and $R^4$ are OH. In one embodiment, $R^6$ and $R^8$ are OH. In one embodiment, $R^7$ and $R^9$ are Cl.

In one embodiment, $R^7$ is represented by Formula (IV):

Formula (IV)

wherein * represents the attachment to Formula (I), (II), or (III);

$A^1$, $A^2$, $A^3$, and $A^4$ are $CR^{13}$ or N;

$R^{12}$ is selected from the group consisting of H, $C_1$-$C_6$ alkyl, $C_1$-$C_6$ fluoroalkyl, $C_1$-$C_6$ perfluoroalkyl, $C_1$-$C_6$ heteroalkyl, aryl, heteroaryl, cycloalkyl, heterocycloalkyl, F, Cl, Br, I, —CN, —$NO_2$, —OH, —$OR^{14}$, —$SR^{14}$, —S(═O)$R^{14}$, —S(═O)$_2R^{14}$, —S(═O)$_2$NH$R^{14}$, —S(═O)$_2$N($R^{14}$)$_2$, —NHS(═O)$_2R^{14}$, —C(═O)$R^{14}$, —OC(═O)$R^{14}$, —$CO_2R^{14}$, —$OCO_2R^{14}$, —CH($R^{14}$)$_2$, —N($R^{14}$)$_2$, —C(═O)N($R^{14}$)$_2$, —C(═O)NH$R^{14}$, —OC(═O)N($R^{14}$)$_2$, —NHC(═O)NH($R^{14}$), —NHC(═O)$R^{14}$, —NHC(═O)$OR^{14}$, —C(OH)($R^{14}$)$_2$, and —C($NH_2$)($R^{14}$)$_2$, and combinations thereof;

each occurrence of $R^{13}$ is independently selected from the group consisting of H, $C_1$-$C_6$ alkyl, F, Cl, Br, I, —CN, —$NO_2$, —OH, —$CF_3$, $C_1$-$C_6$ heteroalkyl, aryl-($C_1$-$C_3$) alkyl, and cycloalkyl; or optionally two adjacent $R^{13}$ are joined to form a ring;

each occurrence of $R^{14}$ is independently selected from the group consisting of H, $C_1$-$C_6$ alkyl, F, Cl, Br, I, —CN, —$NO_2$, —OH, —$CF_3$, $C_1$-$C_6$ heteroalkyl, aryl-($C_1$-$C_3$) alkyl, and cycloalkyl; or optionally two $R^{14}$ on the same atom may together form a ring.

In one embodiment, $A^1$, $A^2$, $A^3$, and $A^4$ are $CR^{13}$. In one embodiment, $A^1$, $A^3$, and $A^4$ are $CR^{13}$ and $A^2$ is N. In one embodiment, $A^1$, $A^2$, and $A^4$ are $CR^{13}$ and $A^3$ is N. In one embodiment, $A^1$ and $A^4$ are $CR^{13}$ and $A^2$ and $A^3$ are N.

In one embodiment, $R^8$ is —C(═O)NH$R^{10}$.

In one embodiment, the compound of Formula (I) is selected from the group consisting of:

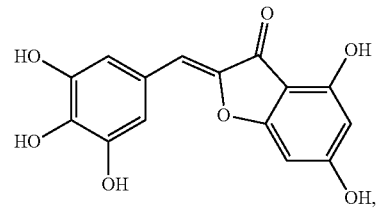

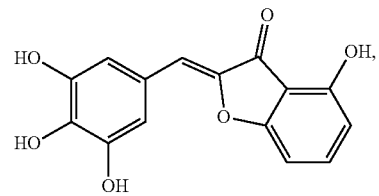

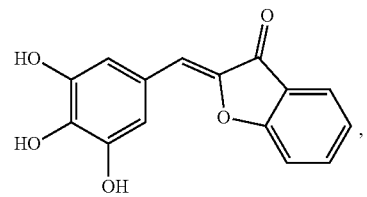

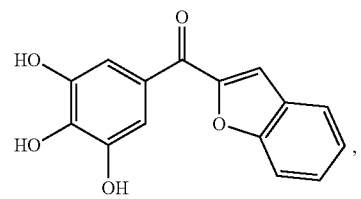

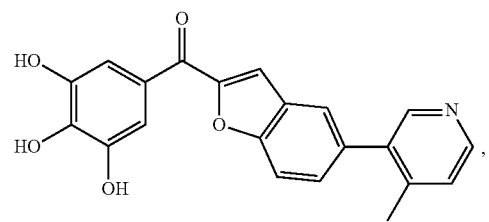

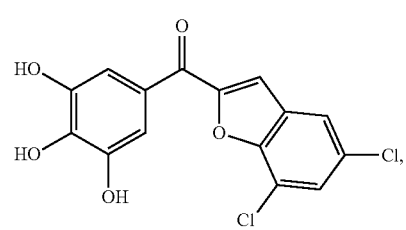

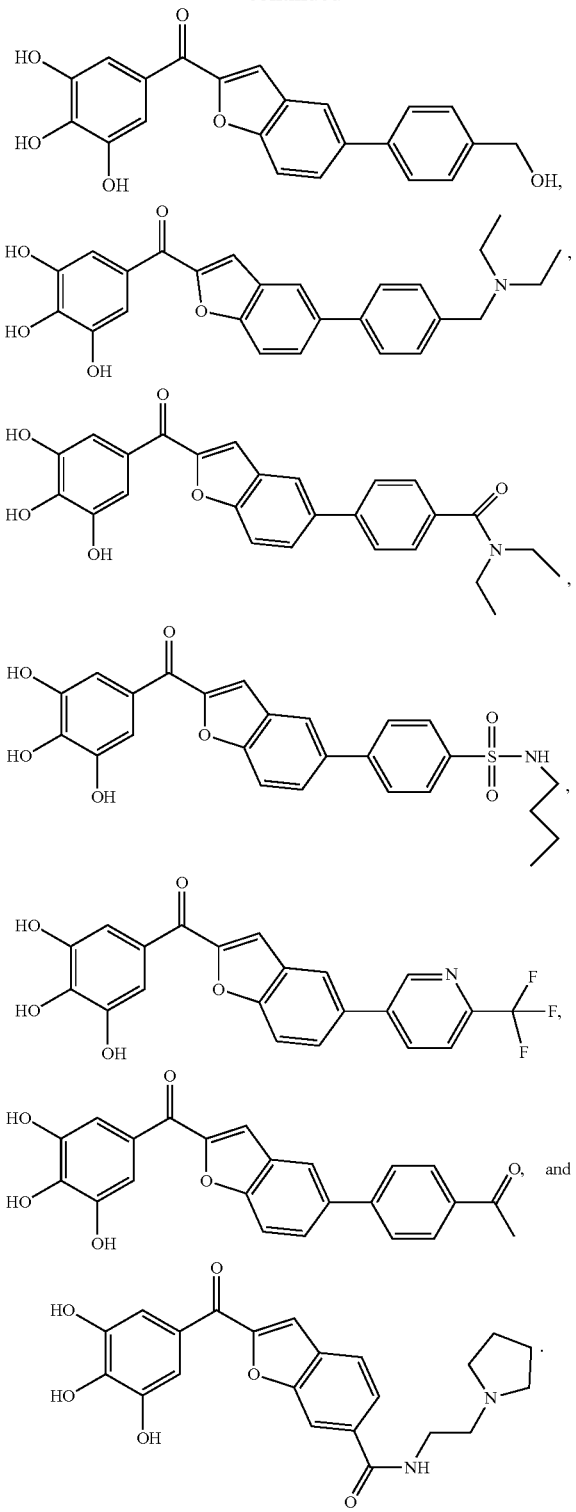

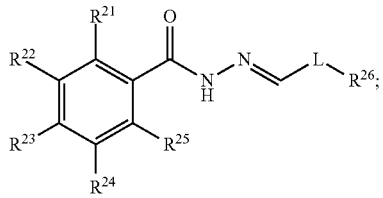

Formula (V)

wherein in Formula (V):
L is a divalent linking group selected from the group consisting of a single bond and ethylene;
$R^{21}$, $R^{22}$, $R^{23}$, $R^{24}$, and $R^{25}$ are each independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$SR^{27}$, —S(=O)$R^{27}$, —S(=O)$_2R^{27}$, —NHS(=O)$_2R^{27}$, —C(=O)$R^{27}$, —OC(=O)$R^{27}$, —$CO_2R^{27}$, —$OCO_2R^{27}$, —CH($R^{27}$)$_2$, —N($R^{27}$)$_2$, —C(=O)N($R^{27}$)$_2$, —C(=O)NH$R^{27}$, —OC(=O)N($R^{27}$)$_2$, —NHC(=O)NH($R^{27}$), —NHC(=O)$R^{27}$, —NHC(=O)O$R^{27}$, —C(OH)($R^{27}$)$_2$, and —C($NH_2$)($R^{27}$)$_2$, and combinations thereof;
or optionally two adjacent $R^{21}$-$R^{25}$ are joined to form a ring;
each occurrence of $R^{27}$ is independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, and combinations thereof; and
$R^{26}$ is selected from the group consisting of an aryl group and a heteroaryl group, wherein the aryl or heteroaryl group may be optionally substituted.

In one embodiment, $R^{22}$, $R^{23}$, and $R^{24}$ are OH.

In one embodiment, $R^{26}$ is an aryl group which may be optionally substituted. In one embodiment, $R^{26}$ is a phenyl group. In one embodiment, $R^{26}$ is a naphthyl group. In another embodiment, $R^{26}$ is a heteroaryl group which may be optionally substituted. In one embodiment, $R^{26}$ is a furyl group. In one embodiment, $R^{26}$ is a pyridinyl group. In one embodiment, $R^{26}$ is a diazenyl group.

In one embodiment, $R^{26}$ is a group of Formula (VI):

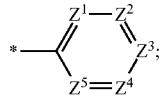

Formula (VI)

wherein in Formula (VI):
\* represents the attachment to Formula (V);
$Z^1$, $Z^2$, $Z^3$, $Z^4$, and $Z^5$ are $CR^{28}$ or N;
each occurrence of $R^{28}$ is independently selected from the group consisting of H, $C_1$-$C_6$ alkyl, F, Cl, Br, I, —CN, —$NO_2$, —OH, —$CF_3$, —$OR^{29}$, —N($R^{29}$)$_2$, —C(=O)$R^{29}$, $C_1$-$C_6$ heteroalkyl, aryl-($C_1$-$C_3$)alkyl, cycloalkyl, alkynyl, and combinations thereof; or optionally two adjacent $R^{28}$ are joined together to form a ring; and
$R^{29}$ is selected from the group consisting of H, $C_1$-$C_6$ alkyl, or heteroaryl-($C_1$-$C_3$)alkyl.

In one embodiment, the compound of Formula (V) is selected from the group consisting of:

In another aspect, the small molecule chemical compound is a compound of Formula (V) or a salt thereof;

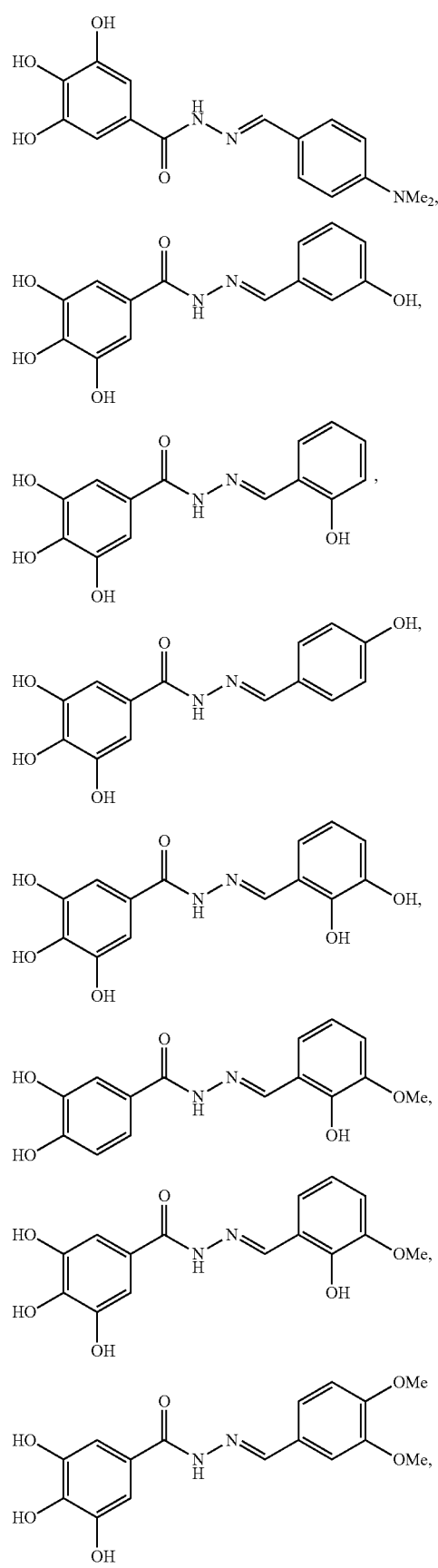
-continued
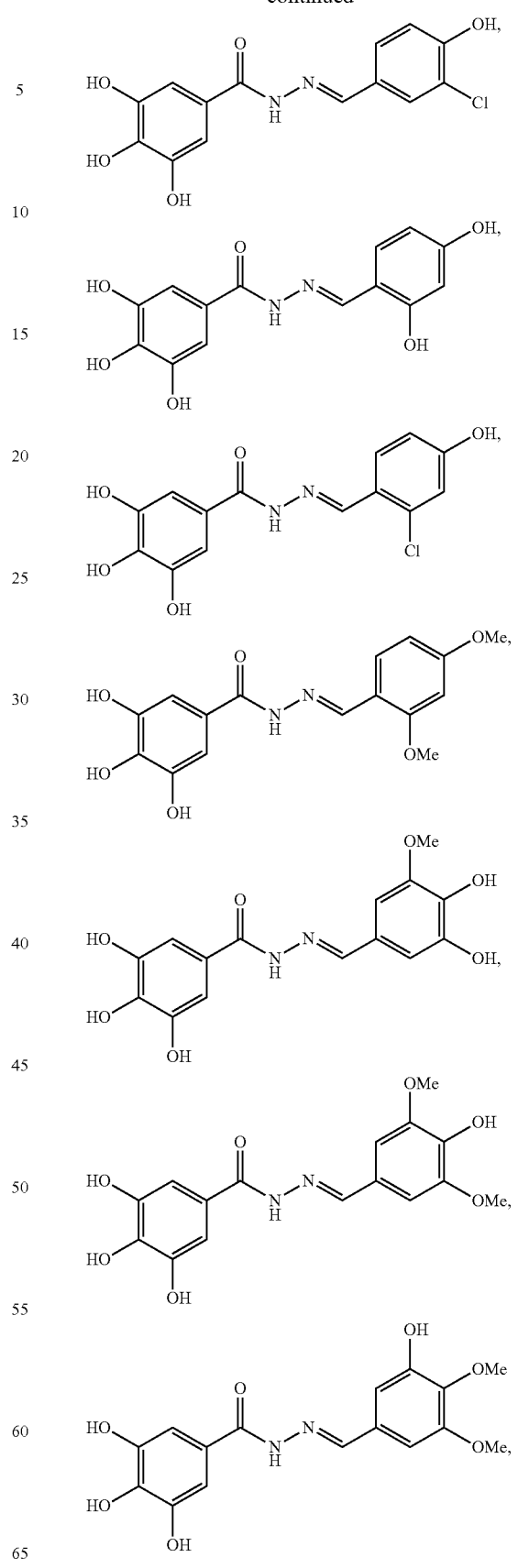

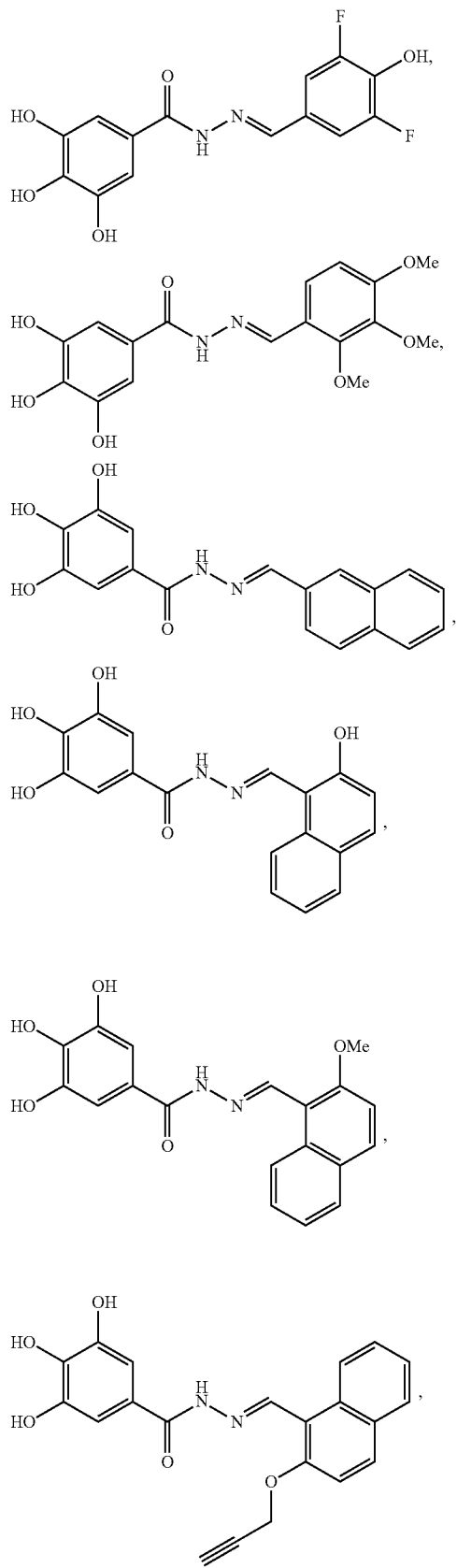

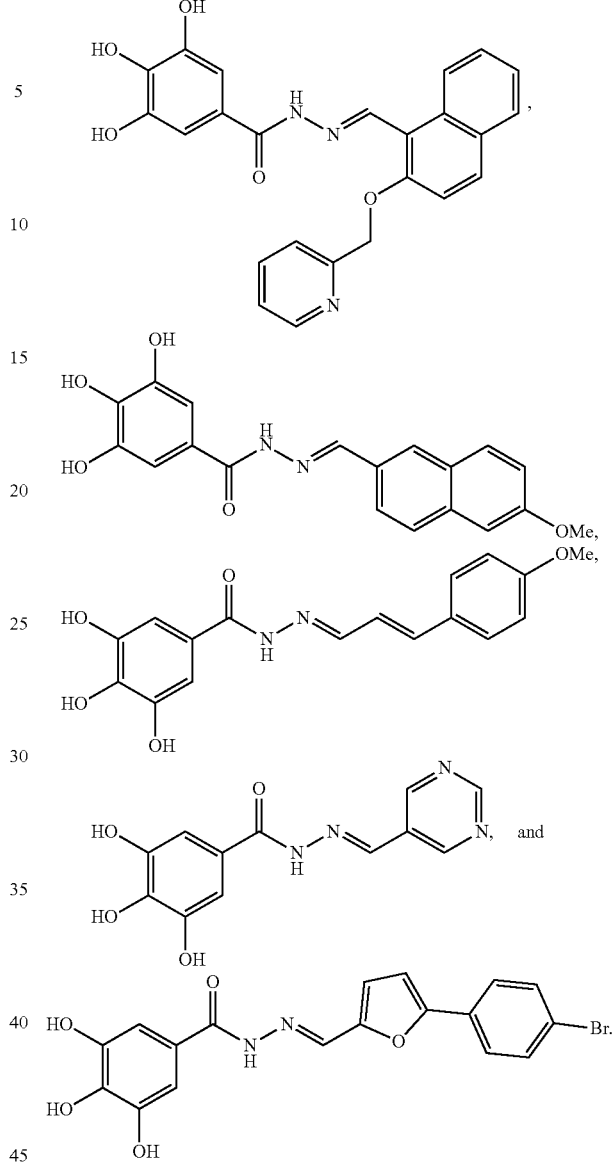

When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like.

Combinatorial libraries of molecularly diverse chemical compounds are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule inhibitor of the invention comprises an analog or derivative of an inhibitor described herein.

In one embodiment, the small molecules described herein are candidates for derivatization. As such, in some instances, the analogs of the small molecules described herein that have modulated potency, selectivity, and solubility are included herein and provide useful leads for drug discovery and drug development. Thus, in some instances, during optimization new analogs are designed considering issues of drug delivery, metabolism, novelty, and safety.

In some instances, small molecule inhibitors described herein are derivatized/analogued as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to inhibit group II introns.

In one embodiment, the small molecule inhibitors described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Nucleic Acid Inhibitors

In some embodiments, the invention includes nucleic acid molecules and gene therapy agents that can inhibit group II intron splicing.

In some instances the inhibitor is an antisense molecule or aptamer, which inhibits a group II intron RNA molecule. Domain V of a group II intron is the most highly conserved domain, and it is indispensable for splicing. Therefore, in one embodiment, an antisense molecule of the invention targets domain V of a group II intron. In one embodiment, the nucleic acid comprises a promoter/regulatory sequence such that the promoter/regulatory sequence is capable of directing expression of the nucleic acid or increasing or decreasing stability of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In one embodiment, siRNA is used to inhibit a group II intron RNA molecule. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, P A (2003); and Gregory J. Hannon, Ed., RNAi A Guide to Gene Silencing, Cold Spring Harbor Laboratory Press, Cold Spring Harbor, NY (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of inhibiting group II intron splicing using RNAi technology.

In another embodiment, the invention includes a vector comprising an siRNA or antisense polynucleotide. In one embodiment, the siRNA or antisense polynucleotide is capable of inhibiting group II intron splicing. The incorporation of a desired polynucleotide into a vector and the choice of vectors is well-known in the art as described in, for example, Sambrook et al. (2012), and in Ausubel et al. (1997), and elsewhere herein.

In some embodiments, the expression vectors described herein encode a short hairpin RNA (shRNA) inhibitor. shRNA inhibitors are well known in the art and are directed against the mRNA of a target, thereby decreasing the expression of the target. In some embodiments, the encoded shRNA is expressed by a cell, and is then processed into siRNA. For example, in some instances, the cell possesses native enzymes (e.g., dicer) that cleaves the shRNA to form siRNA.

The siRNA, shRNA, or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense polynucleotide, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another embodiment, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., 2012). In a particular embodiment, the vector is a vector useful for transforming animal cells.

In one embodiment, the recombinant expression vectors may also contain nucleic acid molecules which encode a peptide or peptidomimetic inhibitor of invention, described elsewhere herein.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202 and 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin (e.g., IgG). The selectable markers may be introduced on a separate vector from the nucleic acid of interest.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987, Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queuosine, and wybutosine and the like, as well as acetyl-methyl-, thio- and other modified forms of adenine, cytidine, guanine, thymine, and uridine.

Antisense molecules and their use for inhibiting RNA molecules are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

In one embodiment, antisense molecules of the invention may be made synthetically. In one embodiment, antisense oligomers of between about 10 to about 30 nucleotides are used, since they are easily synthesized for administration to a subject or a target cell. Synthetic antisense molecules contemplated by the invention include oligonucleotide derivatives known in the art which have improved biological activity compared to unmodified oligonucleotides (see U.S. Pat. No. 5,023,243).

In one embodiment of the invention, a ribozyme is used to inhibit group II intron splicing. Ribozymes useful for inhibiting a target molecule may be designed by incorporating target sequences into the basic ribozyme structure which are complementary, for example, to the mRNA sequence of a group II intron. Ribozymes targeting group II introns may be synthesized using commercially available reagents (Glen Research Corp., Sterling, VA, or BioAutomation, Plano, TX) or they may be genetically expressed from DNA encoding them.

Genome Editing System

In one embodiment, the invention provides for inhibition of group II intron splicing through use of a genome editing system. A series of programmable nuclease-based genome editing technologies have developed (see for example, Hsu et al., Cell 157, Jun. 5, 2014 1262-1278), including, but not limited to, meganucleases, zinc finger nucleases (ZFNs), transcription activator-like effector-based nucleases (TALENs) and CRISPR-Cas systems (see e.g. Platt et al., Cell 159(2), 440-455 (2014); Shalem et al., Science 3 84-87 (2014); and Le Cong et al., Science 339, 819 (2013)) or alternative CRISPR systems. Genome editing systems have a wide variety of utilities including modifying (e.g., deleting, inserting, translocating, inactivating, activating, repressing, altering methylation, transferring specific moieties) a target polynucleotide in a multiplicity of cell types.

In one embodiment, a CRISPR-Cas system, where a guide RNA (gRNA) targeted to a nucleic acid molecule harboring an active group II intron, and a CRISPR-associated (Cas) peptide form a complex to induce mutations within the targeted intron sequence. The CRISPR complex of the invention provides an effective means for modifying a target polynucleotide.

In one embodiment, the composition of the present invention comprises a Cas peptide or Cas-derived peptide and a gRNA targeted to a group II intron or to a DNA sequence encoding a group II intron. In one embodiment, the composition comprises a nucleic acid molecule encoding a Cas peptide or Cas-derived peptide. In one embodiment, the composition comprises a nucleic acid molecule encoding a gRNA targeted to a group II intron or to a DNA sequence encoding a group II intron.

In one embodiment, the target polynucleotide is a DNA molecule. DNA molecules include, but are not limited to, genomic DNA molecules, extrachromosomal DNA molecules, conjugative plasmids and exogenous DNA molecules. In one embodiment, the target polynucleotide is a RNA molecule (see e.g., Batra et al., Cell. 170(5):899-912.e10 (2017) for methods of use of a CRISPR-Cas system to modify an RNA molecule.)

In general, "CRISPR-Cas system" or "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system are derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system).

In some embodiments, the site of nuclease activity is determined by the CRISPR-Cas system guide RNA. In general, a "CRISPR-Cas guide RNA" or "guide RNA" refers to an RNA that directs sequence-specific binding of a CRISPR complex to the target sequence. Typically, a guide RNA comprises (i) a guide sequence that has sufficient complementarity with a target polynucleotide sequence to hybridize with the target sequence and (ii) a trans-activating cr (tracr) mate sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In the context of formation of a CRISPR complex, a "target sequence" or "a sequence of a target DNA" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides or DNA/RNA hybrid polynucleotides. In some embodiments, a target sequence is located in the nucleus or cytoplasm of a cell. In some embodiments, the target sequence may be within an organelle of a eukaryotic cell, for example, mitochondrion or chloroplast.

In some embodiments, the CRISPR-Cas domain comprises a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2. Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, orthologs thereof, or modified versions thereof. In some embodiments, the Cas protein has DNA or RNA cleavage activity. In some embodiments, the Cas protein directs cleavage of one or both strands of a nucleic acid molecule at the location of a target sequence, such as within the target sequence and/or within the complement of the target sequence. In some embodiments, the Cas protein directs cleavage of one or both strands within about 1, 2, 3, 4, 5, 6, 7, 8, 9, 10, 15, 20, 25, 50, 100, 200, 500, or more base pairs from the first or last nucleotide of a target sequence.

In one embodiment, the CRISPR-Cas domain is associated with one or more functional domains. For example, in one embodiment, one or more functional domains may be associated with (i.e. bound to or fused with) the C terminus or the N terminus of the Cas9 enzyme or homolog or ortholog thereof. In such an embodiment, the functional domains are typically fused via a linker. In another embodiment, one or more functional domains may be provided along with the Cas9 enzyme or homolog or ortholog thereof.

The one or more functional domains may have one or more activities including, but not limited to, cytidine deaminase activity, methylase activity, demethylase activity, transcription activation activity, transcription repression activity, transcription release factor activity, histone modification activity, RNA cleavage activity, DNA cleavage activity, DNA integration activity or nucleic acid binding activity. The one or more functional domains may be transcriptional activation domain or a repressor domains.

Activator and repressor domains which may further modulate function may be selected on the basis of species, strength, mechanism, duration, size, or any number of other parameters. Exemplary effector domains include, but are not limited to, a transposase domain, integrase domain, recombinase domain, resolvase domain, invertase domain, protease domain, DNA methyltransferase domain, DNA demethylase domain, histone acetylase domain, histone deacetylases domain, nuclease domain, repressor domain, activator domain, nuclear-localization signal domains, transcription-protein recruiting domain, cellular uptake activity associated domain, nucleic acid binding domain or antibody presentation domain.

In one embodiment, the one or more functional domain may be an APOBEC domain (see e.g., Yang et al., J Genet Genomics. 44(9):423-437 (2017)). APOBEC-catalyzed deamination in single-stranded nucleic acid molecules can be further processed to yield mutations including, but not limited to, insertions or deletions (indels).

Polypeptide Inhibitors

In some embodiments, the invention includes an isolated peptide inhibitor that inhibits group II intron splicing. For example, in one embodiment, the peptide inhibitor of the invention inhibits group II intron splicing directly by binding to a 3-dimensional structure formed during group II intron folding thereby preventing the self-splicing activity of the group II intron.

The variants of the polypeptides according to the present invention may be (i) one in which one or more of the amino acid residues are substituted with a conserved or non-conserved amino acid residue and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Combinations

In one embodiment, the composition of the present invention comprises a combination of an inhibitor of group II intron splicing and second therapeutic agent. For example, in various embodiments the second therapeutic agent includes, but is not limited to an antifungal agent, an antibacterial agent, a parasite infection therapeutic and a yeast infection therapeutic.

In some embodiments, a composition comprising a combination of inhibitors described herein has an additive effect, wherein the overall effect of the combination is approximately equal to the sum of the effects of each individual inhibitor. In other embodiments, a composition comprising a combination of inhibitors described herein has a synergistic effect, wherein the overall effect of the combination is greater than the sum of the effects of each individual inhibitor.

A composition comprising a combination of inhibitors comprises individual inhibitors in any suitable ratio. For example, in one embodiment, the composition comprises a 1:1 ratio of two individual inhibitors. However, the combination is not limited to any particular ratio. Rather any ratio that is shown to be effective is encompassed.

Therapeutic Methods

The present invention also provides methods of treating or preventing a disease or disorder associated with an organism that harbors a group II intron in a subject. In one embodiment, the disease or disorder is a bacterial, parasite, yeast or fungal infection. In one embodiment, the disease or disorder is associated with a bacterial, parasite, yeast or fungal infection.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant signs or symptoms of a disease or disorder do not have to occur before the present invention may provide benefit. Therefore, the present invention includes a method for preventing a disease or disorder, in that a composition, as discussed previously elsewhere herein, can be administered to a subject prior to the onset of a disease or disorder, thereby preventing a disease or disorder.

Exemplary bacteria harboring group II introns include, but are not limited to, *Azotobacter vinelandii; Bacillus anthracis; Bacillus cereus; Bacillus halorudans; Bacillus megaterium; Calothrix* species; *Clostridium difficile; Escherichia coli; Lactococcus lactis; Legionella pneumophila; Pseudomonas alcaligenes; Pseudomonas putida; Pseudomonas* sp.; *Serratia marcescens; Sinorhizobium meliloti; Sphingomonas aromaticivorans; Shigella flexneri;* and *Streptococcus pneumoniae.*

Exemplary yeast harboring group II introns include, but are not limited to, *Candida parapsilosis; Canida zemplinina; Candida Ipomoeae; Saccharomyces cerevisiae;* and *Schizosaccharomyces pombe.*

Exemplary fungi harboring group II introns include, but are not limited to, *Ceripopriopsis subvermispora; Coccidioides immitis; Cordyceps konnoana; Cryphonectria parasitica; Glomus intraradices; Paracoccidioides brasiliensis; Podospora anserine; Tremetes cingulate;* and *Usnea Antarctica.*

One of skill in the art, when armed with the disclosure herein, would appreciate that the prevention of a bacterial, parasite, yeast or fungal infection, encompasses administering to a subject a composition as a preventative measure against the development of, or progression of a bacterial, parasite, yeast or fungal infection.

The invention encompasses administration of an inhibitor of group II intron splicing. To practice the methods of the invention; the skilled artisan would understand, based on the disclosure provided herein, how to formulate and administer the appropriate inhibitor composition to a subject. The present invention is not limited to any particular method of administration or treatment regimen.

In one embodiment, the method comprises administering to the subject in need an effective amount of a composition that reduces or inhibits the self-splicing activity of a group II intron.

One of skill in the art will appreciate that the inhibitors of the invention can be administered singly or in any combination. Further, the inhibitors of the invention can be administered singly or in any combination in a temporal sense, in that they may be administered concurrently, or before, and/or after each other. One of ordinary skill in the art will appreciate, based on the disclosure provided herein, that the inhibitor compositions of the invention can be used to prevent or to treat a bacterial, parasite, yeast or fungal infection, and that an inhibitor composition can be used alone or in any combination with another modulator to effect a therapeutic result. In various embodiments, any of the inhibitor compositions of the invention described herein can be administered alone or in combination with other modulators of other molecules associated with a bacterial, parasite, yeast or fungal infection.

In one embodiment, the invention includes a method comprising administering a combination of inhibitors described herein. In some embodiments, the method has an additive effect, wherein the overall effect of the administering a combination of inhibitors is approximately equal to the sum of the effects of administering each individual inhibitor. In other embodiments, the method has a synergistic effect, wherein the overall effect of administering a combination of inhibitors is greater than the sum of the effects of administering each individual inhibitor.

The method comprises administering a combination of inhibitors in any suitable ratio. For example, in one embodiment, the method comprises administering two individual inhibitors at a 1:1 ratio. However, the method is not limited to any particular ratio. Rather any ratio that is shown to be effective is encompassed.

Gene Therapy

As generally discussed above, a nucleic acid, where applicable, may be employed in gene therapy methods in order to inhibit group II intron splicing. "Gene therapy" includes both conventional gene therapy where a lasting effect is achieved by a single treatment, and the administration of gene therapeutic agents, which involves the one time or repeated administration of a therapeutically effective DNA or mRNA. Oligonucleotides can be modified to enhance their uptake, e.g., by substituting their negatively charged phosphodiester groups by uncharged groups. One or more vector encoding an inhibitor of group II intron splicing of the present invention can be delivered using gene therapy methods, for example locally in a cell or tissue or systemically (e.g., via vectors that selectively target specific tissue types, for example, tissue-specific adeno-associated viral vectors). In some embodiments, primary cells harvested from an individual can be transfected ex vivo with a nucleic acid encoding an inhibitor of group II intron splicing of the present invention, and then returned the transfected cells to the individual's body.

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in cells or target tissues. Such methods can be used to administer nucleic acids encoding an inhibitor of group II intron splicing (e.g., encoding components of a CRISPR system) to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. For a review of gene therapy procedures, see e.g., Anderson, Science 256: 808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357: 455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Other Applications

In one embodiment, the group II splicing inhibitors of the invention are useful for the inhibition, treatment or prevention of growth of an organism harboring an active group II intron. Although the invention finds utility as a therapeutic agent, the present invention is not limited to the treatment or prevention of growth of an organism harboring an active group II intron in the body or in medical settings. It is known in the art that organisms harboring an active group II intron can grow on a variety of surfaces which can lead to diverse detrimental issues. For example, organism growth in kitchen or bathroom surfaces may present a host of sanitation issues. In an alternative embodiment, organism growth on physical surfaces and substrates, engineering systems or vehicles may lead to corrosion and biofouling. Thus, the present invention encompasses the inhibition, treatment or prevention of growth of organisms harboring group II introns that may occur in environmental surfaces and substrates, residential surfaces and substrates, commercial surfaces and substrates, and industrial surfaces and substrates. Therefore, the present invention encompasses the inhibition, treatment or prevention of growth of organisms harboring group II introns that may occur in environmental, residential, commercial, industrial, or other settings.

In one embodiment, growth of an organism that harbors a group II intron results in the formation of a biofilm. Therefore, in one embodiment, the present invention provides a composition that inhibits the formation of biofilms. In one embodiment, the composition inhibits the accumulation of biofilm. In one embodiment, the composition promotes the disruption or disassembly of an existing biofilm.

The present invention is not limited to treating and/or preventing biofilms in a living body, but rather encompasses methods of treating and/or preventing biofilms on surfaces outside the body (e.g., including environmental surfaces and substrates, commercial surfaces and substrates, residential surfaces and substrates, and industrial surfaces and substrates, etc.). For example, biofilms can form on surfaces in damp environments including bathrooms, kitchens, and certain residential, commercial and industrial settings. In some embodiments, the composition described herein is used in a method to treat and/or prevent biofilm formation or accumulation along surfaces in residential, commercial, military, maritime, and industrial settings. The method comprises administering an effective amount of an inhibitor of group II intron splicing to the surface, or to incorporating an effective amount of an inhibitor of group II intro splicing into a surface, substrate, or other protective surface or material.

In one embodiment, the inhibitor of group II intron splicing is incorporated into a marine coating, such as a marine coating comprising a film forming agent and solvent and optionally other ingredients. The solvent may be either organic solvent or water. The inhibitors of group II intron splicing of the invention are suitable for use in both solvent and water based marine coatings. Any conventional film forming agent may be utilized in the marine coating incorporating the inhibitors of the invention. Film-forming components may include polymer resin solutions. Non-limiting examples of polymer resins include unsaturated polyester resins formed from (a) unsaturated acids and anhydrides, such as maleic anhydride, fumaric acid, and itaconic acid; (b) saturated acids and anhydrides, such as phthalic anhydride, isophthalic anhydride, terephthalic anhydride, tetrahydrophthalic anhydride, tetrahalophthalic anhydrides, chlorendic acid, adipic acid, and sebacic acid; (c) glycols, such as ethylene glycol, 1,2 propylene glycol, dibromoneopentyl glycol, Dianol 33®, and Dianol 22®; and (d) vinyl monomers, such as styrene, vinyl toluene, chlorostyrene, bromostyrene, methylmethacrylate, and ethylene glycol dimethacrylate. Other suitable resins include, but are not limited to, vinyl ester-, vinyl acetate-, and vinyl chloride-based resins, vinyl chloride-vinyl acetate copolymer systems as aqueous dispersions or solvent based systems, mixtures of natural rosin and vinyl chloride-vinyl acetate copolymers, acrylic resins in solvent based or aqueous systems, urethane-based resins, self-polishing copolymer resins, ablative resins, leaching resins, elastomeric components, vulcanized rubbers, butadiene-styrene rubbers, butadiene-acrylonitrile rubbers, butadiene-styrene-acrylonitrile rubbers, drying oils such as linseed oil, asphalt, epoxies, siloxanes like for example polydimethylsiloxane, silanes like alkyl and aryl alkoxy silanes, silicones and silicone-based technologies like fluorosilicones, silicone acrylates, silicone latex elastomers, and combinations thereof.

The marine coating composition of the invention may include components in addition to inhibitors of group II intron splicing and a film-forming component, so as to confer one or more desirable properties, such as increased or decreased hardness, strength, increased or decreased rigidity, reduced drag, increased or decreased permeability, or improved water resistance. The selection of a particular component or group of components to impart such properties are within the capabilities of those having ordinary skill in the art. The marine coatings of the present invention may optionally contain one or more of the following: inorganic pigments, organic pigments or dyes, natural resins, such as rosin, fillers, extenders, swelling agents, wetting agents, coalescents, plasticizers, dispersants, surface active agents, preservatives, rheology modifiers or adhesion promoters, UV filters, and combinations thereof.

In some embodiments, the composition of the invention comprises a paint, sealant, solution, wax, spray, or the like, which comprises one or more inhibitors of group II intron splicing as described above.

The primary active ingredient for use in the present invention comprises at least inhibitor of group II intron splicing as described above. The percentage of inhibitor in the coating composition required for effective protection against biofouling organisms may vary substantially depending on the nature of the marine or freshwater structure to which the coating composition is applied, the service in which the structure is used, the pH of water and other environmental conditions to which the structure is exposed, depending on the inhibitor itself, the chemical nature of the film former, as well as other additives present in the composition that may influence the effectiveness of the inhibitor of group II intron splicing. The upper limit of activity may be also driven by characteristics of cost and toxicity that would be readily apparent to the skilled artisan. One skilled in the art would recognize that the amount of group II intron inhibitor could be reduced in the event a second active ingredient were present, so long as the combined composition is active as an antifoulant.

Also within the scope of this invention is any article, substrate, surface, or material having incorporated or having a surface coated, with a composition containing at least one inhibitor of group II intron splicing or derivative or salt or a combination thereof. The impregnated and/or coated articles of the invention can comprise any material that is in contact with fresh, salt, estuarine, brackish, sea or other bodies of water to which biofouling organisms are prone to attach, such as metal, wood, concrete, plastic, composite, and stone. Representative examples of articles which may benefit from a coating which inhibits attachment and growth of such organisms include boats and ships, for example their hulls, propellers, rudders, keels, centerboards, fins, hydrofoils, berthing facilities, such as piers and pilings, deck surfaces, buoys, wharves, jetties, fishing nets, industrial cooling system surfaces, cooling water intake, or discharge pipes, desalinization facilities, nautical beacons, floating beacons, floating breakwaters, docks, pipes, pipelines, tanks, water pipes in power stations, seaside industrial plants, fish preserving structures, aquatic constructions, port facilities, bridges, bells, plumbs, wheels, cranes, dredges, pumps, valves, wires, cables, ropes, ladders, pontoons, transponders, antennae, barges, periscopes, snorkels, gun mounts, gun barrels, launch tubes, mines, offshore rigging equipment, intake screens for water distribution systems and decorative or functional cement or stone formations.

In some embodiments, the composition described herein is used in a method to inhibit, treat and/or prevent growth of fungi, plants, algae, *Euglena* or other organisms that harbor an active group II intron. The method comprises administering an effective amount of an inhibitor of group II intron splicing to the organism.

Exemplary fungi identified as potential maritime biofouling pests include, but are not limited to, *Aspergillus niger, Aspergillus* sp., *Aspergillus versicolor, Fusarium solani, Paecilomyces lilacinus, Paecilomyces nivea, Paecilomyces spectabilis, Penicillium chrysogenum, Penicillium* sp., and *Trichoderma* sp.

Exemplary algae identified as potential maritime biofouling pests include, but are not limited to, members of the Divisions Chlorophyta (green algae), Chrysophyta (yeliow-green algae), Cyanophyta (blue-green algae or bacteria), Euglenophyta (euglenoides), Phaeophyta (brown algae), Xanthophyta (yellow-green algae), Pyrrophyta (fire algae), and Rhodophyta (red algae). Specific examples of algae include, but are not limited to, *Anabaena, Botryococcus braunii, Chlamydomonas reinhardii, Chlorella* sp., *Crypthecodinium cohnii, Cylindrotheca* sp., *Didymosphenia geminata, Dunaliella primolecta, Dunaliella tertiolecta, Euglena gracilis, Gracilaria Salicornia, Hydrodictyon reticulatum, Isochrysis galbana, Kappaphycus/Eucheuma, Lyngbya, Monallanthus salina, Nannochloris* sp., *Nannochloropsis salina, Neochloris oleoabundans, Nitzschia* sp., *Oscillatoria, Phaeodactylum tricornutum, Pithophora* spp., *Pleurochrysis carterae, Pylaiella littoralis, Scenedesmus dimorphus, Schizochytrium* sp; *Spirogyra* spp, *Spirulina* sp., *Tetraselmis* chuff, and *Tetraselmis suecica.*

Exemplary plants harboring group II introns include, but are not limited to, *Citrullus lanatus, Chaetosphaeridium globosum, Chlorokybus atmophyticus, Nicotiana tabacum, Marchantia polymorph, Oenothera, Pedinomonas minor, Spirodela oligorhiz, Zea mays, Hordeum vulgare, Sinapis alba, lathyrus sativus, Scenedesmus obliquus, Spinacia oleracea*, and *Triticum aestivum*. Further examples of pest water weeds include, but are not limited to, *Egeria densa* and *Ceratophyllum demersum.*

Pharmaceutical Compositions and Formulations

The invention also encompasses the use of pharmaceutical compositions of the invention or salts thereof to practice the methods of the invention. Such a pharmaceutical composition may consist of at least one inhibitor composition of the invention or a salt thereof in a form suitable for administration to a subject, or the pharmaceutical composition may comprise at least one inhibitor composition of the invention or a salt thereof, and one or more pharmaceutically acceptable carriers, one or more additional ingredients, or some combination of these. The compound or conjugate of the invention may be present in the pharmaceutical composition in the form of a physiologically acceptable salt, such as in combination with a physiologically acceptable cation or anion, as is well known in the art.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. In various embodiments, the composition comprises about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100% (w/w) active ingredient (e.g., inhibitor, etc.).

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, vagina or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents will be included, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. An exemplary preservative is a combination of about 0.5% to 2.0% benzyl alcohol and 0.05% to 0.5% sorbic acid.

In one embodiment, the composition includes an antioxidant and a chelating agent that inhibits the degradation of the compound. Antioxidants for some compounds include, but are not limited to, BHT, BHA, alpha-tocopherol and ascorbic acid in the range of about 0.01% to 0.3% (e.g., BHT in the range of 0.03% to 0.1% by weight by total weight of the composition). In one embodiment, the chelating agent is present in an amount of from 0.01% to 0.5% by weight by total weight of the composition. Chelating agents include, but are not limited to, edetate salts (e.g. disodium edetate) and citric acid in the weight range of about 0.01% to 0.20% by weight by total weight of the composition. The chelating agent is useful for chelating metal ions in the composition that may be detrimental to the shelf life of the formulation. While BHT and disodium edetate are an exemplary antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, (e.g., a mammal, including but not limited to, a human) may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily, or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, chewing gum, varnishes, sealants, oral and teeth "dissolving strips", or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In some embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another embodiment, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. In one embodiment, it should be present in an amount from about 0.0005% to about 5% of the composition. In one embodiment, it should be present in an amount of from about 0.001% to about 1% of the composition. Such compounds may be synthetically- or naturally derived.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Vaginal Administration

A pharmaceutical composition of the invention may be prepared, packaged, or sold in a formulation suitable for vaginal administration. With respect to the vaginal or perivaginal administration of the compounds of the invention, dosage forms may include vaginal suppositories, creams, ointments, liquid formulations, pessaries, tampons, gels, pastes, foams or sprays. The suppository, solution, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the exemplary embodiments of the present invention, and are not to be construed as limiting in any way the remainder of the disclosure.

Example 1: Small Molecules that Target Group II Intron RNA are Potent Antifungal Agents In this study, compound libraries were screened for small molecules that specifically inhibit the splicing of group II introns from yeast, and their activities were monitored in-vitro and in-vivo. The most promising scaffold compounds were optimized to yield a set of high affinity group II intron splicing inhibitors that are potent against the pathogenic yeast *C. parapsilosis*, and which are not toxic in mammalian cells. Given the unique RNA metabolism of fungi and yeast, these results demonstrate that RNA targeting may provide a much-needed approach for developing therapeutics against eukaryotic pathogens. These results also demonstrate that RNA tertiary structures can be targeted de-novo and that high affinity compounds can be identified using classical methods for developing pharmacologically active compounds. Given the vast number of physiologically important RNA tertiary structures that control gene expression in all domains of life, these results suggest a pathway for targeting these RNAs, resulting in a new generation of small molecule therapeutics.

The materials and methods employed in these experiments are now described.

Yeast Strains.

Strains of *Candida parapsilosis* (ATCC 22019) and *Saccharomyces cerevisiae* (ATCC 18824) were purchased from American Type Culture Collection (ATCC) and cultured according to the instructions from the manufacturer (ATCC). *S. cerevisiae* Wild-type (NP40-36a) and mtDNA intronless (XPM46) strains were provided (Perez-Martinez et al., 2003, EMBO J 22:5951-5961).

RNA Preparation.

Synthesis of the RNA Oligo Substrates.

RNA oligonucleotides containing 3'-terminal Black Hole Quencher 2 label and aminomodifier C6dT nucleotide (Glen Research) as well as U2-U6 RNA oligonucleotide (AGCAGUUCCCCUGCAUAAGGAUGAACCGCU (SEQ ID NO:19) were synthesized on a MerMade 12 DNA-RNA synthesizer (BioAutomation) using TBDMS phosphoramidites (Glen Research). Base deprotection was carried out in 3:1 mixture of 30% ammonium hydroxide (JT Baker) and ethanol at room temperature for 24 hours. Subsequent 2'-OH deprotection and purification on a 20% denaturing polyacrylamide gel were carried out as previously described (Wincott et al., 1995, Nucleic acids research, 23:2677-2684; Pyle and Green, 1994, Biochemistry, 33:2716-2725). RNA oligonucleotide U2-U6 was deprotected and purified as described (Wincott et al., 1995, Nucleic acids research, 23:2677-2684; Pyle and Green, 1994, Biochemistry, 33:2716-2725).

In Vitro Transcription.

Large-scale transcription of the SE, D1(Domain 1 in isolation), D3 (Domain 3 in isolation), D56 (RNA molecule containing both domains 5 and 6) and D135 RNAs (Su et al., 2005, Nucleic acids research, 33:6674-6687; Swisher et al., 2001, EMBO J, 20:2051-2061; Swisher et al., 2002, Journal of molecular biology, 315:297-310) was carried out using T7 RNA polymerase as previously described (Pyle and Green, 1994, Biochemistry, 33:2716-2725). Internally $^{32}$P-labeled ai5γ intron with short exons (SE RNA) (Zingler et al., 2010, Nucleic acids research, 38:6602-6609) was prepared by in vitro transcription as described (Pyle and Green, 1994, Biochemistry, 33:2716-2725; Daniels et al., 1996, Journal of molecular biology, 256:31-49). Internally labeled Azo-Pre-tRNA (Tanner et al., 1996, RNA 2:74-83) was in vitro transcribed and purified as previously described (Tanner et al., 1996, RNA 2:74-83). RNA molecules D3 and D56 were purified on an 8% denaturing polyacrylamide gel, and all other RNAs were purified on a 5% gel as previously described (Pyle and Green, 1994, Biochemistry, 33:2716-2725; Daniels et al., 1996, Journal of molecular biology, 256:31-49).

Fluorescent Labeling of RNA Oligonucleotides

Purified RNA oligonucleotides containing 3'-terminal Black Hole Quencher 2 label and aminomodifier C6dT nucleotide (Glen Research) were fluorescently labeled with the NHS ester of AlexaFluor 555 dye (Life Technologies Corp.) at the primary amino group located on the aminomodifier C6dT nucleotide. RNA oligonucleotides were dissolved in 200 µl of 0.25 M sodium bicarbonate buffer (pH 9.2) and then combined with a solution containing 0.5 mg of AlexaFluor 555 NHS ester in 200 µl formamide. The reaction was incubated at room temperature for 2 hours and the labelled products were purified on a 20% denaturing polyacrylamide gel.

High-Throughput Screening

High-throughput screening was carried out using a library of 10,000 compounds from the following collections: NCI Oncology (85 compounds), NCI Diversity (1356 compounds), ENZO kinase inhibitors (80 compounds), 640 FDA approved drugs, ENZO phosphatase inhibitors (33 compounds), BML-ENZO ion channel ligands (72 compounds), BML-metabotropic glutamatergic ligands (56 compounds), BML nuclear receptor ligands (76 compounds), protease inhibitors (53 compounds) and additional compounds from ChemBridge M W and ChemDiv to bring the total number of compounds to 10000.

The D135 ribozyme (Su et al., 2005, Nucleic Acids Res, 33:6674-6687), fluorescently labeled oligo substrate 17/2 DL (FIG. 1A-FIG. 1D) (both at 20 nM final concentrations in 50 mM MOPS, pH 7.0, 100 mM MgCl$_2$, 0.5M KCl), and the test compounds (final concentration of 10 µM in 50 mM MOPS, pH 7.0, 100 mM MgCl$_2$, 0.5M KCl) were aliquoted onto black non-binding 384-well plates (Corning 3757) using the multidrop combi (ThermoFisherScientific) and pintool (V & P Scientific). The reaction mixtures were incubated at 37° C. for 45 minutes, then the reaction was quenched with 100 mM EDTA and fluorescence intensity was analyzed on a Tecan Infinite multimode plate reader ($\lambda_{ex}$ 520 nm, $\lambda_{em}$ 560 nm, 5 nm bandwidth). Data were normalized to untreated wells and wells lacking the D135 ribozyme, and percent of inhibition was calculated using ActivityBase (IDBS). The Z'-factor was calculated as described (Zhang et al., 1999, J Biomol Screen, 4:67-73):

$$Z'=1-3\times(\sigma_p+\sigma n)/|\mu_p-\mu_n|,$$

where $\mu_p$ and $\sigma_n$ are mean value and standard deviation for the positive control (substrate only), and where $\mu_n$ and $\sigma_n$ are mean value and standard deviation for the negative control (no compound). The average Z'-factor from the screen was 0.83±0.03.

IC$_{50}$ Measurement for the Small Molecule Inhibition of the D135 Ribozyme Cleavage Reaction.

Black 96-well plates (Corning 3695) were filled with 50 µl of solution containing 20 nM D135 ribozyme, 20 nM double-labeled substrate 17/2 DL and small molecule inhibitor in 50 mM MOPS, pH 7.0, 100 mM MgCl$_2$ and 500 mM KCl. Small molecule inhibitors were tested at 19 different concentrations ranging from 5 nM to 1 mM. Plates were incubated at 37° C. for 10 minutes, then reaction mixtures were quenched with 100 mM EDTA and analyzed on the Synergy H1 plate reader (BioTek). Each experiment was performed in triplicate. Data were fit to a 4-parameter logistic function c+(d−c)/(1+(x/a)$^b$), where a is the IC$_{50}$, b is the slope parameter, c is the minimum response and d is the maximum response. Data are reported as average±s.e.m Determination of K$_i$ Values for Small Molecule Inhibition of the Self-Splicing Reaction.

Internally labeled SE RNA (2 nM) was incubated with various concentrations of inhibitor compound under near-physiological conditions (in 50 mM MOPS, pH 7.5, 8 mM MgCl$_2$, 100 mM KCl) at 30° C. Aliquots at different time points were quenched and analyzed on 5% denaturing polyacrylamide gel as previously described (Daniels et al., 1996, Journal of molecular biology, 256:31-49). Data were fit to a single-exponential equation to determine the first order rate constants (k$_{obs}$). The latter were then plotted against the concentration of the inhibitor and fit to the equation for non-competitive inhibition to determine $K_i$ values:

$$k_{obs}=k_{max}/(1+[I]/K_i),$$

where $k_{obs}$ and $k_{max}$ are the first order rate constants measured in the presence and in the absence of the inhibitor, respectively, [I] is the concentration of the inhibitor and Ki is the inhibition constant. Experiments were performed four times for API-014, three times for APY-090, Intronistat A, and Intronistat B and twice for the remaining compounds to ensure reproducibility. Data represent average±s.e.m.

Effect of Excess of Various RNAs on Splicing Inhibition.

Internally labeled SE RNA (2 nM final concentration) and unlabeled SE, D1, D3, D56 RNAs, yeast tRNA Phe and U2-U6 RNA oligo (2 μM final concentrations) were preincubated separately in 50 mM MOPS, pH 7.5, 100 mM KCl and 5 mM $MgCl_2$ (10 mM MgCl2 for the tRNA) at 30° C. for 20 minutes. Then the labeled SE RNA and competitor RNA solutions were mixed together with simultaneous addition of 19 (Intronistat B) (300 nM final concentration) to initiate the reaction. Reaction was carried out under near-physiological conditions (in 50 mM MOPS, pH 7.5, 8 mM $MgCl_2$, 100 mM KCl) at 30° C. Aliquots at different time points were quenched and analyzed on an 5% denaturing polyacrylamide gel as previously described (Daniels et al., 1996, J Mol Biol, 256:31-49). Data were fit with a single-exponential equation to determine the first order rate constants ($k_{obs}$). Experiments were performed in triplicate to ensure reproducibility.

Testing Reversibility of Compound Binding.

To examine reversibility of compound binding, the splicing reaction was initiated at high concentration (2 μM) of the indicated inhibitor, allowed to react for an hour under near physiological conditions (see above), and then diluted by 10-fold with reaction buffer. Aliquots at different time points were quenched and analyzed on an 5% denaturing polyacrylamide gel as previously described (Daniels et al., 1996, J Mol Biol, 256:31-49). Splicing efficiency was observed to significantly increase upon dilution of the inhibitor, with a change in rate that is commensurate with the reduction in compound concentration, indicating that binding of the inhibitors to the intron RNA is reversible (FIG. 25D). Experiments were performed in duplicate to ensure reproducibility.

Inhibition of Group I Intron Splicing.

Splicing of the Azo-Pre-tRNA intron was carried out essentially as previously described (Tanner et al., 1996, RNA 2:74-83). Internally labeled Azo-Pre-tRNA (20 nM) was incubated in 25 mM HEPES, pH 7.5, 10 mM $MgCl_2$ at 50° C. for 10 minutes, and then at 32° C. for 2 minutes. Then Intronistat B was added to the final concentration of 1, 5, 10, 20, 50 and 10011M and reaction was initiated by addition of 100 μM GTP (final concentration). The final concentration of DMSO in all samples was 10%. Aliquots at different time points were quenched and analyzed on an 5% denaturing polyacrylamide gel as previously described (Tanner et al., 1996, RNA 2:74-83; Daniels et al., 1996, J Mol Biol, 256:31-49)). All experiments were performed in triplicate to ensure reproducibility. Data represent average±s.e.m.

Yeast Respiration Assay in S. cerevisiae.

Yeast respiration assays were conducted either in liquid YPD media (BD Bacto Yeast Extract, BD Bacto Peptone, 2% glucose) or in YPGE media (BD Bacto Yeast Extract, BD Bacto Peptone, 3% glycerol, 3% ethanol), essentially as described for the antifungal MIC assays (see below). To initiate these experiments, 100 μl of a fresh stock solution was prepared for each compound (3.2 mg/ml for Amphotericin B and 12.8 mg/ml for each test compounds) in DMSO. This concentrated stock solution was placed in the first well of 12-well row on a 96-well plate. The subsequent nine wells in this row contained 50 μl of DMSO for serial dilution. From the first well, 50 μl of the compound stock was withdrawn, transferred to the second well and mixed. This process was repeated from the second and subsequent wells, resulting in a 1:2 serial dilution of the stock into DMSO. Wells 11 and 12 contained DMSO only, to be used as no compound control and sterility control, with no inoculum added, respectively. After preparing this plate, 2.5 μl from each of the 12 wells was transferred to the wells of a separate 96-well plate, each of which contained 122.5 μl of YPD or YPGE medium, resulting in a set of serial dilutions of compound into growth media in a volume of 125 μl. Then 50 μl from each of these dilutions were transferred onto a third 96-well plate (the assay plate) and mixed with an equal volume (50 μl) of freshly prepared yeast inoculum in YPD or YPGE medium set to provide $0.5\times10^3$ to $2.5\times10^3$ colony forming units per 1 mL (wells 1-11), or YPD/YPGE alone (sterility control, well 12). The final compound concentration range of the assay was 0.25-128 μg/ml for test compounds and 0.0625-32 μg/ml for Amphotericin B. The final concentration of DMSO was 1%. Plates were incubated at 30° C. and visually analyzed for turbidity after 24 and 48 hours of incubation. The lowest compound concentration at which no growth was apparent is reported as the MIC (Table 1). All experiments were performed in triplicate.

TABLE 1

MIC of candidate compounds.

| Compound | MIC in YPD (glucose), μg/ml | MIC in YPGE (glycerol), μg/ml |
|---|---|---|
| APY-019 | >128 | 64 |
| APY-014 | >128 | >128 |
| APY-081 | >128 | 32 |
| APY-084 | >128 | 16-32 |
| APY-090 | >128 | 64 |
| APY-093 | >128 | >128 |
| APY-101 (Intronistat A) | >128 | 32 |
| NED-2020 (Intronistat B) | >128 | 64 |
| Amphotericin B | 2 | 16 |

S. cerevisiae Growth Assays

Cultures of S. cerevisiae (Wild-type: NP40-36a, mtDNA intronless: XPM46 (Perez-Martinez et al., 2003, EMBO J, 22:5951-5961) were grown overnight with shaking to mid-log phase in YPGE at 30° C. Equal numbers of cells were harvested and serially-diluted 1:5. Cells were then plated on YPD or YPGE media containing DMSO or Intronistat A dissolved in DMSO (final concentration: 64 or 128 μg/mL). Plates were grown for one day (YPD plates), two days (YPGE DMSO plate), or 18 days (YPGE 18 (Intronistat A) plate) at 30° C. Experiment was replicated twice to ensure reproducibility of growth phenotype.

Analysis of Group II Intron Splicing in S. cerevisiae by RT-qPCR.

A culture of S. cerevisiae was grown overnight with shaking in YPGE at 30° C. The saturated culture was then diluted and grown to mid-log phase in YPGE. Equal volumes of DMSO or compounds dissolved in DMSO were added to individual cultures (final concentrations of NED-2020: 64 μg/mL, APY-101: 32 μg/mL, APY-081: 32 μg/mL, APY-014: 64 μg/mL, Amphotericin B: 8 μg/mL), and incubated for four hours. Cells were harvested by centrifugation, washed with 500 µL ice-cold MilliQ water, centrifuged again, and snap-frozen in liquid nitrogen. Total RNA was isolated using E.Z.N.A. Yeast Purification Kit (Omega Biotek) according to manufacturer's procedures. The RNA was eluted in 50 µL of RNase/DNase-free water (ThermoFisher), followed by DNAse treatment with RQ1 DNase (Promega), for 1 hour at 37° C. Then it was mixed with 6 µl of 3M NaOAc and precipitated with 75% EtOH at −20° C. overnight. Then the RNA was reverse-transcribed with SuperScript III (ThermoFisher) following manufacturer's recommendations with 200 ng Random Hexamer Primers (ThermoFisher) and RNasin (ThermoFisher) in a 20 µl reaction. After reverse transcription, RNA was degraded by addition of 2N NaOH (2 µl) and incubation at 95° C. for 5 minutes. After cooling on ice for 5 minutes, 2 µl of 1M HCl and 2 µl of 3M NaOAc were added to the reaction mixture, and cDNA was precipitated with 75% EtOH at −20° C. for 30 minutes and resuspended in RNase/DNase-free water. The cDNA levels were quantified with real-time PCR using LightCycler 480 SYBR Green I (Roche) and a CFX384 Real-Time PCR Detection System (Bio-Rad) in triplicate. Relative levels of indicated RNA species from different conditions were normalized according to the $\Delta\Delta C_T$ method via the following equation (Livak and Schmittgen, 2001, Methods, 25:402-408):

$$\Delta\Delta C_T = [(C_T COX1\text{total or unspliced} - C_T ACT1 \text{ or } PGK1)\text{test compound} - (C_T COX1\text{total or unspliced} - C_T ACT1 \text{ or } PGK1)\text{DMSO})].$$

The average and SEM of $2\char`\^-\Delta\Delta C_T$ is reported for each sample from three independent replicates. The following primer sets were used to amplify indicated targets: ACT1: TCGAACAAGAAATGCAAACCG (SEQ ID NO:1), GGCAGATTCCAAACCCAAAAC (SEQ ID NO:2); PGK1: TGTCTTGGCTTCTCACTTGG (SEQ ID NO:3), TTCAACTTCTGGACCGACAC (SEQ ID NO:4); Total COX1: TGGTATGCCTAGAAGAATTCCTG (SEQ ID NO:5), AGAATAATGATAATAGTGCAATGAATGAAC (SEQ ID NO:6); Unspliced COX1: CTTACTACGTGGTGGGACATT (SEQ ID NO:7), GTCATTACAGCTTAGCATATTTATGT (SEQ ID NO:8). In the course of analysis, no reverse transcription control samples displayed minimal signal, indicating that amplicons were amplified from cDNA and not genomic DNA, and gel electrophoresis confirmed amplification of the intended amplicon.

Analysis of Group II Intron Splicing in C. parapsilosis by qRT-PCR.

A culture of C. parapsilosis was grown overnight with shaking in RPMI at 30° C. The saturated culture was then diluted and grown to mid-log phase in RPMI. Equal volumes of DMSO or compounds dissolved in DMSO were added to individual cultures (final concentrations of Intronistat B and 4: 32 µg/mL) and incubated for two hours. Potassium cyanide (KCN), an inhibitor of complex IV of the electron transport chain, was added to a final concentration of 10 mM for an additional two hours to induce nascent COX1 expression. Cells were harvested, RNA prepared and reverse-transcribed, and cDNA quantified as in S. cerevisiae experiments. The mean and s.e.m. of $2\char`\^-DDCT$ is reported for each sample from three independent replicates. The following primer sets were used to amplify indicated targets:

C.p.PGK1:
(SEQ ID NO: 13)
TGGATGGGTCTTGATTGTGG, (SEQ ID NO: 14)
GTCAAATTCAAAGACACCCGG;

total C.p.COX1:
(SEQ ID NO: 15)
GGTGCTGTAGATATGGCATTTG, (SEQ ID NO: 16)
GCACTAATTGATGATAGTGGAGGA;

unspliced C.p.COX1:
(SEQ ID NO: 17)
TGTTCTTGTTACTGGTCATGCT, (SEQ ID NO:18)
AGCACTTACTAACTGTTCACGTC.

Determination of MICs for the Small Molecule Inhibitors Against C. parapsilosis

Minimal inhibitory concentrations (MICs) for C. parapsilosis were determined in a final volume of 100 µl. Fresh stock solutions of control antifungal drugs (Amphotericin B and Itraconazole) and of test compounds were prepared at 3.2 mg/ml and at 12.8 mg/ml respectively in DMSO. After placing the stock in the first well, solutions of test compounds and antifungal controls were serially diluted 1:2 with DMSO into the first nine successive wells of a 12-well row on a 96-well plate (as described above). After dilution, 2.5 µl from each of these 10 wells were transferred onto a separate 96-well plate and diluted with 122.5 µl of RPMI-1640 medium (Sigma). Wells 11 and 12 contained 2.5 µl DMSO and 122.5 µl of RPMI-1640 as a positive growth control (no compound) and sterility control (no inoculum added). A 50 µl volume was taken from each of the RPMI dilutions (wells 1-12) and transferred to the wells of a third 96-well plate (assay plate), where they were mixed with an equal volume (50 µl) of freshly prepared inoculum of C. parapsilosis in RPMI-1640 medium, set at a density to provide the $0.5 \times 10^3$ to $2.5 \times 10^3$ colony forming units per 1 mL (except for the sterility control). Sterility control was mixed with 50 µl of sterile medium.

The final concentration range of the assay was 0.25-128 µg/ml for test compounds and 0.0625-32 µg/ml for Amphotericin B and Itraconazole. The final concentration of DMSO was 1%. The assay plate was incubated at 35° C. or 37° C. and visually analyzed for turbidity after 24 and 48 hours of incubation. The lowest compound concentration at which no growth was apparent is reported as the MIC. All experiments were performed in triplicate.

Cytotoxicity in HEK-293T Cells.

HEK-293T cells were cultured in Dulbecco's Modified Eagle's Medium (DMEM) (Gibco) supplemented with 10% Fetal Bovine Serum (FBS, Gibco) and 100 U/ml of Penicillin-Streptomycin (Gibco) at 37° C. and 5% $CO_2$. For the cytotoxicity experiments, cells were aliquoted into black 96-well plates with a clear bottom (Corning 3603) at a concentration of 10,000 cells per well. The cells were grown at 37° C., 5% $CO_2$ for 5-6 hours, then the medium was replaced with the same medium without FBS and cells were grown at 37° C., 5% $CO_2$ for 24 hours. Freshly prepared stock solutions of test compounds (12.8 mg/ml in DMSO) were serially diluted 1:2 with DMSO into the first 11 successive wells of a 12-well row on a 96-well plate as described above. Well 12 was used as a growth control (no compound). After dilution, 1 µl from each well of the compound plate was added to the plate containing cells (the assay plate), and cells were incubated at 37° C., 5% $CO_2$ for another 24 hours. After incubation, cell viability was determined using the luminescent Cell Titer Glo cell viability assay (Promega), in which 100 µl of the assay reagent was added to each well of the assay plate. After gentle shaking for 7-10 minutes, the plates were analyzed on a Synergy H1 plate reader (BioTek). Luminescence was plotted against the compound concentration and $IC_{50}$ values were determined by fitting the data to a 4-parameter logistic function $c+(d-c)/(1+(x/a)^b)$, where a is the $IC_{50}$, b is the slope parameter, c is the minimum response and d is the maximum response. Experiments were replicated to ensure reproducibility.

Statistics and Reproducibility

The following reported data represent average of n=3 independent experiments: all $IC_{50}$ values for ribozyme cleavage, Ki values for compounds APY-090, Intronistat A and Intronstat B, $k_{obs}$ values for inhibition of splicing in the presence of the excess of various RNAs, time courses for inhibition of the group I intron splicing, DDCT values obtained from qRT-PCR analysis of group II intron splicing in C. parapsilosis, MIC values from yeast respiration assay, MIC values for small molecules against C. parapsilosis, $IC_{50}$ values for cytotoxicity in HEK-293T cells for compounds CAS 3260-50-2, APY-019, APY-083, APY-077, APY-084, APY-090, APY-094 and APY-097. The following reported data represent average of n=4 independent experiments: Ki for APY-014, DDCT values obtained from qRT-PCR analysis of group II intron splicing in S. cerevisiae, $IC_{50}$ values for cytotoxicity in HEK-293T cells for compounds APY-007, APY-014, APY-098, APY-024, APY-068, APY-093, APY-081, APY-091, Intronistat A and Intronstat B. The following experiments were repeated twice to ensure reproducibility: test of reversibility of compound binding, S. cerevisiae growth assays, cytotoxicity of APY-001 in HEK-293T cells, Ki determination for compounds CAS 3260-50-2, APY-007, APY-001, APY-098, APY-019, APY-024, APY-083, APY-068, APY-077, APY-093, APY-081, APY-084, APY-091, APY-094 and APY-097. All values are reported as mean±s.e.m.

Synthesis of Small Molecules

Unless otherwise stated, all reagents were purchased from commercial suppliers and used without further purification. Analytical thin layer chromatography (TLC) was performed on Merck Millipore precoated (0.25 mm thickness) silica gel plates containing F254 indicator. Visualization was accomplished by irradiation with UV light at 254 nm or PMA or $KMnO_4$ stain solution. Flash column chromatography was performed on SiliaFlash® F60 silica gel (40-63 µm) supplied by Silicycle. All $^1H$ NMR spectra were recorded on an Agilent DD2 400 MHz spectrometer (400 MHz) in deuterated solvent and $^{13}C$ NMR spectra were recorded on an Agilent DD2 600 MHz spectrometer (151 MHz) in deuterated solvent. LCMS were run using an Advion Expression® mass spectrometer with an Agilent Technologies 1260 Infinity® liquid chromatograph front end.

General Procedure for the Removal of Benzyl Groups from 3,4,5-Tribenzyloxybenzenes (Procedure A)

A cooled (−70° C.) stirred solution of tribenzyloxybenzene (0.25 mmol) in anhydrous DCM (5 mL) under nitrogen was treated dropwise with 1N $BBr_3$/DCM (1.5 mL, 1.5 mmol), allowed to warm to room temperature and stirred at room temperature for 4 hours, then recooled (−60° C.). The mixture was quenched dropwise with methanol (5 mL), warmed to room temperature, stirred for 30 minutes, then concentrated in vacuo.

Preparation of 2-Benzoylbenzofurans

5-Bromobenzofuran-3-yl)(3,4,5-tris(benzyloxy)phenyl)methanone (Intermediate 1)

Figure 2:
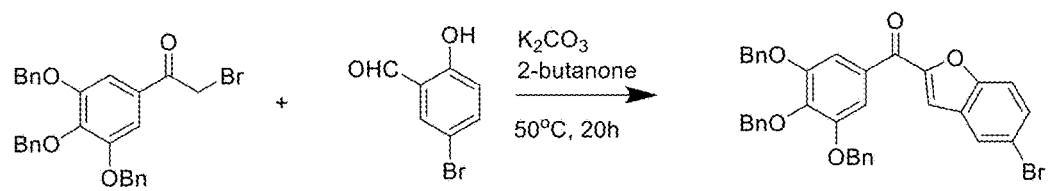
FIG. 2 depicts a chemical reaction diagram of the synthesis of 5-Bromobenzofuran-3-yl)(3,4,5-tris(benzyloxy)phenyl)methanone.

A stirred suspension of potassium carbonate (1.04 g, 7.5 mmol) in 2-butanone (10 mL) under nitrogen was treated with a solution of 5-bromosalicylaldehyde (1.01 g, 5 mmol) in 2-butanone (10 mL) and stirred for 15 minutes. A solution of 2-bromo-1-(3,4,5-tris(benzyloxy)phenyl)ethan-1-one (2.59 g, 5 mmol) in 2-butanone (30 mL) was added, and the mixture heated to 50° C. for 20 hours, cooled to room temperature, and diluted with water (150 mL). The aqueous suspension was stirred a few minutes, filtered, and the filter cake rinsed with water and dried in vacuo to afford 3.02 g (97%) of (5-bromobenzofuran-3-yl)(3,4,5-tris(benzyloxy)phenyl)methanone as a pale tan voluminous solid (FIG. 2). $^1H$ NMR ($CDCl_3$): δ 7.76 (d, J=2 Hz, 1H), 7.55 (dd, J=9 Hz, 2 Hz, 1H), 7.45 (m, 3H), 7.35-7.43 (m, 10H), 7.27-7.32 (m, 5H), 5.21 (s, 2H), 5.19 (s, 4H). $^{13}C$ NMR ($CDCl_3$): δ 182.61, 154.44, 152.64, 152.46, 142.82, 137.29, 136.62, 131.62, 131.14, 128.77, 128.68, 128.56, 128.26, 128.08, 128.06, 127.33, 125.75, 116.88, 115,04, 114.01, 109.38, 75.23, 71.15. LCMS m/z: $[M+H]^+$ 620.2 (20%).

Benzofuran-2-yl(3,4,5-trihydroxyphenyl)methanone (APY-068)

Figure 3:
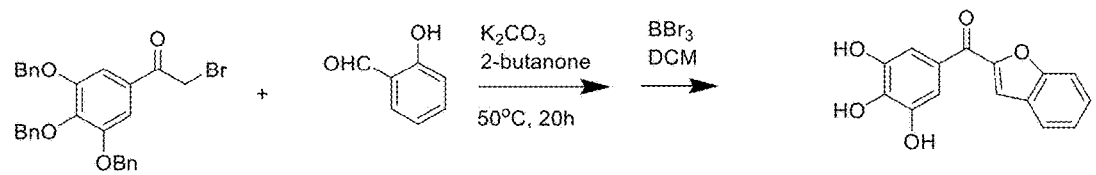
FIG. 3 depicts a chemical reaction diagram of the synthesis of Benzofuran-2-yl(3,4,5-trihydroxyphenyl)methanone (APY-068).

A stirred suspension of potassium carbonate (100 mg, 0.724 mmol) in 2-butanone (1 mL) under nitrogen was treated with a solution of salicylaldehyde (61 mg, 0.50 mmol) in 2-butanone (1 mL) and stirred 15 minutes. A solution of 2-bromo-1-(3,4,5-tris(benzyloxy)phenyl)ethan-1-one (259 mg, 0.5 mmol) in 2-butanone (3 mL) was added, and the mixture heated to 50° C. for 20 hours, cooled to room temperature, and diluted with water (15 mL). The mixture was extracted with ethyl acetate (40 mL, then 2×15 mL) and the combined organic solution was washed with water and brine (25 mL each), dried ($MgSO_4$) and concentrated in vacuo. The residual solid was dissolved in heptane/dichloromethane and loaded onto a silica gel column and eluted with 60% DCM/heptane, then 80% DCM/heptane, then DCM to afford 223 mg (83%) of tribenzyloxy penultimate intermediate as a white solid. This compound (200 mg, 0.37 mmol) was taken directly through Procedure A to afford the crude product, which was dissolved in dichloromethane containing a little ethyl acetate, loaded onto a silica gel column (~60 cc), and eluted with 2:1 DCM/ethyl acetate to afford 44 mg (44%) of benzofuran-2-yl(3,4,5-trihydroxyphenyl)methanone as a pale orange solid (FIG. 3). $^1H$ NMR (d6-acetone): δ 8.38 (br s, 2H), 8.27 (br s, 1H), 7.84 (d, J=8 Hz, 1H), 7.67 (d, J=8 Hz, 1H), 7.63 (s, 1H), 7.53 (t, J=7.5 Hz, 1H), 7.37 (t, J=7.5 Hz, 1H), 7.28 (s, 2H). $^{13}C$ NMR (d4-acetic acid): δ 181.78, 155.52, 152.79, 145.33, 138.50, 128.16, 127.80, 127.20, 123.83, 123.29, 114.77, 111.99, 109.38. LCMS m/z: $[M-H]^-$ 269.7 (100%).

5-[(5,7-Dichloro-1-benzofuran-2-yl)carbonyl]benzene-1,2,3-triol (APY-083)

Figure 4:
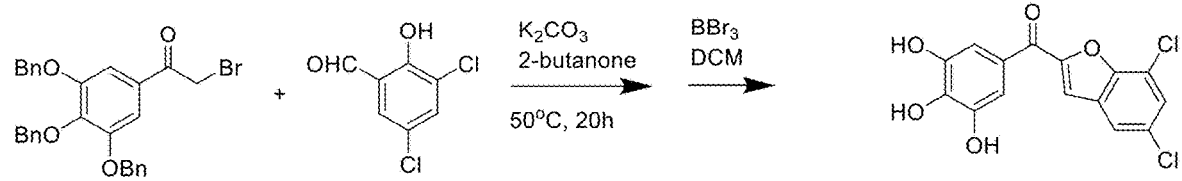
FIG. 4 depicts a chemical reaction diagram of the synthesis of 5-[(5,7-Dichloro-1-benzofuran-2-yl)carbonyl]benzene-1,2,3-triol (APY-083).

A stirred suspension of potassium carbonate (100 mg, 0.724 mmol) in 2-butanone (1 mL) under nitrogen was treated with a solution of 3,5-dichlorosalicylaldehyde (95.5 mg, 0.50 mmol) in 2-butanone (1 mL) and stirred 15 minutes. A solution of 2-bromo-1-(3,4,5-tris(benzyloxy)phenyl)ethan-1-one (259 mg, 0.5 mmol) in 2-butanone (3 mL) was added, and the mixture heated to 50° C. for 20 hours, cooled to room temperature, and diluted with water (15 mL). The aqueous suspension was stirred a few minutes, filtered, and the filter cake rinsed with water and dried to afford 284 mg (92%) of a pale tan solid which was taken forward without purification. A cooled (−70° C.) stirred solution of this penultimate intermediate (284 mg, 0.466 mmol) in anhydrous DCM (8 mL) under nitrogen was subjected to Procedure A with 1N BBr3/DCM (2.8 mL, 2.8 mmol), and the resultant dark solid was dissolved in 10% methanol/DCM, loaded onto a small silica column (~40 cc) and eluted with 10% methanol/DCM to afford a brown solid, which was triturated from cold DCM to afford 95 mg (60%) of 5-[(5,7-dichloro-1-benzofuran-2-yl)carbonyl]benzene-1,2,3-triol as a gray solid (FIG. 4). $^1$H NMR (d6-acetone): δ 8.45 (br s, 2H), 8.39 (br s, 1H), 7.88 (d, J=2 Hz, 1H), 7.68 (s, 1H), 7.65 (d, J=2 Hz, 1H), 7.28 (s, 2H). $^{13}$C NMR (d6-acetone): δ 181.13, 154.48, 149.86, 145.44, 139.01, 129.86, 129.07, 127.58, 127.10, 121.69, 117.77, 114.38, 109.48. LCMS m/z: [M−H]$^−$ 336.5 (100%), 338.5 (70%).

5-{[5-(4-Methylpyridin-3-yl)-1-benzofuran-2-yl]carbonyl}benzene-1,2,3-triol (APY-081)

Figure 5:
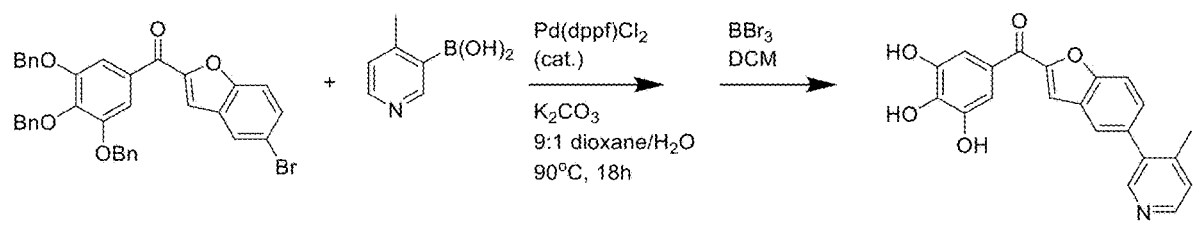
FIG. 5 depicts a chemical reaction diagram of the synthesis of 5-{[5-(4-Methylpyridin-3-yl)-1-benzofuran-2-yl]carbonyl}benzene-1,2,3-triol (APY-081).

A stirred mixture of (5-bromobenzofuran-3-yl)(3,4,5-tris(benzyloxy)phenyl)methanone (186 mg, 0.30 mmol), 4-methylpyridine-3-boronic acid (58 mg, 0.42 mmol) and potassium carbonate (166 mg, 1.2 mmol) in 9:1 dioxane/water (3 mL) in a pressure tube was degassed over 20 minutes with argon, then treated with 1,1-bis(diphenylphosphino)ferrocene dichloropalladium (II) (25 mg, 0.034 mmol), capped, and heated to 90° C. for 18 hours and cooled to room temperature and diluted with ethyl acetate (12 mL). The mixture was combined with water (10 mL) and separated. The aqueous solution was extracted with ethyl acetate (8 mL) and the combined organic solution was washed with brine (15 mL), dried (MgSO4) and concentrated in vacuo. The dark residue was dissolved in DCM and loaded onto a silica gel column (~75 cc) and eluted with 20%, then 25% EtOAc/DCM to afford 160 mg (84%) of the penultimate intermediate as a pale yellow viscous oil. A cooled (−70° C.) stirred solution of this compound (160 mg, 0.253 mmol) in anhydrous DCM (5 mL) under nitrogen was subjected to Procedure A with 1N BBr3/DCM (1.5 mL, 1.5 mmol), and the resultant tan solid was triturated from acetonitrile, collected, and dried in vacuo to afford 91 mg (99%) of 5-{[5-(4-methylpyridin-3-yl)-1-benzofuran-2-yl]carbonyl}benzene-1,2,3-triol as a pale tan solid (FIG. 5). $^1$H NMR (d6-DMSO): δ 9.40 (br s, 3H), 8.83 (s, 1H), 8.79 (d, J=6 Hz, 1H), 8.01 (d, J=6 Hz, 1H), 7.97 (m, 1H), 7.92 (d, J=8.5 Hz, 1H), 7.73 (br s, 1H), 7.65 (dd, J=8.5 Hz, 2 Hz, 1H), 7.09 (s, 2H), 2.50 (s, 3H). $^{13}$C NMR (d6-DMSO): δ 182.07, 156.49, 155.28, 153.35, 146.19, 142.34, 140.91, 139.98, 139.86, 130.72, 129.68, 128.49, 127.64, 126.95, 124.95, 115.38, 113.01, 109.57, 21.23. LCMS m/z: [M−H]$^−$ 360.0 (100%). LCMS m/z: [M+H]$^+$ 362.0 (100%).

5-({5-[4-(Hydroxymethyl)phenyl]-1-benzofuran-2-yl}carbonyl)benzene-1,2,3-triol (APY-084)

Figure 6:
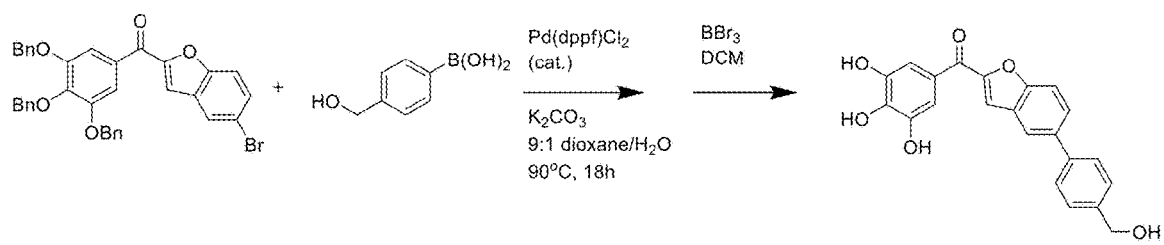
FIG. 6 depicts a chemical reaction diagram of the synthesis of 5-({5-[4(Hydroxymethyl)phenyl]-1-benzofuran-2-yl}carbonyl)benzene-1,2,3-triol (APY-084).

A stirred mixture of (5-bromobenzofuran-3-yl)(3,4,5-tris(benzyloxy)phenyl)methanone (248 mg, 0.40 mmol), 4-hydroxymethylphenylboronic acid (85 mg, 0.56 mmol) and potassium carbonate (221 mg, 1.6 mmol) in 9:1 dioxane/water (4 mL) in a pressure tube was degassed over 20 minutes with argon, then treated with 1,1-bis(diphenylphosphino)ferrocene dichloropalladium (II) (33 mg, 0.045 mmol), capped, and heated to 90° C. for 18 hours and cooled to room temperature and diluted with ethyl acetate (12 mL). The mixture was combined with water (10 mL) and separated. The aqueous solution was extracted with ethyl acetate (8 mL) and the combined organic solution was washed with brine (15 mL), dried (MgSO4) and concentrated in vacuo. The dark residue was dissolved in DCM and loaded onto a silica gel column (~75 cc) and eluted with 3%, then 5% EtOAc/dichloromethane to afford 183 mg (71%) of the penultimate intermediate as a white solid. A cooled (−70° C.) stirred solution of this compound (174 mg, 0.269 mmol) in anhydrous DCM (5 mL) under nitrogen was subjected to Procedure A with 1N BBr3/DCM (2.15 mL, 2.15 mmol), and the resultant solid dissolved in 9:1 DCM/methanol and added to a silica gel column (~70 cc). The column was eluted with 9:1 DCM/methanol to afford a brown solid, which was triturated from DCM and dried to afford 70 mg (69%) of 5-({5-[4-(hydroxymethyl)phenyl]-1-benzofuran-2-yl}carbonyl)benzene-1,2,3-triol as a yellow-tan solid (FIG. 6). $^1$H NMR (d6-acetone): δ 8.38 (br s, 3H), 8.11 (d, J=1.5 Hz, 1H), 7.85 (dd, J=9 Hz, 1.5 Hz, 1H), 7.66-7.79 (m, 4H), 7.59 (d, J=8 Hz, 2H), 7.30 (s, 2H), 4.72 (s, 2H), 3.14 (br s, 1H). $^{13}$C NMR (d6-acetone): δ 182.30, 155.25, 153.38, 145.39, 140.70, 137.37, 136.61, 129.65, 127.80, 127.58, 127.36, 127.30, 121.28, 115.17, 112.23, 109.18, 99.32, 32.98. LCMS m/z: [M−H]$^−$ 374.9 (50%).

5-[(5-{4-[(Diethylamino)methyl]phenyl}-1-benzofuran-2-yl)carbonyl]benzene-1,2,3-triol hydrobromide (APY-090)

Figure 7:
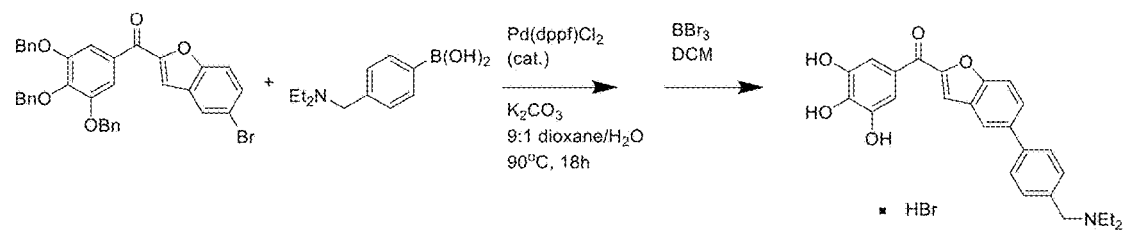
FIG. 7 depicts a chemical reaction diagram of the synthesis of 5-[(5-{4-[(Diethylamino)methyl]phenyl}-1-benzofuran-2-yl)carbonyl]benzene-1,2,3-triol hydrobromide (APY-090).

A stirred mixture of (5-bromobenzofuran-3-yl)(3,4,5-tris(benzyloxy)phenyl)methanone (186 mg, 0.30 mmol), diethyl({[4-(tetramethyl-1,3,2-dioxaborolan-2-yl)phenyl]methyl})amine (122 mg, 0.42 mmol) and potassium carbonate (166 mg, 1.2 mmol) in 9:1 dioxane/water (3 mL) in a pressure tube was degassed over 20 minutes with argon, then treated with 1,1-bis(diphenylphosphino)ferrocene dichloropalladium (II) (25 mg, 0.034 mmol), capped, and heated to 90° C. for 18 hours and cooled to room temperature and diluted with DCM (12 mL) and filtered through Celite®. The residual dark oil was dissolved in ethyl acetate and loaded onto a silica gel column (~50 cc) and eluted with EtOAc, then 5% methanol/EtOAc to afford 187 mg (89%) of the penultimate intermediate as an amber solid. A cooled (−70° C.) stirred solution of this compound (187 mg, 0.266 mmol) in anhydrous DCM (5 mL) under nitrogen was subjected to Procedure A with 1N BBr3/DCM (1.6 mL, 1.6 mmol), and the resultant solid triturated from DCM to afford 100 mg (73%) of 5-[(5-{4-[(diethylamino)methyl]phenyl}-1-benzofuran-2-yl)carbonyl]benzene-1,2,3-triol hydrobromide as a tan solid (FIG. 7). $^1$H NMR (d6-DMSO): δ 9.20-9.50 (m, 3H), 7.80-8.20 (m, 4H), 7.62-7.70 (m, 2H), 7.38-7.55 (m, 2H), 7.09 (br s, 2H), 4.36 (d, J=6 Hz, 1H), 4.20-4.30 (m, 1H), 2.97-3.17 (m, 4H), 1.15-1.30 (m, 6H). $^{13}$C NMR (d6-DMSO): δ 182.11, 155.20, 153.19, 146.18, 141.42, 139.88, 135.97, 132.33, 132.16, 129.60, 127.99, 127.83, 127.06, 121.93, 115.70, 113.11, 109.53, 54.95, 46.35, 8.84. LCMS m/z: [M−H]$^−$ 429.7 (100%). LCMS m/z: [M+H]$^+$ 431.7 (100%).

N,N-Diethyl-4-{2-[(3,4,5-trihydroxyphenyl)carbonyl]-1-benzofuran-5-yl}benzamide (APY-091)

Figure 8:
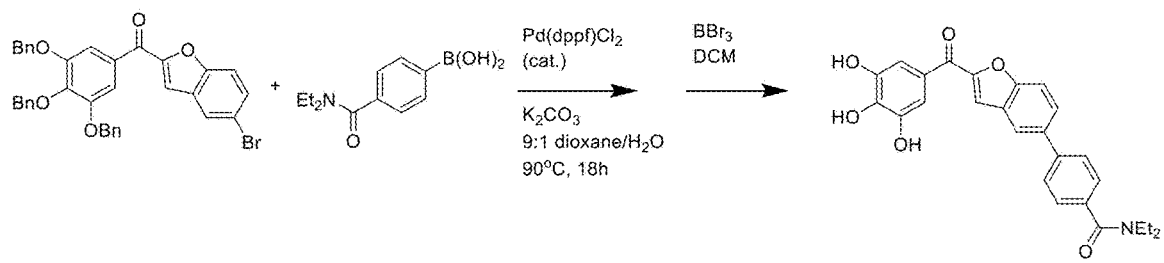
FIG. 8 depicts a chemical reaction diagram of the synthesis of N,N-Diethyl-4-{2-[(3,4,5-trihydroxyphenyl)carbonyl]-1-benzofuran-5-yl}benzamide (APY-091).

A stirred mixture of (5-bromobenzofuran-3-yl)(3,4,5-tris(benzyloxy)phenyl)methanone (186 mg, 0.30 mmol), [4-(diethylcarbamoyl)phenyl]boronic acid (93 mg, 0.42 mmol) and potassium carbonate (166 mg, 1.2 mmol) in 9:1 dioxane/ water (3 mL) in a pressure tube was degassed over 20 minutes with argon, then treated with 1,1-bis(diphenylphosphino)ferrocene dichloropalladium (II) (25 mg, 0.034 mmol), capped, and heated to 90° C. for 18 hours and cooled to room temperature and diluted with DCM (12 mL) and filtered through Celite®. The residual dark oil was dissolved in DCM and loaded onto a silica gel column (~75 cc) and eluted with 5% EtOAc/DCM, then 10% EtOAc/DCM to afford 167 mg (78%) of the penultimate intermediate as a pale amber solid. A cooled (−70° C.) stirred solution of this compound (167 mg, 0.233 mmol) in anhydrous DCM (5 mL) under nitrogen was subjected to Procedure A with 1N BBr3/DCM (1.85 mL, 1.85 mmol), and the resultant dark solid was dissolved in 9:1 DCM/methanol and loaded onto silica gel (~40 cc) and eluted with DCM, then 9:1 DCM/methanol to afford 69 mg (66%) of N,N-diethyl-4-{2-[(3,4,5-trihydroxyphenyl)carbonyl]-1-benzofuran-5-yl}benzamide as a brown glassy solid (FIG. 8). $^1$H NMR (d6-DMSO): δ 9.36 (br s, 3H), 8.12 (s, 1H), 7.83 (br s, 2H), 7.74 (d, J=7.5 Hz, 2H), 7.69 (br s, 1H), 7.43 (d, J=7.5 Hz, 2H), 7.10 (br s, 2H), 3.10-3.50 (m, 4H), 1.09 (m, 6H). $^{13}$C NMR (d6-DMSO): δ 182.14, 170.12, 155.16, 153.14, 146.20, 140.94, 139.90, 136.59, 136.16, 127.99, 127.75, 127.38, 127.33, 127.09, 121.89, 115.77, 113.06, 109.53, 49.04, 43.30, 14.54, 13.28. LCMS m/z: [M−H]$^-$ 443.5 (100%). LCMS m/z: [M+H]$^+$ 446.6 (100%).

N-Butyl-4-{2[(3,4,5-trihydroxyphenyl)carbonyl]-1-benzofuran-5-yl}benzene-1-sulfonamide (APY-094)

Figure 9:
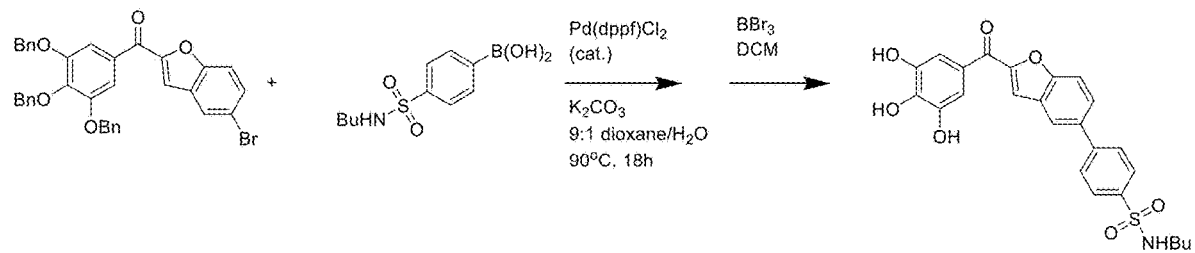
FIG. 9 depicts a chemical reaction diagram of the synthesis of N-Butyl-4-{2-[(3,4,5-trihydroxyphenyl)carbonyl]-1-benzofuran-5-yl}benzene-1-sulfonamide (APY-094).

A stirred mixture of (5-bromobenzofuran-3-yl)(3,4,5-tris(benzyloxy)phenyl)methanone (186 mg, 0.30 mmol), [4-(butylsulfamoyl)phenyl]boronic acid (108 mg, 0.42 mmol) and potassium carbonate (166 mg, 1.2 mmol) in 9:1 dioxane/water (3 mL) in a pressure tube was degassed over minutes with argon, then treated with 1,1-bis(diphenylphosphino)ferrocene dichloropalladium (II) (25 mg, 0.034 mmol), capped, and heated to 90° C. for 18 hours and cooled to room temperature and diluted with DCM (12 mL) and filtered through Celite®. The residual dark oil was dissolved in DCM and loaded onto a silica gel column (~80 cc) and eluted with 2% EtOAc/DCM, then 3% EtOAc/DCM to afford 189 mg (84%) of the penultimate intermediate as a white solid. A cooled (−70° C.) stirred solution of this compound (185 mg, 0.246 mmol) in anhydrous DCM (5 mL) under nitrogen was subjected to Procedure A with 1N BBr3/DCM (2.0 mL, 2.0 mmol), and the resultant material was dissolved in 10% methanol/DCM and added to a silica gel column (~90 cc) and eluted with 10% methanol/DCM to afford 89 mg (75%) of N-butyl-4-{2[(3,4,5-trihydroxyphenyl)carbonyl]-1-benzofuran-5-yl}benzene-1-sulfonamide as a brown solid (FIG. 9). $^1$H NMR (d6-acetone): δ 8.38 (m, 3H), 8.18 (br s, 1H), 7.84-8.00 (m, 5H), 7.80 (d, J=9 Hz, 1H), 7.70 (br s, 1H), 7.30 (s, 2H), 6.46 (t, J=6 Hz, 1H), 2.95 (q, J=7 Hz, 2H), 1.48 (m, 2H), 1.33 (m, 2H), 0.85 (t, J=7 Hz, 3H). $^{13}$C NMR (d6-acetone): δ 181.66, 155.54, 153.66, 145.38, 144.47, 139.83, 138.64, 135.61, 128.05, 127.99, 127.71, 127.52, 127.42, 121.94, 114.87, 112.62, 109.44, 42.76, 31.53, 19.49, 12.97. LCMS m/z: [M−H]$^-$ 479.5 (80%), 480.5 (100%).

1-(4-{2-[(3,4,5-Trihydroxyphenyl)carbonyl]-1-benzofuran-5-yl}phenyl)ethan-1-one (APY-101)

Figure 10:
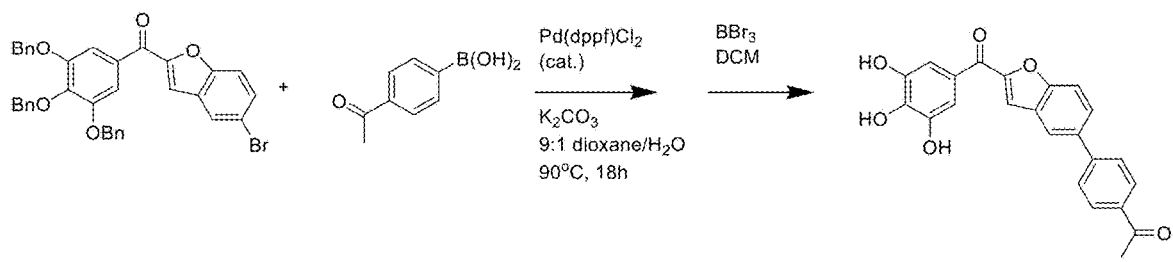
FIG. 10 depicts a chemical reaction diagram of the synthesis of 1-(4-{2-[(3,4,5-Trihydroxyphenyl)carbonyl]-1-benzofuran-5-yl}phenyl)ethan-1-one (APY-101).

A stirred mixture of (5-bromobenzofuran-3-yl)(3,4,5-tris(benzyloxy)phenyl)methanone (248 mg, 0.40 mmol), 4-acetylphenylboronic acid (92 mg, 0.56 mmol) and potassium carbonate (221 mg, 1.6 mmol) in 9:1 degassed dioxane/water (4 mL) in a pressure tube was treated with 1,1-bis(diphenylphosphino)-ferrocene dichloropalladium (II) (34 mg, 0.046 mmol), capped under nitrogen, and heated to 90° C. for 18 hours. The solution was cooled to room temperature, diluted with DCM (15 mL) and filtered through Celite®. The filtrate was concentrated in vacuo and the dark residue was dissolved in DCM and loaded onto a silica gel column (~100 cc) and eluted with DCM, then 3% EtOAc/DCM to afford 170 mg (65%) of the penultimate intermediate as a white solid. A cooled (−70° C.) stirred solution of this compound (165 mg, 0.251 mmol) in anhydrous DCM (5 mL) under nitrogen was subjected to Procedure A with 1N BBr3/DCM (2.0 mL, 2.0 mmol), and the resultant solid was dissolved in EtOAc/MeOH. The solution was added to a silica gel column (~50 cc) and eluted with 15% MeOH/EtOAc to afford a brown solid which was triturated from DCM to afford 80 mg (82%) of 1-(4-{2-[(3,4,5-trihydroxyphenyl)carbonyl]-1-benzofuran-5-yl}phenyl)ethan-1-one as a tan solid (FIG. 10). $^1$H NMR (d6-acetone): δ 8.50-8.85 (m, 3H), 8.18 (m, 1H), 8.10 (d, J=8 Hz, 2H), 7.90 (m, 1H), 7.86 (d, J=8 Hz, 2H), 7.80 (d, J=9 Hz, 1H), 7.69 (s, 1H), 7.27 (s, 2H), 2.62 (s, 3H). $^{13}$C NMR (d6-acetone): δ 196.66, 181.79, 155.49, 153.68, 145.76, 145.05, 138.96, 136.00, 135.96, 128.91, 128.01, 127.83, 127.33, 127.29, 121.82, 114.82, 112.58, 109.40, 25.92. LCMS m/z: [M−H]$^-$ 387.2 (100%). LCMS m/z: [M+H]$^+$ 389.1 (100%).

5-({5-[6-(Trifluoromethyl)pyridin-3-yl]-1-benzofuran-2-yl}carbonyl)benzene-1,2,3-triol (APY-097)

Figure 11:
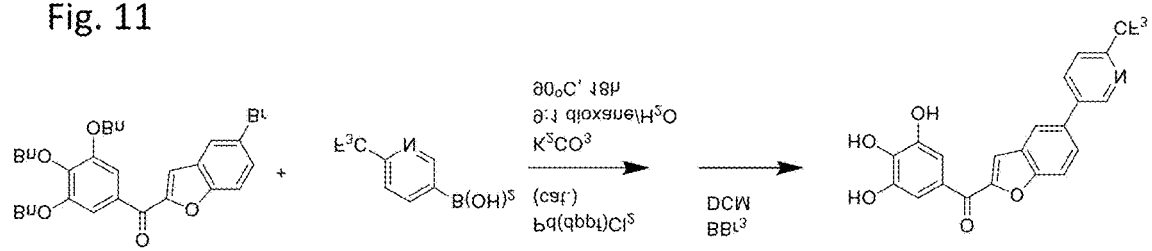
FIG. 11 depicts a chemical reaction diagram of the synthesis of 5-({5-[6-(Trifluoromethyl)pyridin-3-yl]-1-benzofuran-2-yl}carbonyl)benzene-1,2,3-triol (APY-097).

A stirred mixture of (5-bromobenzofuran-3-yl)(3,4,5-tris(benzyloxy)phenyl)methanone (248 mg, 0.40 mmol), [6-(trifluoromethyl)pyridin-3-yl]boronic acid (107 mg, 0.56 mmol) and potassium carbonate (221 mg, 1.6 mmol) in 9:1 degassed dioxane/water (4 mL) in a pressure tube was treated with 1,1-bis(diphenylphosphino)ferrocene dichloropalladium (II) (34 mg, 0.046 mmol), capped under nitrogen, and heated to 90° C. for 18 hours and cooled to room temperature and diluted with DCM (15 mL) and filtered through Celite®. The dark residue was dissolved in DCM and loaded onto a silica gel column (~100 cc) and eluted with 1.5% EtOAc/DCM, then 3% EtOAc/DCM to afford 222 mg (81%) of the penultimate intermediate as a white solid. A cooled (−70° C.) stirred solution of this compound (220 mg, 0.321 mmol) in anhydrous DCM (6 mL) under nitrogen was subjected to Procedure A with 1N BBr3/DCM (2.6 mL, 2.6 mmol), and the resultant brown solid was dissolved in 9:1 DCM/methanol and loaded onto a silica gel column (~75 cc) and eluted with 10% methanol/EtOAc. The resultant glassy solid was triturated from DCM to afford 101 mg (76%) of 5-({5-[6-(trifluoromethyl)pyridin-3-yl]-1-benzofuran-2-yl}carbonyl)benzene-1,2,3-triol as a tan solid (FIG. 11). $^1$H NMR (d6-acetone): δ 9.10 (s, 1H), 8.39 (m, 4H), 8.26 (s, 1H), 7.97 (d, J=8.5 Hz, 2H), 7.85 (m, 1H), 7.72 (s, 1H), 7.30 (s, 2H). $^{13}$C NMR (d6-DMSO): δ 181.63, 155.77, 153.79, 148.60, 145.39, 139.36, 138.69, 136.10, 132.47, 128.15, 127.99, 127.43, 122.95, 122.38, 121.14, 120.60, 114.72, 112.95, 109.45. LCMS m/z: [M−H]$^-$ 414.5 (100%). LCMS m/z: [M+H]$^+$ 416.3 (100%).

N-(2-(dimethylamino)ethyl)-2-(3,4,5-trihydroxybenzoyl)-benzofuran-5-carboxamide (NED-2018)

An ice cooled stirred solution of 2-{[3,4,5-tris(benzyloxy)phenyl]carbonyl}-3a,7a-dihydro-1-benzofuran-5-carboxylic acid (250 mg, 0.43 mmol), 2-dimethylaminoethylamine (45 mg, 0.51 mmol) and HOBT hydrate (81.6 mg, 0.53 mmol) in anhydrous DCM (4 mL) under nitrogen was treated with trimethylamine (0.18 mL, 1.28 mmol) and EDCI (102 mg, 0.53 mmol). Allowed reaction to warm to room temperature and stir overnight (18 h). The resulting reaction was concentrated to an oily residue, which was purified by flash chromatography (10% diethylamine in Ethyl Acetate) to afford N-[2-(dimethylamino)ethyl]-2-{[3,4,5-tris(benzyloxy)phenyl]carbonyl}-3a,7a-dihydro-1-benzofuran-5-carboxamide.

A cooled (−70° C.) stirred solution of N-[2-(dimethylamino)ethyl]-2-{[3,4,5-tris(benzyloxy)phenyl]carbonyl}-3a,7a-dihydro-1-benzofuran-5-carboxamide (164 mg, 0.25 mmol) in anhydrous dichloromethane (5 mL) under nitrogen was treated dropwise with 1N $BBr_3$ in dichloromethane (2.0 ml, 2.0 mmol). The reaction was allowed to warm to room temperature and stirred for 2 h. The resultant suspension was cooled on an ice bath, quenched with saturated aqueous ammonium chloride (5 ml) and stirred for an additional 1 h. The resulting precipitate was filtered and washed with water and dichloromethane, then dissolved in methanol (20 ml), dried over anhydrous $MgSO_4$, filtered and concentrated in vacuo to afford N-(2-(dimethylamino)ethyl)-2-(3,4,5-trihydroxybenzoyl)-benzofuran-5-carboxamide (NED-2018) as beige solid (93 mg, 97%). $^1$H NMR (Methanol-d4): δ 8.4 (d, J=1.8 Hz, 1H), 8.07 (dd, J=8.8, 1.8 Hz, 1H), 7.74 (d, J=8.8 Hz, 1H), 7.69 (d, J=1.0 Hz, 1H), 7.19 (s, 2H), 3.80 (t, J=5.8 Hz, 2H), 3.42 (t, J=5.8 Hz, 2H), 3.34 (s, 1H), 3.30 (s, 6H).

N-(2-(diethylamino)ethyl)-2-(3,4,5-trihydroxybenzoyl)-benzofuran-5-carboxamide (NED-2019)

A suspension of 2-{[3,4,5-tris(benzyloxy)-phenyl]carbonyl}-1-benzofuran-5-carbonyl chloride (137 mg, 0.99 mmol), N,N-diethylethylenediamine (39 mg, 0.33 mmol) and potassium carbonate (51.6 mg, 0.53 mmol) in DCM (3 mL) and $H_2O$ (3 mL) was vigorously stirred at room temperature overnight (18 h). The resulting two layers were separated and the organic layer was washed with brine, dried over $MgSO_4$ and concentrated. The residue was purified by flash chromatography (10% diethylamine in Ethyl Acetate) to afford N-[2-(diethylamino)ethyl]-2-{[3,4,5-tris(benzyloxy)phenyl]carbonyl}-1-benzofuran-5-carboxamide.

A cooled (−70° C.) stirred solution of N-[2-(diethylamino)ethyl]-2-{[3,4,5-tris(benzyloxy)phenyl]carbonyl}-1-benzofuran-5-carboxamide (200 mg, 0.29 mmol) in anhydrous dichloromethane (5 mL) under nitrogen was treated dropwise with 1N BBr3 in dichloromethane (2.0 ml, 2.0 mmol). The reaction was allowed to warm to room temperature and stirred for 2 h. The resultant suspension was cooled on an ice bath, quenched with saturated aqueous ammonium chloride (5 ml) and stirred for an additional 1 h. The resulting precipitate was filtered and washed with water and dichloromethane, then dissolved in methanol (20 ml), dried over anhydrous $MgSO_4$, filtered and concentrated in vacuo to afford N-(2-(diethylamino)ethyl)-2-(3,4,5-trihydroxybenzoyl)-benzofuran-5-carboxamide (NED-2019) as tan solid (65 mg, 54%). $^1$H NMR (Methanol-$d_4$): δ 8.34 (d, J=1.8 Hz, 1H), 8.03 (dd, J=8.8, 1.9 Hz, 1H), 7.75 (d, J=8.7 Hz, 1H), 7.68 (d, J=0.9 Hz, 1H), 7.18 (s, 2H), 3.77 (t, J=6.1 Hz, 2H), 3.46-3.31 (m, 6H), 1.35 (t, J=7.3 Hz, 6H).

N-(2,4-dimethylphenyl)-2-(3,4,5-trihydroxybenzoyl) benzofuran-5-carboxamide (NED-2021)

An ice cooled stirred solution of 2-{[3,4,5-tris(benzyloxy)phenyl]carbonyl}-3a,7a-dihydro-1-benzofuran-5-carboxylic acid (250 mg, 0.43 mmol), 2,4-dimethyl aniline (62 mg, 0.51 mmol) and HOBT hydrate (81.6 mg, 0.53 mmol) in anhydrous DCM (4 mL) under nitrogen was treated with trimethylamine (0.18 mL, 1.28 mmol) and EDCI (102 mg, 0.53 mmol). Allowed reaction to warm to room temperature and stir overnight (18 h). The resulting reaction was concentrated to an oily residue, which was purified by flash chromatography (10% diethylamine in Ethyl Acetate) to afford N-(2,4-dimethylphenyl)-2-{[3,4,5-tris(benzyloxy)phenyl]carbonyl}-3a,7a-dihydro-1-benzofuran-5-carboxamide.

A cooled (−70° C.) stirred solution of N-(2,4-dimethylphenyl)-2-{[3,4,5-tris(benzyloxy)phenyl]carbonyl}-1-benzofuran-5-carboxamide (172.3 mg, 0.25 mmol) in anhydrous dichloromethane (5 mL) under nitrogen was treated dropwise with 1N $BBr_3$ in dichloromethane (2.0 ml, 2.0 mmol). The reaction was allowed to warm to room temperature and stirred for 2 h. The resultant suspension was cooled on an ice bath, quenched with saturated aqueous ammonium chloride (5 ml) and stirred for an additional 1 h. The resulting precipitate was filtered and washed with water and dichloromethane, then dissolved in methanol (20 ml), dried over anhydrous $MgSO_4$, filtered and concentrated in vacuo to afford N-(2,4-dimethylphenyl)-2-{[3,4,5-tris(benzyloxy)phenyl]carbonyl}-1-benzofuran-5-carboxamide (NED-2021) as light brown solid (100 mg, 96%). $^1$H NMR (Methanol-$d_4$): δ 8.62 (d, J=1.9 Hz, 1H), 8.24 (dd, J=8.9, 2.0 Hz, 1H), 7.90 (d, J=8.8 Hz, 1H), 7.78 (s, 1H), 7.20 (d, J=14.5 Hz, 3H), 7.05 (s, 1H), 2.52 (s, 3H), 2.33 (s, 3H).

(4-isopropylpiperazin-1-yl)(2-(3,4,5-trihydroxybenzoyl)-benzofuran-5-yl)methanone (NED-2022)

A suspension of 2-{[3,4,5-tris(benzyloxy)-phenyl]carbonyl}-1-benzofuran-5-carbonyl chloride (210 mg, 0.35 mmol), 1-isopropylpiperazine (54 mg, 0.42 mmol) and potassium carbonate (144.4 mg, 1.04 mmol) in DCM (3 mL) and $H_2O$ (3 mL) was vigorously stirred at room temperature overnight (18 h). The resulting two layers were separated and the organic layer was washed with brine, dried over $MgSO_4$ and concentrated. The residue was purified by flash chromatography (10% diethylamine in Ethyl Acetate) to afford 1-(propan-2-yl)-4-[(2-{[3,4,5-tris(benzyloxy)phenyl]carbonyl}-1-benzofuran-5-yl)carbonyl]piperazine.

A cooled (−70° C.) stirred solution of 1-(propan-2-yl)-4-[(2-{[3,4,5-tris(benzyloxy)phenyl]carbonyl}-1-benzofuran-5-yl)carbonyl]piperazine (153 mg, 0.22 mmol) in anhydrous dichloromethane (5 mL) under nitrogen was treated dropwise with 1N $BBr_3$ in dichloromethane (2.0 ml, 2.0 mmol). The reaction was allowed to warm to room temperature and stirred for 2 h. The resultant suspension was cooled on an ice bath, quenched with saturated aqueous ammonium chloride (5 ml) and stirred for an additional 1 h. The resulting precipitate was filtered and washed with water and dichloromethane, then dissolved in methanol (20 ml), dried over anhydrous MgSO4, filtered and concentrated in vacuo to afford (4-isopropylpiperazin-1-yl)(2-(3,4,5-trihydroxybenzoyl)-benzofuran-5-yl)methanone (NED-2022) as light brown solid (92 mg, 98%). $^1$H NMR (Methanol-$d_4$): δ 7.99 (dd, J=1.7, 0.7 Hz, 1H), 7.77 (d, J=8.6 Hz, 1H), 7.69-7.62 (m, 2H), 7.37 (d, J=1.6 Hz, 1H), 7.34-7.29 (m, 1H), 7.18 (s, 2H), 4.61 (s, 1H), 3.61-3.23 (m, 8H), 1.39 (d, J=6.7 Hz, 6H).

N-((1-methylpiperidin-4-yl)methyl)-2-(3,4,5-trihydroxybenzoyl)-benzofuran-5-carboxamide (NED-2023)

An ice cooled stirred solution of 2-{[3,4,5-tris(benzyloxy)phenyl]carbonyl}-3a,7a-dihydro-1-benzofuran-5-carboxylic acid (200 mg, 0.34 mmol), (1-methyl-4-piperidinyl)-methylamine (52 mg, 0.41 mmol) and HOBT hydrate (65 mg, 0.43 mmol) in anhydrous DCM (4 mL) under nitrogen was treated with trimethylamine (0.14 mL, 1.02 mmol) and EDCI (82 mg, 0.43 mmol). Allowed reaction to warm to room temperature and stir overnight (18 h). The resulting reaction was concentrated to an oily residue, which was purified by flash chromatography (10% diethylamine in Ethyl Acetate) to afford N-[(1-methylpiperidin-4-yl)methyl]-2-[(3,4,5-trihydroxyphenyl)carbonyl]-1-benzofuran-5-carboxamide.

A cooled (−70° C.) stirred solution of N-[(1-methylpiperidin-4-yl)methyl]-2-[(3,4,5-trihydroxyphenyl)carbonyl]-1-benzofuran-5-carboxamide (139 mg, 0.20 mmol) in anhydrous dichloromethane (5 mL) under nitrogen was treated dropwise with 1N BBr3 in dichloromethane (2.0 ml, 2.0 mmol). The reaction was allowed to warm to room temperature and stirred for 2 h. The resultant suspension was cooled on an ice bath, quenched with saturated aqueous ammonium chloride (5 ml) and stirred for an additional 1 h. The resulting precipitate was filtered and washed with water and dichloromethane, then dissolved in methanol (20 ml), dried over anhydrous MgSO$_4$, filtered and concentrated in vacuo to afford N-((1-methylpiperidin-4-yl)methyl)-2-(3,4,5-trihydroxybenzoyl)-benzofuran-5-carboxamide (NED-2023) as light brown solid (54 mg, 64%). $^1$H NMR (Methanol-d$_4$): δ 8.29 (d, J=1.8 Hz, 1H), 7.98 (dd, J=8.8, 1.9 Hz, 1H), 7.70 (d, J=8.8 Hz, 1H), 7.66 (d, J=0.9 Hz, 1H), 7.18 (s, 2H), 3.52 (d, J=12.1 Hz, 2H), 3.37 (d, J=6.5 Hz, 2H), 2.99 (s, 1H), 2.85 (s, 3H), 2.04 (d, J=14.8 Hz, 2H), 1.55 (d, J=13.5 Hz, 2H).

Preparation of Aurones (Z)-2-(3,4,5-Trihydroxybenzylidene)benzofuran-3(2H)-one (APY-024)

Figure 12:
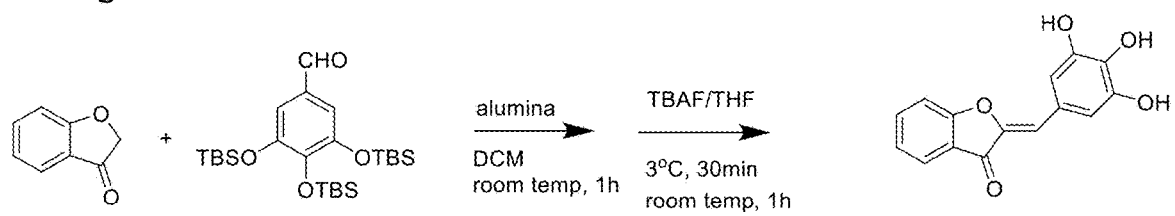
FIG. 12 depicts a chemical reaction diagram of the synthesis of (Z)-2-(3,4,5-Trihydroxybenzylidene)benzofuran-3(2H)-one (APY-024).

A stirred solution of 3,4,5-tris((tert-butyldimethylsilyl)oxy)benzaldehyde (Horenstein and Nakanishi, 1989, J. Am. Chem. Soc, 111:6242-6246)(1.84 g, 3.7 mmol) and benzofuran-3(2H)-one (0.55 g, 4.1 mmol) in dichloromethane (20 mL) was treated with neutral alumina (14 g) and stirred for 1 hour, then diluted with methanol (10 mL) and filtered. The solid was rinsed with 2:1 DCM/methanol until color wasn't seen in the filtrate and no more product detected by TLC, and the filtrate was concentrated in vacuo. The residual solid was recrystallized from acetonitrile to afford 1.66 g (73%) of trisilylated intermediate as a bright yellow solid, which was carried through without characterization. An ice-cooled (3° C.) stirred solution of this compound (1.594 g, 2.6 mmol) in anhydrous THF (25 mL) under argon was treated with 1N tetrabutylammonium fluoride/THF (9.6 mL, 9.6 mmol) and stirred at 3° C. for 30 minutes and at room temperature for 1 hour. Saturated aqueous ammonium chloride (50 mL) was added, followed by adjustment to pH~3 with 2N HCl (whereupon the color lightened to yellow orange). The mixture was extracted with ethyl acetate (150 mL, then 2×50 mL) and the combined organic solution was washed with water and brine (50 mL each), dried (MgSO4) and concentrated in vacuo to a yellow-orange solid. This was triturated from acetonitrile to afford 692 mg (98.5%) of (Z)-2-(3,4,5-trihydroxybenzyl-idine)benzo-furan-3(2H)-one as an orange solid (FIG. 12). $^1$H NMR (d6-DMSO): δ 9.17 (br s, 3H), 7.75 (m, 2H), 7.46 (d, J=8.5 Hz, 1H), 7.27 (t, J=7.5 Hz, 1H), 6.98 (s, 2H), 6.89 (s, 1H). $^{13}$C NMR (d6-DMSO): δ 183.31, 165.24, 146.48, 145.13, 137.44, 137.34, 124.47, 124.01, 122.37, 121.73, 114.82, 113.28, 111.68. LCMS m/z: [M−H]$^-$ 269.8 (100%).

(Z)-2-(3,4-Dimethoxybenzylidene)-4,6-dihydroxybenzofuran-3(2H)-one (APY-001)

Figure 13:
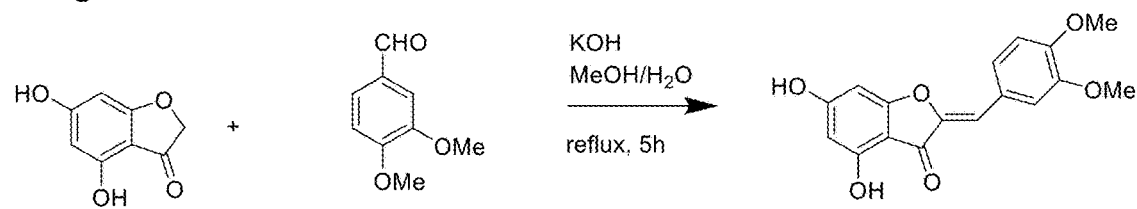
FIG. 13 depicts a chemical reaction diagram of the synthesis of (Z)-2-(3,4-Dimethoxybenzylidene)-4,6-dihydroxybenzofuran-3(2H)-one (APY-001).

A stirred mixture of 4,6-dihydroxybenzofuran-3(2H)-one (Haudecoeur et al., 2011, Journal of medicinal chemistry, 54:5395-5402) (166 mg, 1.0 mmol) and 3,4-dimethoxybenzaldehyde (249 mg, 1.5 mmol) in methanol (15 mL) was treated with 50% aqueous potassium hydroxide (1.5 mL) and heated to reflux for 5 hours, then cooled to room temperature. Methanol was removed in vacuo and replaced with water (30 mL), and the solution was washed with ether (2×20 mL, decanted from mixture). The solution was acidified to pH~4 with concentrated HCl, and the resultant suspension was filtered, washed several times with water, and the solid dried in vacuo overnight. Recrystallization from acetonitrile afforded 232 mg (74%) of (Z)-2-(3,4-dimethoxybenzylidene)-4,6-dihydroxybenzofuran-3(2H)-one as a yellow solid (FIG. 13). $^1$H NMR (d6-DMSO): δ 10.90 (br s, 1H), 10.86 (br s, 1H), 7.52 (m, 2H), 7.07 (d, J=7 Hz, 1H), 6.59 (s, 1H), 6.24 (d, J=2 Hz, 1H), 6.11 (d, J=2 Hz, 1H), 3.83 (s, 3H), 3.82 (s, 3H). $^{13}$C NMR (d6-DMSO): δ 179.32, 167.93, 167.52, 158.59, 150.29, 149.06, 146.91, 125.43, 124.80, 114.32, 112.34, 109.18, 103.06, 98.07, 90.92, 55.93, 55.88. LCMS m/z: [M−H]$^-$ 313.1 (30%). LCMS m/z: [M+H]$^+$ 315.2 (100%).

(Z)-2-(3,4-Dihydroxybenzylidene)-4,6-dihydroxybenzofuran-3(2H)-one (APY-007)

Figure 14:
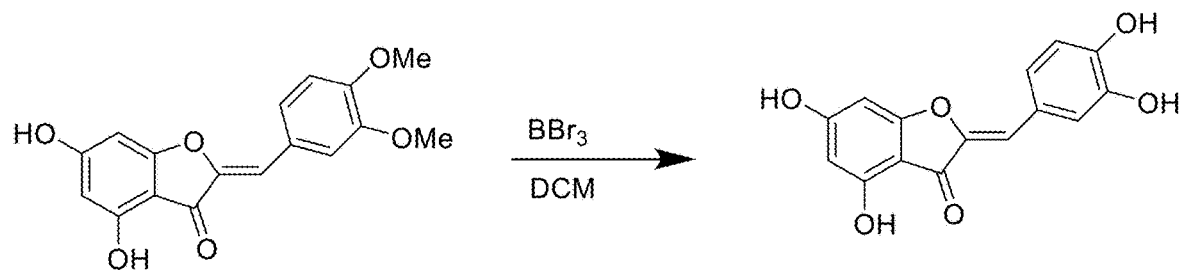
FIG. 14 depicts a chemical reaction diagram of the synthesis of (Z)-2-(3,4-Dihydroxybenzylidene)-4,6-dihydroxybenzofuran-3(2H)-one (APY-007).

An ice-cooled stirred suspension of (Z)-2-(3,4-dimethoxybenzylidene)-4,6-dihydroxybenzofuran-3(2H)-one (126 mg, 0.40 mmol) in anhydrous methylene chloride (3 mL) under argon was treated dropwise with 1N boron tribromide/dichloromethane (5 mL, 5 mmol), then allowed to reach room temperature overnight. The dark red mixture was added to ice (40 mL) and extracted with ethyl acetate (4×40 mL). The combined organic solution was washed with water (3×75 mL), brine (75 mL), dried (MgSO$_4$), and concentrated in vacuo. The residual solid was triturated from acetonitrile to afford 52 mg (45%) of (Z)-2-(3,4-dihydroxybenzylidene)-4,6-dihydroxybenzofuran-3(2H)-one as a yellow solid (FIG. 14). $^1$H NMR (d6-DMSO): δ 10.25-11.25 (br s, 2H), 8.75-10.00 (br s, 2H), 7.44 (d, J=2 Hz, 1H), 7.23 (dd, J=8 Hz, 2 Hz, 1H), 6.87 (d, J=8 Hz, 1H), 6.49 (s, 1H), 6.21 (d, J=2 Hz, 1H), 6.11 (d, J=2 Hz, 1H). $^{13}$C NMR (d6-DMSO): δ 179.31, 167.87, 167.51, 158.64, 147.77, 146.29, 145.79, 124.22, 124.03, 117.91, 116.30, 109.79, 103.16, 98.04, 90.61. LCMS m/z: [M−H]$^-$ 284.8 (100%). LCMS m/z: [M+H]$^+$ 286.8 (100%).

(Z)-2-(3,5-Dihydroxybenzylidene)-4,6-dihydroxybenzofuran-3(2H)-one (APY-014)

Figure 15:
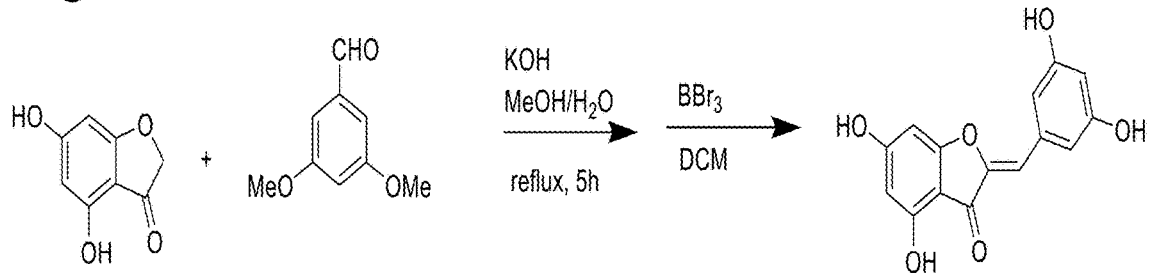
FIG. 15 depicts a chemical reaction diagram of the synthesis of (Z)-2-(3,5-Dihydroxybenzylidene)-4,6-dihydroxybenzofuran-3(2H)-one (APY-014).

A stirred mixture of 4,6-dihydroxybenzofuran-3(2H)-one (31) (166 mg, 1.0 mmol) and 3,5-dimethoxybenzaldehyde (249 mg, 1.5 mmol) in methanol (15 mL) was treated with 50% aqueous potassium hydroxide (1.5 mL) and heated to reflux for 5 hours, then cooled to room temperature. The solution was concentrated in vacuo and the residue dissolved in water (15 mL) and acidified to pH~2 with HCl. The resultant suspension was cooled on an ice bath, filtered, and the solid washed several times with water and dried in vacuo. Trituration from cold acetonitrile afforded 240 mg (76%) of penultimate intermediate as a pale beige solid, carried forward without characterization. A cooled (–70° C.) suspension of this compound (235 mg, 0.75 mmol) in anhydrous dichloromethane (5 mL) under argon was treated dropwise via syringe with 1N boron tribromide/dichloromethane (5 mL) and allowed to reach 0° C. over 1.5 hours, then maintained on an ice bath and allowed to reach room temperature overnight (16 hours). The reaction mixture was poured onto ice, stirred several minutes, filtered, and the solid rinsed several times with water and air dried. The solid was dissolved in dichloromethane containing a little methanol, loaded onto a short column of silica gel (~25 cc) and eluted with 10% methanol/ethyl acetate to afford a dark brown solid. This was triturated from cold ether to afford 90 mg (42%) of (Z)-2-(3,5-dihydroxybenz-ylidene)-4,6-dihydroxybenzofuran-3(2H)-one as a brown powder (FIG. 15). $^1$H NMR (d6-DMSO): δ 10.25-11.50 (br s, 2H), 9.15-9.75 (br s, 2H), 6.77 (d, J=2 Hz, 2H), 6.37 (s, 1H), 6.28 (t, J=2 Hz, 1H), 6.17 (d, J=2 Hz, 1H), 6.08 (d, J=2 Hz, 1H). $^{13}$C NMR (d6-DMSO): δ 179.41, 168.13, 167.87, 158.85, 147.88, 133.97, 109.21, 109.11, 105.95, 104.38, 102.90, 98.18, LCMS m/z: EM-fir 284.8 (100%). LCMS m/z: [M+H]$^+$ 286.8 (100%).

(Z)-4-Hydroxy-2-(3,4,5-trihydroxybenzylidene)benzofuran-3(2H)-one (APY-019)

Figure 16:
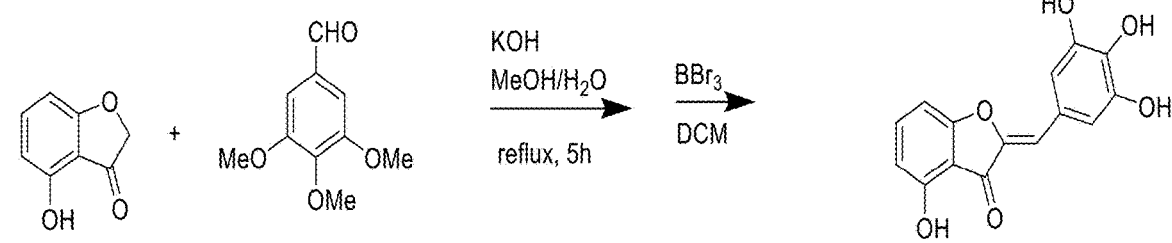
FIG. 16 depicts a chemical reaction diagram of the synthesis of (Z)-4-Hydroxy-2-(3,4,5-trihydroxybenzylidene)benzofuran-3(2H)-one (APY-019).
Figure 17:
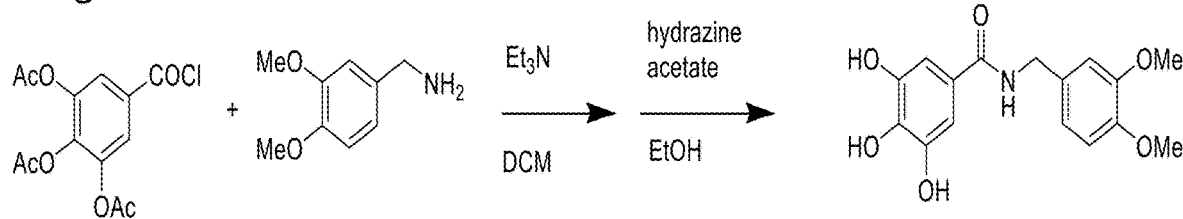
FIG. 17 depicts a chemical reaction diagram of the synthesis of N-[(3,4-Dimethoxyphenyl)methyl]-3,4,5-trihydroxybenzamide (APY-077).

A stirred mixture of 4-hydroxybenzofuran-3(2H)-one (Singh et al., 2010, Journal of medicinal chemistry, 53:18-36) (150 mg, 1.0 mmol) and 3,4,5-trimethoxybenzaldehyde (294 mg, 1.5 mmol) in methanol (15 mL) was treated with 50% aqueous potassium hydroxide (1.5 mL) and heated to reflux for 5 hours, then cooled to room temperature and concentrated in vacuo. Water (15 mL) was added, the mixture cooled on an ice bath, and acidified with concentrated HCl to pH~3 (yellow precipitate formed). Stirring on ice was continued for several minutes, then the suspension was filtered, rinsed several times with cold water, and dried in vacuo. The solid was recrystallized from acetonitrile and dried to afford 259 mg (79%) of penultimate intermediate as a yellow solid, carried forward without characterization. A cooled (–65° C.) stirred suspension of this compound (213 mg, 0.65 mmol) in anhydrous dichloromethane (5 mL) under argon was treated with 1N BBr3/dichloromethane (5 mL, 5 mmol) at a rate to keep pot temp below –50° C., then allowed to reach 0° C. over 1.5 hours. The mixture was placed on an ice bath and allowed to reach room temperature overnight. The reaction was quenched by addition to ice and stirring, and the aqueous suspension was filtered and the solid rinsed several times with water and partially air dried. Trituration from acetonitrile afforded 151 mg (81%) of (Z)-4-hydroxy-2-(3,4,5-trihydroxybenzylidene)benzofuran-3(2H)-one as a yellow-brown solid (FIG. 16). $^1$H NMR (d6-DMSO): δ 11.01 (br s, 1H), 9.20 (br s, 2H), 8.90 (br s, 1H), 7.52 (t, J=7 Hz, 1H), 6.96 (s, 2H), 6.80 (d, J=8 Hz, 1H), 6.63 (d, J=8 Hz, 1H), 6.52 (s, 1H). $^{13}$C NMR (d6-DMSO): δ 181.35, 166.02, 157.29, 146.41, 145.26, 138.47, 136.64, 122.61, 112.31, 111.16, 110.65, 109.81, 102.58. LCMS m/z: [M–H]$^-$ 285.6 (100%).

Preparation of Benzohydrazides 3,4,5-trihydroxybenzohydrazide (NED-2047)

A solution of methyl gallate (4 g, 21.7 mmol) in ethanol (25 mL) was hydrazine hydrate (4.35 g, 86.9 mmol) and heated to a gentle reflux. After stirring for 18 h, the reaction mixture was cooled to room temperature, and the precipitated product was filtered and sequentially washed with water and ethanol and dried in a vacuum oven to give the title compound (3.85 g, 96%) as a white solid. 1H NMR (DMSO-D6) 9.29 (s, 1H), 8.97 (br s, 2H), 8.60 (br s, 1H), 6.74 (s, 2H), 4.28 (s, 2H). LC-MS: m/z=185 [M+].

N'-(2,4-dimethoxybenzylidene)-3,4,5-trihydroxybenzohydrazide (NED-2036)

A suspension of 3,4,5-trihydroxybenzohydrazide (367 mg, 1.99 mmol; NED-2047) in ethanol (6 mL) was treated with 2,4-dimethoxybenzaldehyde (300 mg, 1.81 mmol) and heated to a gentle reflux for 16 h. After cooling to room temperature, the precipitated product was washed with ethanol (2×10 mL) and hexanes (2×5 mL). The precipitate was dried in a vacuum oven for 24 h to give the title compound as a white solid (155 mg, 26%). 1H NMR (DMSO-D6) 11.38 (s, 1H), 9.30 (s, 1H), 8.98 (br s, 2H), 8.79 (s, 1H), 8.63 (s, 1H), 7.87 (d, J=8.5 Hz, 1H), 7.73 (d, J=9.1 Hz, 1H), 6.88 (s, 1H), 6.75 (s, 1H), 6.63-6.57 (m, 4H), 3.84-3.78 (m, 12H). LC-MS: m/z=333 [M+].

(E)-3,4,5-trihydroxy-N'-((2-hydroxynaphthalen-1-yl)methylene)benzohydrazide (NED-2037)

A suspension of 3,4,5-trihydroxybenzohydrazide (300 mg, 1.63 mmol; NED-2047) in methanol (10 mL) was treated with 2-hydroxy-1-naphthaldehyde (297 mg, 1.72 mmol) and heated to a gentle reflux for 16 h. After cooling to room temperature, the precipitated product was washed with methanol (2×10 mL). The precipitate was dried in a vacuum oven for 24 h to give the title compound as a white solid (205 mg, 37%). 1H NMR (DMSO-D6) 9.38 (s, 1H), 8.12 (d, J=8.6 Hz, 1H), 7.83-7.78 (m, 2H), 7.55-7.50 (m, 1H), 7.37-7.33 (m, 1H), 7.16 (d, J=9.0 Hz, 1H), 7.00 (s, 2H). LC-MS: m/z=339 [M+].

(E)-N'-((5-(4-bromophenyl)furan-2-yl)methylene)-3,4,5-trihydroxybenzohydrazide (NED-2038)

A suspension of 3,4,5-trihydroxybenzohydrazide (400 mg, 2.17 mmol; NED-2047) in methanol (10 mL) was treated with 5-(4-bromophenyl)furfural (545 mg, 2.17 mmol) and heated to a gentle reflux for 16 hours. After cooling to room temperature, the precipitated product was washed with methanol (2×10 mL). The precipitate was dried in a vacuum oven for 24 hours to give the title compound as a white solid (385 mg, 42%). 1H NMR (DMSO-D6) 11.53 (s, 1H), 9.13 (bs, 1H), 8.30 (s, 1H), 7.71 (d, J=8.6 Hz, 2H), 7.63 (d, J=8.6 Hz, 2H), 7.16 (d, J=3.6 Hz, 2H), 6.97 (d, J=3.6 Hz, 2H), 6.88 (s, 2H). LC-MS: m/z=418,420 [M+].

(E)-3,4,5-trihydroxy-N'-(3,4,5-trimethoxybenzylidene)benzohydrazide (NED-2039)

A suspension of 3,4,5-trihydroxybenzohydrazide (300 mg, 1.63 mmol; NED-2047) in methanol (12 mL) was treated with 3,4,5-trimethoxybenzaldehyde (352 mg, 1.79 mmol) and heated to a gentle reflux for 16 h. After cooling to room temperature, the precipitated product was washed with methanol (2×10 mL) and ethyl acetate/dichloromethane (1×10 mL, 1:1). The precipitate was dried in a vacuum oven for 24 hours to give the title compound as a white solid (165 mg, 28%). 1H NMR (DMSO-D6) 11.51 (s, 1H), 9.14

(bs, 2H), 8.82 (bs, 1H), 8.31 (s, 1H), 6.95 (s, 2H), 6.89 (s, 2H), 3.82 (s, 6H), 3.68 (s, 3H). LC-MS: m/z=363 [M+].

(E)-N'-(4-(dimethylamino)benzylidene)-3,4,5-trihydroxybenzohydrazide (NED-2048)

A suspension of 3,4,5-trihydroxybenzohydrazide (300 mg, 1.63 mmol; NED-2047) in methanol (12 mL) was treated with 4-dimethylaminobenzaldehyde (267 mg, 1.79 mmol) and heated to a gentle reflux for 16 hours. After cooling to room temperature, the precipitated product was washed with methanol (2×10 mL) and ethyl acetate/dichloromethane (1×10 mL, 1:1). The precipitate was dried in a vacuum oven for 24 hours to give the title compound as a white solid (225 mg, 44%). 1H NMR (DMSO-D6) 11.21 (s, 1H), 9.08 (bs, 2H), 8.77 (bs, 1H), 8.22 (s, 1H), 7.46 (d, J=8.5 Hz, 2H), 6.85 (s, 2H), 6.72 (d, J=8.6 Hz, 2H), 2.93 (s, 6H).

(E)-3,4,5-trihydroxy-N'-(naphthalen-1-ylmethylene) benzohydrazide (NED-2134)

A suspension of 3,4,5-trihydroxybenzohydrazide (300 mg, 1.63 mmol; NED-2047) in methanol (12 mL) was treated with 1-naphthaldehyde (352 mg, 1.79 mmol) and heated to a gentle reflux for 16 hours. After cooling to room temperature, the precipitated product was washed with methanol (2×10 mL) and ethyl acetate/dichloromethane (1×10 mL, 1:1). The precipitate was dried in a vacuum oven for 24 hours to give the title compound as a white solid (165 mg, 28%). 1H NMR (DMSO-D6) 11.59 (s, 1H), 9.17 (s, 2H), 9.05 (s, 1H), 8.85 (s, 1H), 8.80 (d, J=8.5 Hz, 1H), 7.98 (d, J=8.1 Hz, 2H), 7.87 (d, J=7.2 Hz, 1H), 7.63-7.55 (m, 3H), 6.94 (s, 2H), LC-MS: m/z=323 [M+].

(E)-3,4,5-trihydroxy-N'-(naphthalen-2-ylmethylene) benzohydrazide (NED-2135)

A suspension of 3,4,5-trihydroxybenzohydrazide (280 mg, 1.52 mmol; NED-2047) in methanol (10 mL) was treated with 2-naphthaldehyde (250 mg, 1.60 mmol) and heated to a gentle reflux for 16 hours. After cooling to room temperature, the precipitated product was washed with methanol (2×10 mL) and ethyl acetate/methanol (1×10 mL, 1:1). The precipitate was dried in a vacuum oven for 24 hours to give the title compound as a white solid (455 mg, 93%). 1H NMR (DMSO-D6) 11.63 (s, 1H), 9.17 (s, 2H), 9.05 (s, 1H), 8.84 (s, 1H), 8.55 (s, 1H), 8.08 (s, 1H), 8.00-7.91 (m, 4H), 7.56-7.53 (m, 2H), 6.93 (s, 2H). LC-MS: m/z=323 [M+]; 345 [M+Na].

(E)-3,4,5-trihydroxy-N'46-methoxynaphthalen-2-yl) methylene)benzohydrazide (NED-2136)

A suspension of 3,4,5-trihydroxybenzohydrazide (250 mg, 1.36 mmol; NED-2047) in methanol (10 mL) was treated with 6-methoxy-2-naphthaldehyde (266 mg, 1.43 mmol) and heated to a gentle reflux for 16 hours. After cooling to room temperature, the precipitated product was washed with methanol (2×10 mL) and ethyl acetate/methanol (1×10 mL, 1:1). The precipitate was dried in a vacuum oven for 24 hours to give the title compound as a white solid (465 mg, 96%). 1H NMR (DMSO-D6) 11.54 (s, 1H), 9.15 (s, 2H), 8.82 (s, 1H), 8.48 (s, 1H), 7.99 (s, 1H), 7.89-7.81 (m, 3H), 7.33 (d, J=2.5 Hz, 1H), 7.19-7.16 (m, 1H), 6.90 (s, 2H). LC-MS: m/z=353 [M+].

(E)-3,4,5-trihydroxy-N'-((2-methoxynaphthalen-1-yl)methylene)benzohydrazide (NED-2173)

A suspension of 3,4,5-trihydroxybenzohydrazide (220 mg, 1.12 mmol; NED-2047) in methanol (10 mL) was treated with 2-methoxy-1-naphthaldehyde (220 mg, 1.18 mmol) and heated to a gentle reflux for 48 hours. After cooling to room temperature, the precipitated product was washed with methanol (2×10 mL). The precipitate was dried in a vacuum oven for 24 hours to give the title compound as a white solid (282 mg, 71%). 1H NMR (DMSO-D6) 11.60 (s, 1H), 9.38 (d, J=8.7 Hz, 1H), 9.13 (s, 2H), 9.10 (s, 1H), 8.01 (d, J=9.1 Hz, 1H), 7.88 (d, J=8.0 Hz, 1H), 7.56-7.53 (m, 1H), 7.49 (d, J=9.2 Hz, 1H), 7.42-7.38 (m, 1H), 6.96 (s, 2H). LC-MS: m/z=353 [M+].

(E)-3,4,5-trihydroxy-N'-((2-(prop-2-yn-1-yloxy) naphthalen-1-yl)methylene)benzohydrazide (NED-2174)

2-hydroxy-1-naphthaldehyde (350 mg, 2.03 mmol) was dissolved in anhydrous DMF (2 mL). Anhydrous $K_2CO_3$ (618 mg, 4.47 mmol) was added to this solution at room temperature, stirred for 20 minutes, and then charged with propargyl bromide (544 mg, 3.66 mmol). The resulting mixture was stirred at room temperature for 72 hours. After the completion of the reaction, ethyl acetate (30 mL) was added, the organic phase was washed with water (3×50 mL), dried over MgSO4, and filtered. Removal of solvent gave oily residue which was purified over silica gel flash chromatography (Eluent: 100% hexanes to 20% ethyl acetate in hexanes). 2-(prop-2-yn-1-yloxy)naphthalene-1-carbaldehyde was isolated as a clear oil and fraction one (410 mg, 96%). 1H NMR (CDCl₃) 10.91 (s, 1H), 9.29-9.26 (m, 1H), 8.08 (d, J=9.1 Hz, 1H), 7.81-7.78 (m, 1H), 7.66-7.62 (m, 1H), 7.47-7.43 (m, 1H), 7.39 (d, J=9.2 Hz, 1H), 4.96 (s, 2H), 2.58 (s, 1H).

A suspension of 3,4,5-trihydroxybenzohydrazide (216 mg, 1.17 mmol; NED-2047) in methanol (10 mL) was treated with 2-(prop-2-yn-1-yloxy)naphthalene-1-carbaldehyde (260 mg, 1.24 mmol) and heated to a gentle reflux for 16 hours. After cooling to room temperature, the precipitated product was washed with methanol (2×10 mL). The precipitate was dried in a vacuum oven for 24 hours to give the title compound as a white solid (270 mg, 61%). 1H NMR (DMSO-D6) 11.67 (s, 1H), 9.37 (d, J=8.7 Hz, 1H), 9.13 (bs, 2H), 9.07 (s, 1H), 8.74 (bs, 1H), 8.00 (d, J=9.1 Hz, 1H), 7.88 (d, J=8.1 Hz, 1H), 7.55-7.51 (m, 2H), 7.44-7.41 (m, 1H), 6.95 (s, 2H), 3.62 (s, 1H). LC-MS: m/z=377 [M+].

(E)-3,4,5-trihydroxy-N'-((2-(pyridin-2-ylmethoxy) naphthalen-1-yl)methylene)benzohydrazide (NED-2175)

2-hydroxy-1-naphthaldehyde (350 mg, 2.03 mmol) was dissolved in anhydrous DMF (2 mL). Anhydrous $K_2CO_3$ (1.01 g, 7.32 mmol) was added to this solution at room temperature, stirred for 20 minutes, and then charged with 2-(Bromomethyl)pyridine hydrobromide (925 mg, 3.66 mmol). The resulting mixture was stirred at room temperature for 72 hours. After the completion of the reaction, ethyl acetate (30 mL) was added, the organic phase was washed with water (3×50 mL), dried over MgSO4, and filtered. Removal of solvent gave oily residue which was purified over silica gel flash chromatography (Eluent: 100% hexanes to 65% ethyl acetate in hexanes). 2-(pyridin-2-ylmethoxy) naphthalene-1-carbaldehyde was isolated as a clear oil and fraction one (415 mg, 78%). 1H NMR (CDCl₃) 11.07 (s, 1H), 9.29 (m, 1H), 8.63 (m, 1H), 8.04 (d, J=9.1 Hz, 1H), 7.79-7.73 (m, 2H), 7.66-7.61 (m, 1H), 7.56 (d, J=7.8 Hz, 1H), 7.46-7.41 (m, 1H), 7.34 (d, J=7.8 Hz, 1H), 5.47 (s, 2H).

A suspension of 3,4,5-trihydroxybenzohydrazide (200 mg, 1.09 mmol; NED-2047) in methanol (10 mL) was treated with 2-(pyridin-2-ylmethoxy)naphthalene-1-carbaldehyde (301 mg, 1.14 mmol) and heated to a gentle reflux for 16 hours. After cooling to room temperature, the precipitated product was washed with methanol (2×10 mL). The precipitate was dried in a vacuum oven for 24 hours to give the title compound as a white solid (180 mg, 39%). 1H NMR (DMSO-D6) 11.68 (s, 1H), 9.37 (d, J=8.8 Hz, 1H), 9.19 (s, 1H), 9.14 (s, 2H), 8.80 (s, 1H), 8.57 (d, J=5.0 Hz, 1H), 7.96 (d, J=9.1 Hz, 1H), 7.87-7.83 (m, 2H), 7.66 (d, J=7.8 Hz, 1H), 7.58-7.52 (m, 1H), 7.42-7.39 (m, 1H), 7.35-7.32 (m, 1H), 6.94 (s, 2H), 5.42 (s, 2H). LC-MS: m/z=430 [M+].

(E)-N'-(cyclohexylmethylene)-3,4,5-trihydroxybenzohydrazide (NED-2251)

A suspension of 3,4,5-trihydroxybenzohydrazide (200 mg, 1.09 mmol; NED-2047) in methanol (8 mL) was treated with cyclohexanecarboxaldehyde (128 mg, 1.14 mmol) and heated to a gentle reflux for 18 hours. After cooling to room temperature, volatiles were removed. chloroform and 5 mL dichloromethane were added to the oily residue following concentration which resulted in precipitation of a white solid. The precipitate was filtered, washed with more dichloromethane (5 mL), diethyl ether (2×5 mL), collected, and dried in a vacuum oven for 24 hours to give the title compound as a white solid (265 mg, 88%). 1H NMR (DMSO-D6) 11.00 (s, 1H), 9.06 (s, 2H), 8.72 (s, 1H), 7.56 (d, J=5.4 Hz, 1H), 6.79 (s, 2H), 2.17 (bs, 1H), 1.73-1.66 (m, 4H), 1.60-1.57 (m, 1H), 1.27-1.13 (m, 5H). LC-MS: m/z=279 [M+].

Preparation of Additional Compounds

N-[(3,4-Dimethoxyphenyl)methyl]-3,4,5-trihydroxybenzamide (APY-077)

An ice cooled (3° C.) stirred solution of 3,4,5-triacetoxybenzoyl chloride (Bian et al., 2013, Bioorg Med Chem, 21:5442-5450) (315 mg, 1.0 mmol) in dichloromethane (5 mL) under nitrogen was treated with triethylamine (0.28 mL) then dropwise with 3,4-dimethoxybenzylamine (167 mg, 1.0 mmol) in dichloromethane (3 mL), warmed to room temperature, stirred overnight, and concentrated in vacuo. The residue was dissolved in dichloromethane and loaded onto a silica gel column (~80 cc) and eluted with 3:2 dichloromethane/ethyl acetate to afford 390 mg (88%) of penultimate intermediate as a white foam. A stirred suspension of this compound (381 mg, 0.855 mmol) in ethanol (10 mL) under nitrogen was treated with hydrazine hydrate (0.175 mL, 3.6 mmol) and stirred at room temperature for 2 hours, then concentrated in vacuo. The residual solid was stirred in water (12 mL) for 15 minutes, filtered, and the solid rinsed with water, collected and dried in vacuo to afford 238 mg (87%) of N-[(3,4-dimethoxyphenyl)methyl]-3,4,5-trihydroxybenzamide as a white powder. ¹H NMR (d6-acetone): δ 8.37 (br s, 2H), 8.00 (br s, 2H), 7.00 (m, 3H), 6.86 (m, 2H), 4.44 (s, 2H), 3.76 (s, 6H). ¹³C NMR (d6-acetone): δ 166.42, 149.34, 148.44, 145.54, 145.48, 136.04, 119.77, 111.90, 111.84, 106.88, 106.85, 55.30, 55.20, 42.73. LCMS m/z: [M–H]⁻ 317.6 (100%). LCMS m/z: [M+H]⁺ 319.6 (100%).

2-(4-Bromophenyl)-4-[3,4,5-tris(benzyloxy)phenyl]-1,3-thiazole (Intermediate 2)

Figure 18:
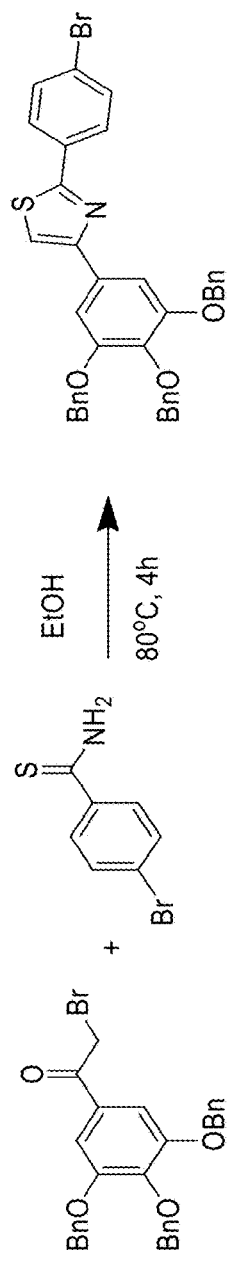
FIG. 18 depicts a chemical reaction diagram of the synthesis of 2-(4-Bromophenyl)-4-[3,4,5-tris(benzyloxy)phenyl]-1,3-thiazole (Intermediate 2).

A stirred mixture of 2-bromo-1-(3,4,5-tris(benzyloxy)phenyl)ethan-1-one (29) (1.3 g, 2.5 mmol) and 4-bromobenzene-1-carbothioamide (0.54 g, 2.5 mmol) in ethanol (25 mL) under nitrogen was heated to 80° C. for 4 hours, then cooled to room temperature. The suspension was filtered and the solid rinsed with ethanol, collected and dried in vacuo to afford 1.29 g (81%) of 2-(4-bromophenyl)-4-[3,4,5-tris(benzyloxy)phenyl]-1,3-thiazole as a voluminous white solid (FIG. 18). ¹H NMR (d6-acetone): δ 7.89 (d, J=9 Hz, 2H), 7.59 (d, J=9 Hz, 2H), 7.48 (m, 4H), 7.43 (m, 2H), 7.25-7.40 (m, 12H), 5.20 (s, 4H), 5.11 (s, 2H). ¹³C NMR (d6-acetone): δ 166.45, 156.08, 138.81, 137.73, 137.10, 132.49, 132.08, 129.89, 128.63, 128.50, 128.15, 128.00, 127.91, 127.83, 127.54, 127.53, 124.34, 112.49, 106.53, 75.25, 71.44. LCMS m/z: [M–H]⁻ 317.6 (100%). LCMS m/z: [M+H]⁺ 635.3 (100%).

N-Butyl-4-{4-[4-(3,4,5-trihydroxyphenyl)-1,3-thiazol-2-yl]phenyl}benzene-1-sulfonamide (APY-093)

Figure 19:
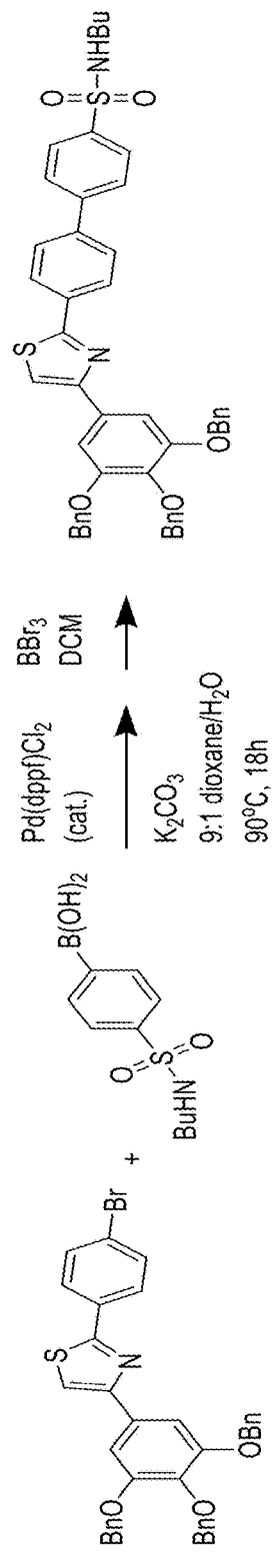
FIG. 19 depicts a chemical reaction diagram of the synthesis of N-Butyl-4-{4-[4-(3,4,5-trihydroxyphenyl)-1,3-thiazol-2-yl]phenyl}benzene-1-sulfonamide (APY-093).

A stirred mixture of 2-(4-bromophenyl)-4-[3,4,5-tris(benzyloxy)phenyl]-1,3-thiazole (254 mg, 0.40 mmol), [4-(butylsulfamoyl)phenyl]boronic acid (144 mg, 0.56 mmol) and potassium carbonate (221 mg, 1.6 mmol) in 9:1 dioxane/water (4 mL) in a pressure tube was degassed over 20 minutes with argon, then treated with 1,1-bis(diphenylphosphino)ferrocene dichloropalladium (II) (33 mg, 0.045 mmol). The tube was capped, and heated to 90° C. for 18 hours, cooled to room temperature and diluted with DCM (12 mL). The mixture was combined with water (10 mL) and separated. The aqueous solution was extracted with DCM (8 mL) and the combined organic solution was washed with water (10 mL), dried (MgSO4) and filtered and concentrated in vacuo. The residue was dissolved in DCM and loaded onto a silica gel column (~80 cc) and eluted with DCM, then 2% EtOAc/dichloromethane to afford 299 mg (97%) of penultimate intermediate as a pale yellow solid. A cooled (–70° C.) stirred solution of this compound (260 mg, 0.339 mmol) in anhydrous DCM (6 mL) was subjected to Procedure A with 1N BBr3/DCM (2.7 mL, 2.7 mmol), and the residual solid was triturated from DCM, then dissolved in 9:1 DCM/methanol and added to a silica gel column (~90 cc) and eluted with 5%, then 10% methanol/DCM. The solid product was triturated again from DCM to afford 110 mg (65%) of N-butyl-4-{4-[4-(3,4,5-trihydroxyphenyl)-1,3-thiazol-2-yl]phenyl}benzene-1-sulfonamide as a pale tan solid (FIG. 19). ¹H NMR (d6-acetone): δ 8.17 (d, J=8 Hz, 2H), 7.96 (m, 4H), 7.89 (d, J=8 Hz, 2H), 7.75-8.00 (br s, 3H), 7.68 (s, 1H), 7.19 (m, 2H), 6.47 (t, J=6 Hz, 1H), 2.95 (q, J=7 Hz, 2H), 1.48 (m, 2H), 1.33 (m, 2H), 0.85 (t, J=7 Hz, 3H). ¹³C NMR (d6-acetone): δ 165.96, 156.67, 145.87, 143.57, 140.64, 140.33, 133.75, 133.46, 127.82, 127.56, 127.38, 126.86, 126.02, 111.47, 105.79, 42.75, 31.53, 19.49, 12.97. LCMS m/z: [M–H]⁻ 494.5 (100%). LCMS m/z: [M+H]⁺ 496.8 (100%).

[3-Fluoro-4-({5-[4-(hydroxymethyl)phenyl]-1-benzofuran-2-yl}carbonyl)phenyl]boronic acid (APY-098)

Figure 20:
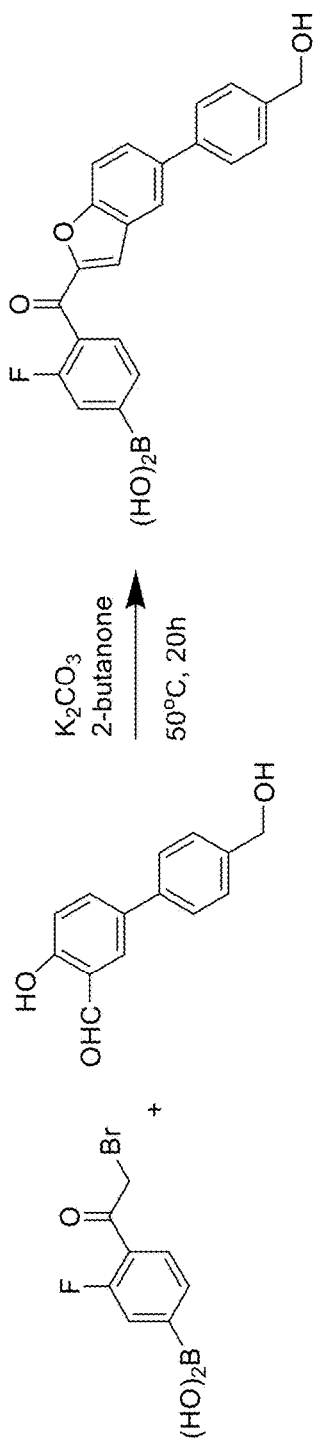
FIG. 20 depicts a chemical reaction diagram of the synthesis of [3-Fluoro-4-({5-[4-(hydroxymethyl)phenyl]-1-benzofuran-2-yl}carbonyl)phenyl)boronic acid (APY-098).

A stirred suspension of potassium carbonate (207 mg, 1.5 mmol) in methyl ethyl ketone (1 mL) under nitrogen was treated with a solution of 2-hydroxy-5-[4-(hydroxymethyl) phenyl]benzaldehyde (228 mg, 1 mmol) in 2-butanone (1 mL) and stirred 15 minutes. A solution of [4-(2-bromo-acetyl)-3-fluorophenyl]boronic acid (261 g, 1 mmol) in 2-butanone (3 mL) was added, and the mixture heated to 50° C. for 20 hours, cooled to room temperature, and diluted with water (20 mL). The aqueous suspension was stirred a few minutes, filtered, and the filter cake rinsed with water and air-dried. The solid was triturated from acetonitrile and dried in vacuo to afford 251 mg (64%) of [3-fluoro-4-({5-[4-(hydroxymethyl)phenyl]-1-benzofuran-2-yl}carbonyl) phenyl]boronic acid as a very pale yellow powder (FIG. 20). $^1$H NMR (d6-DMSO): δ 8.06 (m, 1H), 7.45-7.95 (m, 5H), 7.35 (m, 3H), 5.60-6.00 (m, 1H), 5.20 (m, 1H), 4.50 (m, 2H). $^{13}$C NMR (d6-DMSO): δ 155.49, 142.22, 138.65, 127.96, 127.53, 127.47, 127.15, 126.35, 121.99, 118.44, 113.10, 63.02, 60.21, 40.46, 21.21, 19.00, 14.53, 1.60. LCMS m/z: [M+H]$^+$ 391.4 (80%).

Synthesis of N-(2-(pyrrolidin-1-yl)ethyl)-2-(3,4,5-trihydroxybenzoyl)benzofuran-5-carboxamide (NED-2020)

Potassium carbonate (1.1 g, 7.78 mmol) was added to a solution of 5-(methoxycarbonyl)salicylaldehyde (935 mg, 5.19 mmol) in 2-butanone (30 ml) and the resulting suspension was stirred at room temperature under nitrogen for 30 minutes. A solution of 2-bromo-1-(3,4,5-trimethoxyphenyl) ethanone (Reddy et al., 2017, Bioorg Med Chem Lett, 27:1379-1384)[1] (1.5 g, 5.19 mmol) in 20 ml of 2-butanone was added to the above mixture. The reaction was heated to 50° C., stirred for 18 hours and cooled to room temperature. Water (150 ml) was added and the suspension was stirred for 10 minutes, filtered and rinsed with water to afford intermediate 1 as a white voluminous solid (1.5 g, 78%).

To a suspension of intermediate 1 (1 g, 2.70 mmol) in methanol (20 ml) was added dropwise 20% aqueous NaOH (5 ml), and stirring continued at 60° C. for 4 hours. After cooling to room temperature, the suspension was acidified to pH 3 with 2N HCl and a light yellow solid formed, which was collected by filtration, rinsed with water, and air dried to afford intermediate 2 (850 mg, 88%).

Intermediate 2 (500 mg, 1.40 mmol), 2-pyrrolidin-1-ylethanamine (320 mg, 2.80 mmol) and HOBt hydrate (322 mg, 2.11 mmol) were combined in dichloromethane (30 ml) under nitrogen, and the suspension was cooled on an ice bath and treated with triethylamine (0.58 mL, 4.21 mmol) and EDC hydrochloride (403 mg, 2.11 mmol). The solution was slowly warmed to room temperature and stirred overnight, concentrated in vacuo, and the residue dissolved in ethyl acetate (100 ml) and washed with water (2×100 ml) and brine (100 ml). The organic solution was dried (MgSO4) and concentrated in vacuo to afford a brown oil, which was purified by column chromatography on silica gel (eluted with 10% diethylamine/ethyl acetate) to yield intermediate 3 as white solid (460 mg, 72%).

Figure 21:
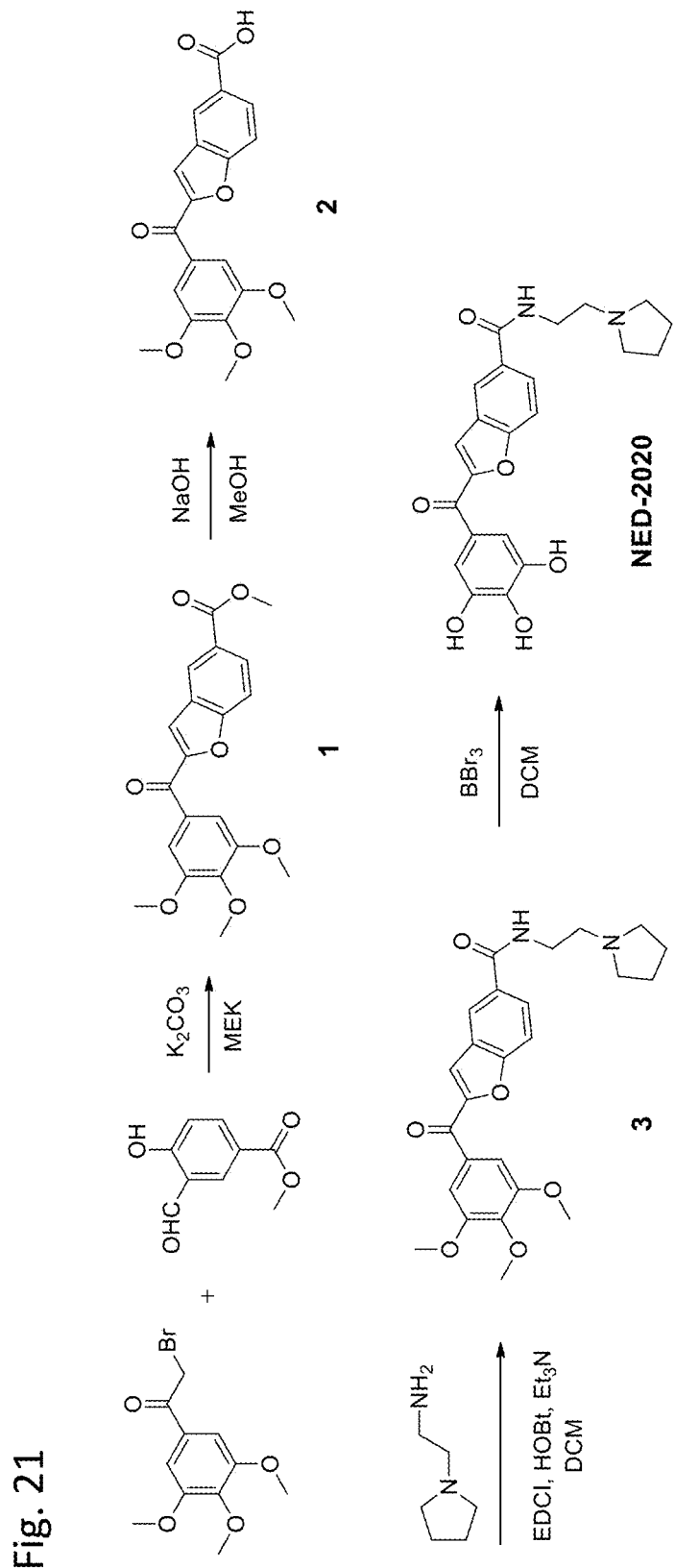
FIG. 21 depicts a chemical reaction diagram of the synthesis of N-(2-(pyrrolidin-1-yl)ethyl)-2-(3,4,5-trihydroxybenzoyl)benzofuran-5-carboxamide (NED-2020).

A cooled (−70° C.) stirred solution of intermediate 3 (400 mg, 0.88 mmol) in anhydrous dichloromethane (15 ml) under nitrogen was treated dropwise with 1N BBr$_3$/DCM (7.0 ml, 7.0 mmol). The reaction was allowed to warm to room temperature and stirred for 2 hours. The resultant dark orange suspension was cooled on an ice bath, quenched with saturated aqueous ammonium chloride (5 ml) and stirred for 1 hour. The precipitate was filtered and the solid washed with water (20 ml) and dichloromethane (20 ml), then dried, filtered and concentrated in vacuo to afford product NED-2020 as bright yellow solid (200 mg, 55%) (FIG. 21). $^1$H NMR (CD$_3$OD): δ 8.37 (d, J=1.8 Hz, 1H), 8.06 (dd, J=8.7, 1.9 Hz, 1H), 7.73 (d, J=8.7 Hz, 1H), 7.67 (s, 1H), 7.19 (s, 2H), 3.85-3.81 (m, 2H), 3.80 (t, J=5.9 Hz, 2H), 3.49 (t, J=5.9 Hz, 2H), 3.20-3.18 (m, 2H), 2.21-2.18 (m, 2H), 2.07-2.04 (m, 2H). $^{13}$C NMR (CD$_3$OD): δ 184.2, 170.5, 158.7, 155.2, 146.8, 141.0, 131.0, 128.52, 128.5, 128.4, 124.5, 116.6, 113.2, 110.6, 56.1, 55.7, 37.6, 24.0. LCMS (m/z): 410.3 (100%).

The results of the experiments are now described.

Figure 22A:
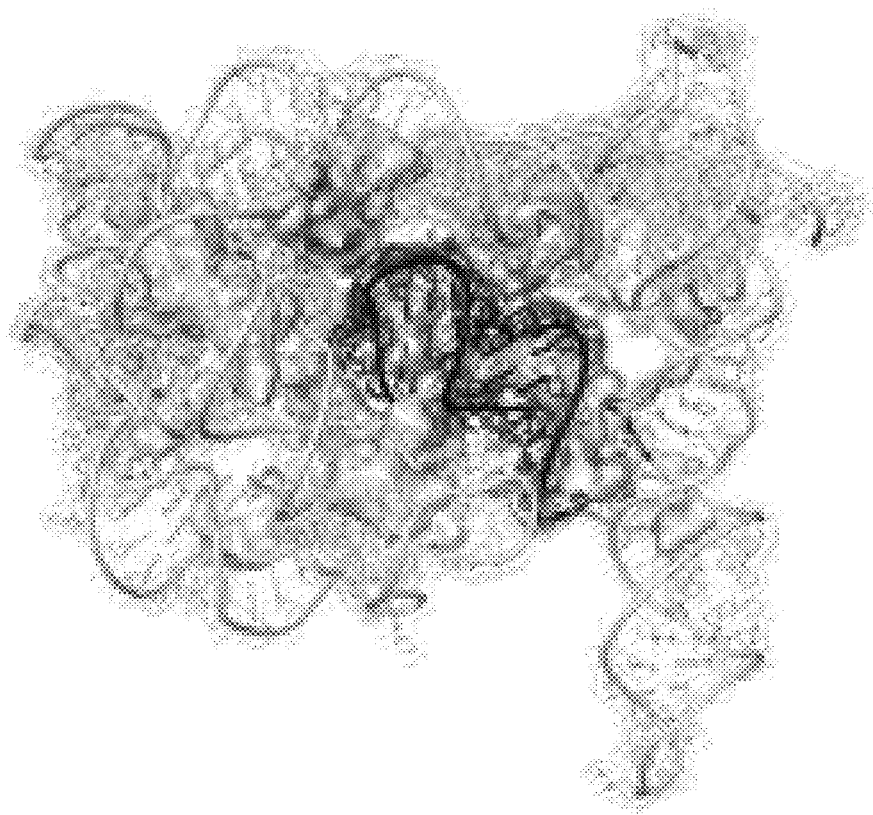
FIGS. 22A-22C depict the RNA target and assays for compound development.
Figure 22B:
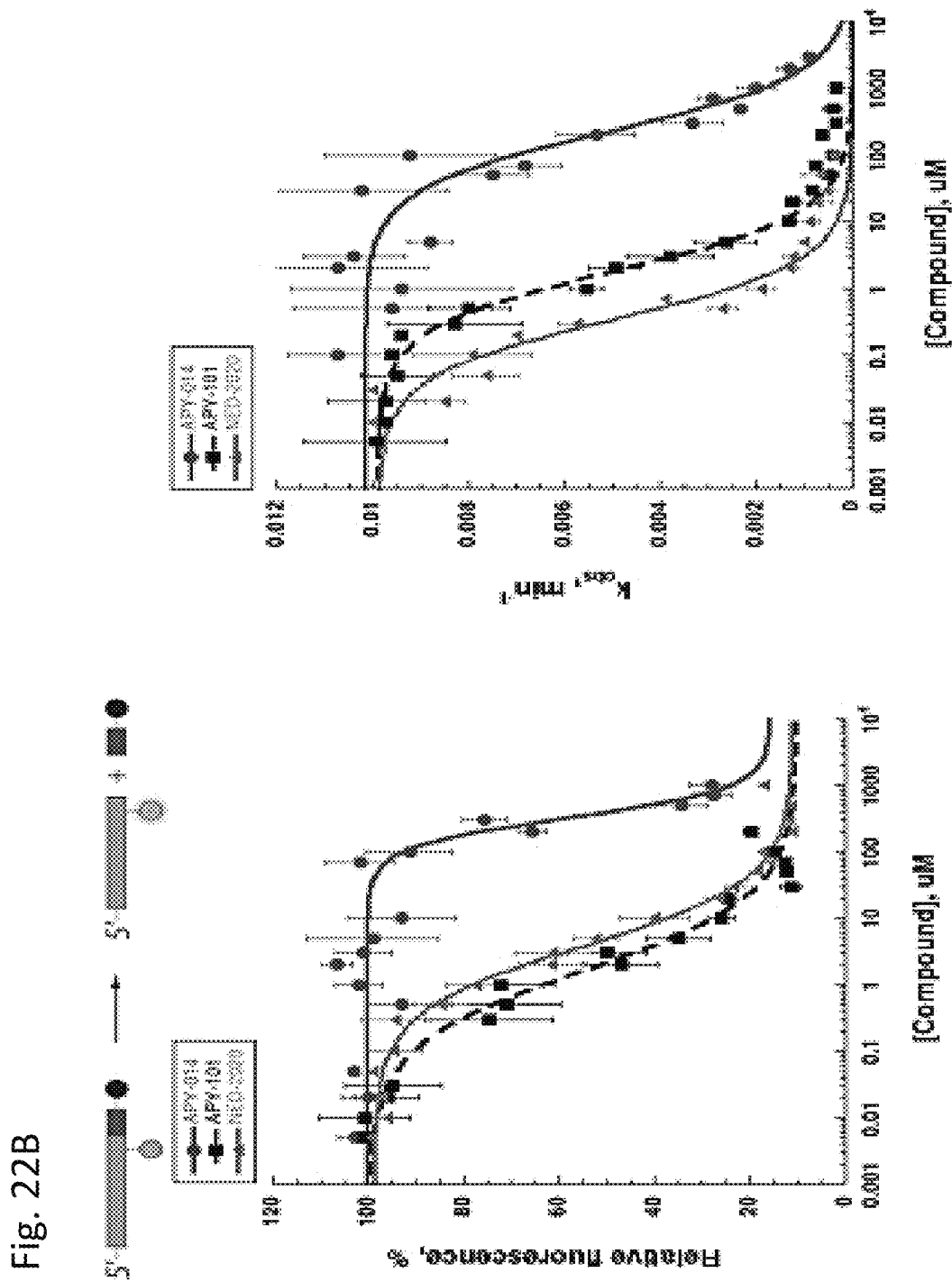

Group II introns, are large self-splicing ribozymes that are found in the mitochondrial genomes of plants, fungi, and yeast, but are not present in mammals. These autocatalytic RNA molecules adopt an elaborate tertiary structure that has been crystallographically characterized and which contains an active-site for RNA cleavage and ligation as well as solvent-accessible pockets for potential inhibitor binding (Toor et al., 2008, Science, 320:77-82; Toor et al., 2010, RNA, 16:57-69) (FIG. 22A). In yeasts such as *Saccharomyces cerevisiae* (*S. cerevisiae*) and the pathogen *Candida parapsilosis* (*C. parapsilosis*), group II introns are found within genes that are essential for respiration, such as cytochrome oxidase subunit genes of the mitochondria. Importantly, respiration is essential for pathogenic yeast to differentiate into biofilms, which colonize medical implant surfaces, are relatively resistant to antifungals, and contribute to pathogenic virulence (Morales et al., 2013, MBio, 4:e00526-00512; Richard et al., 2005, Eukaryot Cell, 4:1493-1502). Thus, based on the complexity of their structures, and their essential role in fungal metabolism, group II introns represent outstanding targets for the development of highly specific antifungal agents.

To identify group II intron splicing inhibitors, a high-throughput screening-compatible fluorescent assay was developed for monitoring ribozyme activity of the well-characterized ai5γ group II intron from *S. cerevisiae* (FIG. 23A, FIGS. 1A-1D, FIG. 22B). Using this assay, a curated library of 10,000 compounds was screened, identifying 16 reproducible hits. Interestingly, a third of these hits contained a gallate moiety within the molecular structure (FIG. 1D), suggesting that this functionality might contribute to inhibitory activity. A series of commercially available analogs of the major hits was analyzed in order to identify more suitable scaffolds for further optimization. The most potent scaffold identified during this phase of the study was compound 1, which exhibited an IC$_{50}$ of 2 μM, (CAS 3260-50-2, FIG. 24, Table 2). It was used as a starting point for the design of additional compounds that were used to define structure-activity relationships (SAR) and to optimize potency (Table 2).

In Vitro SAR and Optimization of Potency

Figure 22C:
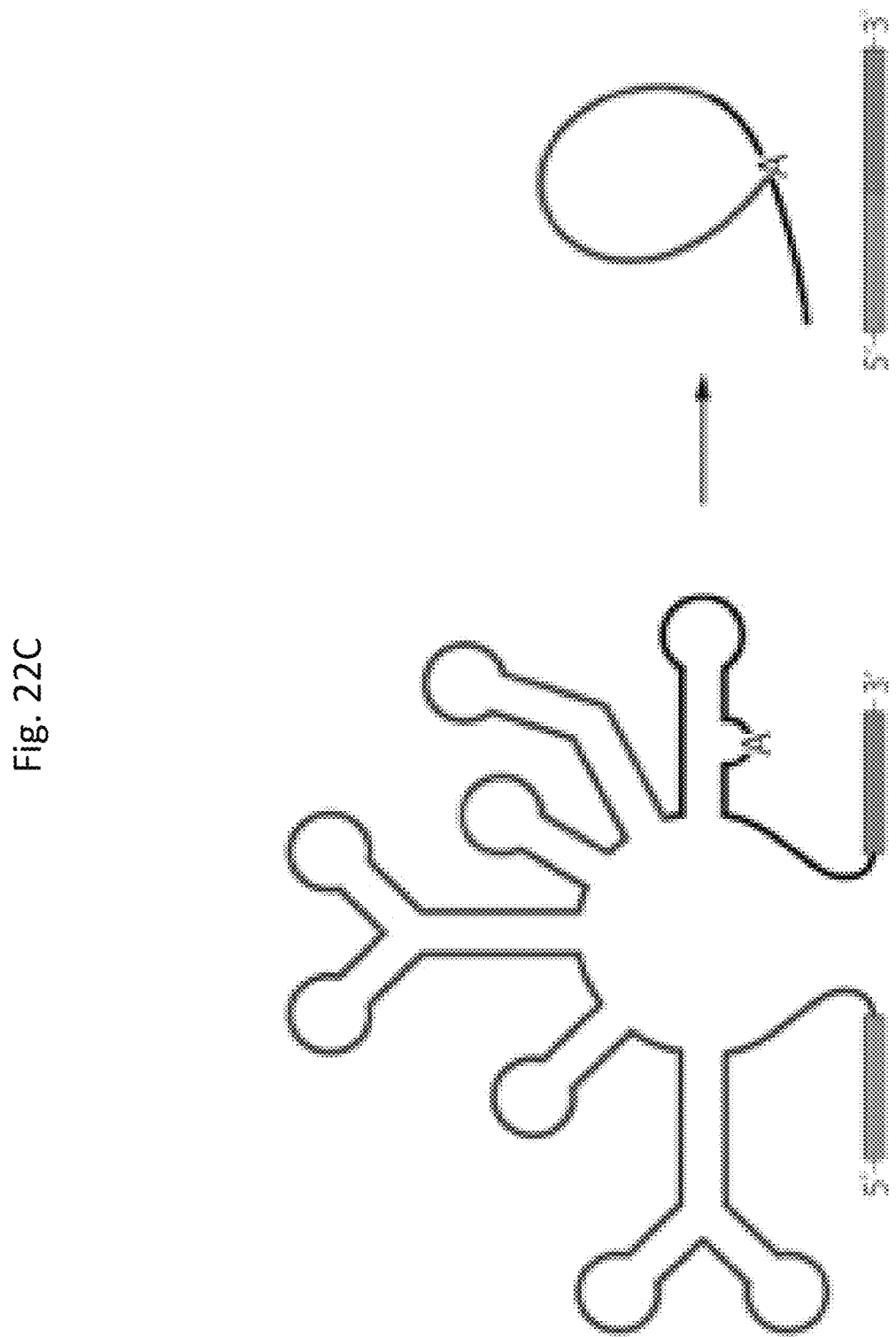
Figure 25A:
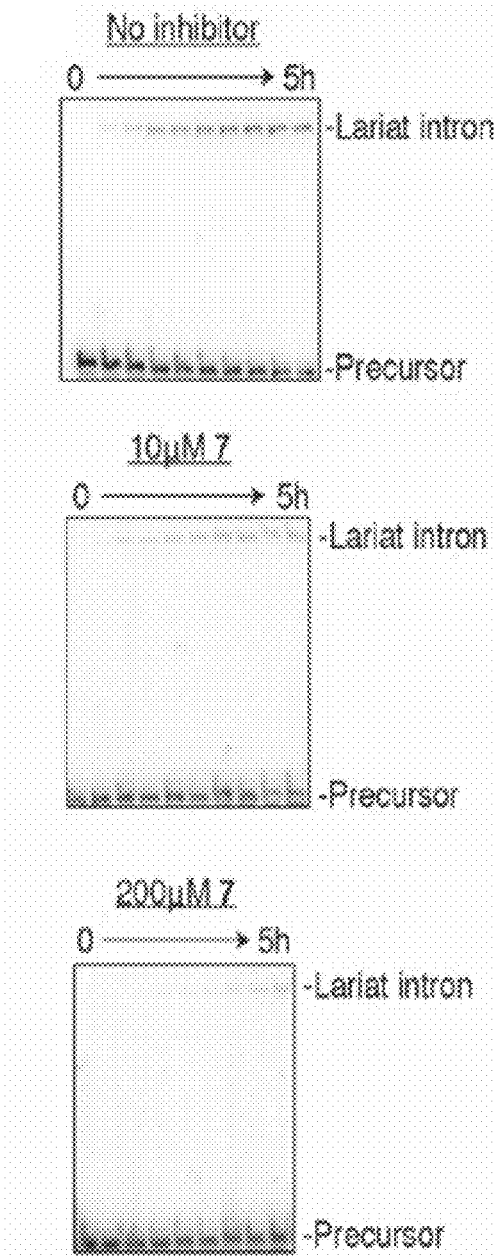
Figure 25B:
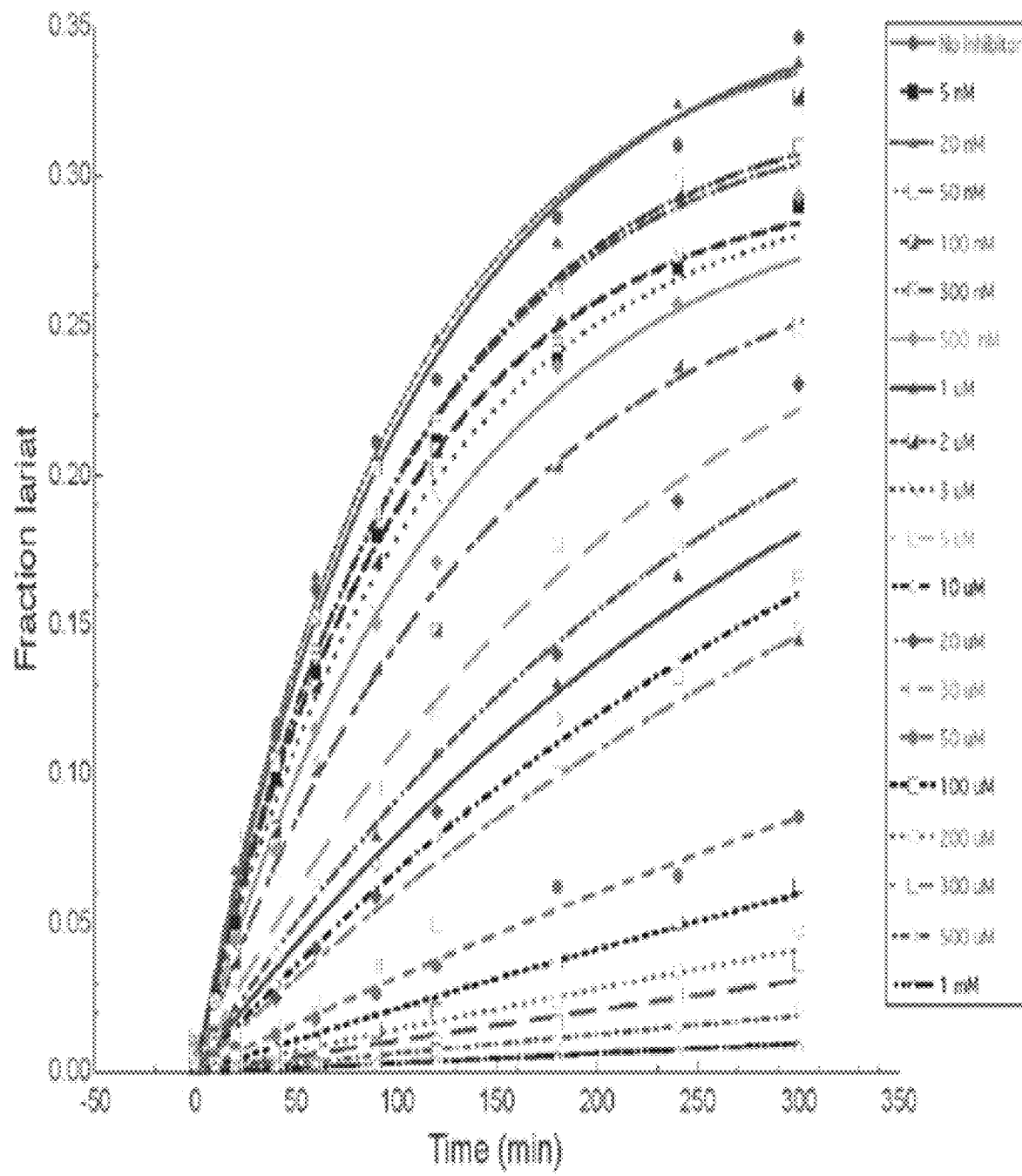
Figure 25C:
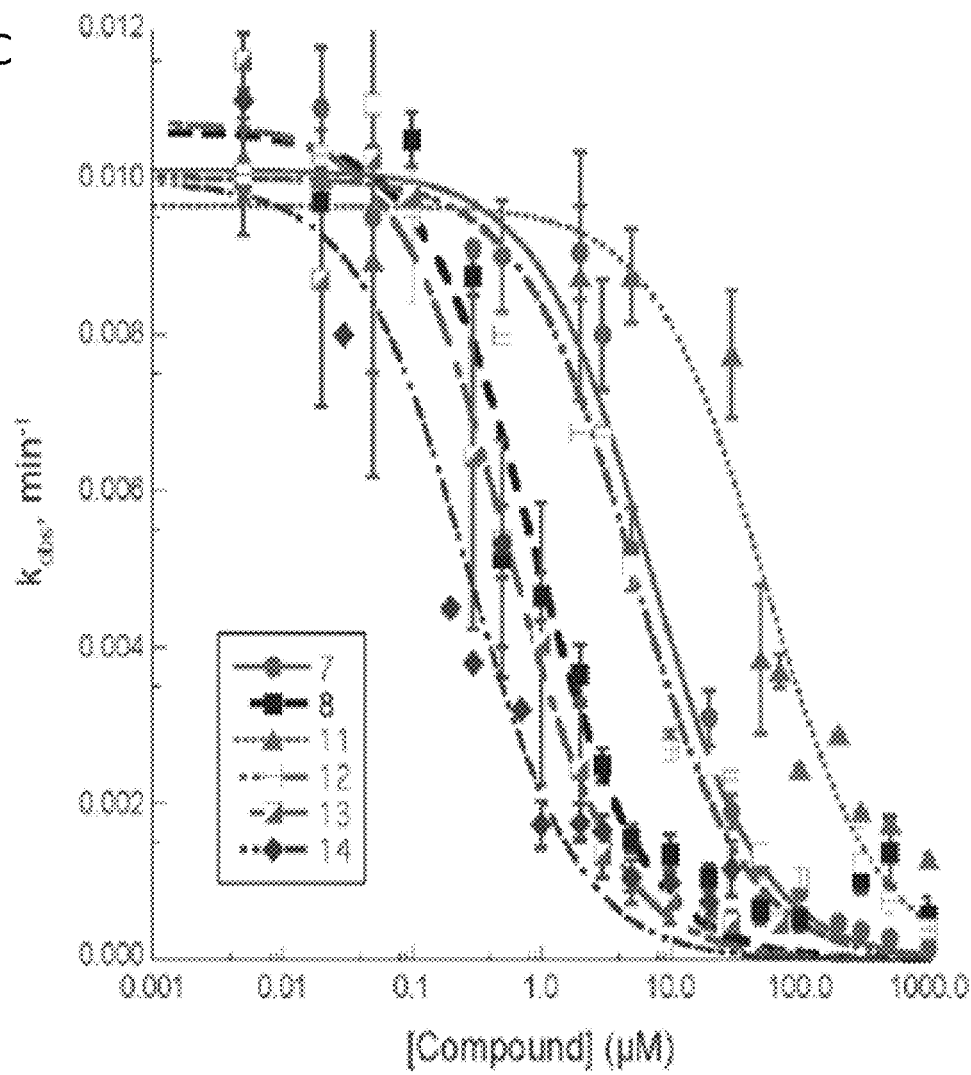

The primary fluorimetric assay was complemented by a robust secondary radioanalytic self-splicing assay of the precursor RNA containing the full length ai5γ intron and short exons, which enabled the determination of K$_i$ values for all compounds of interest (FIG. 22C, FIGS. 25A-Table 2).

Figure 24:
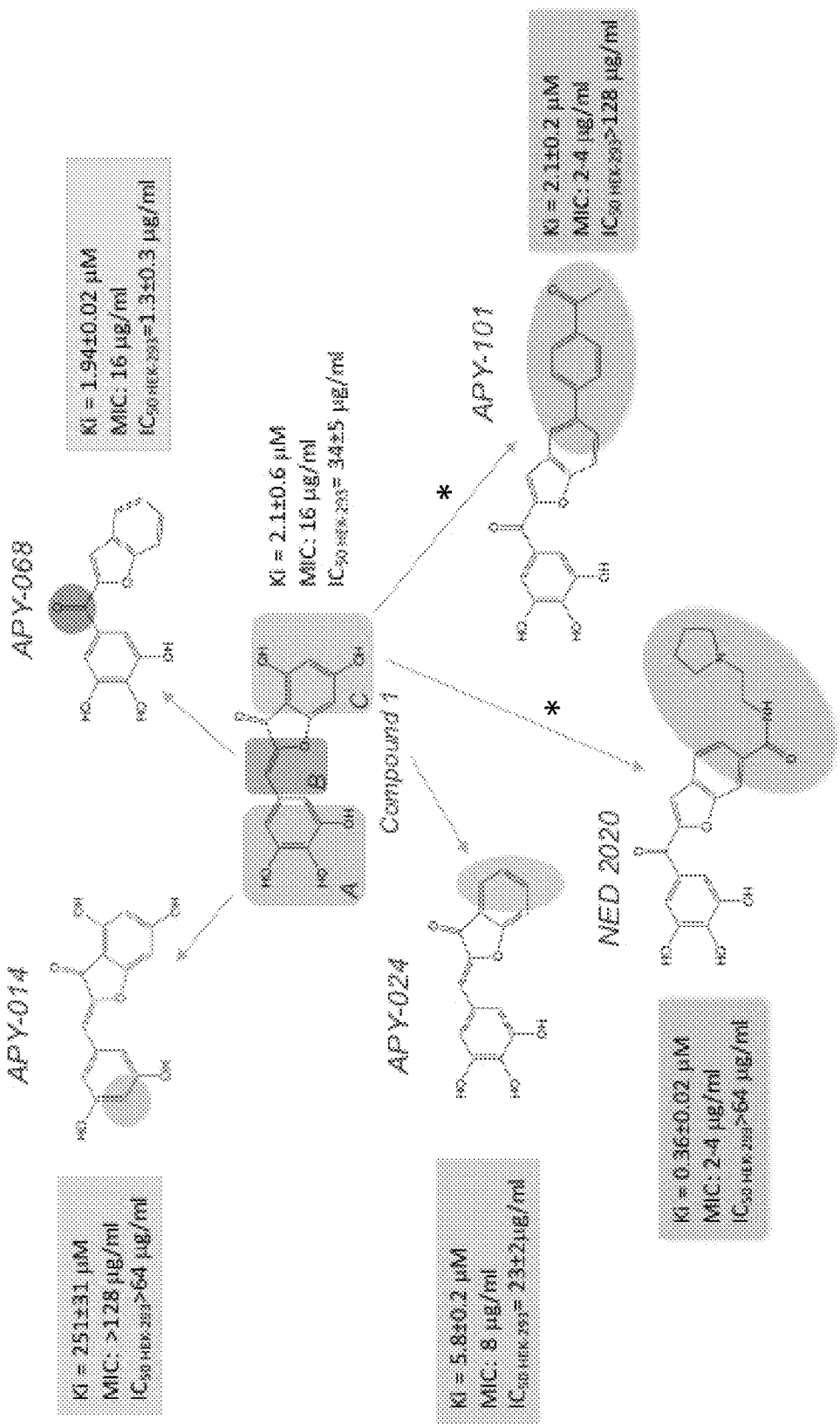
FIG. 24 depicts a summary of structure-activity relationships (SAR) studies on Compound 1. In vitro splicing inhibition constants ($K_i$) for the S.c. ai5γ intron, MIC values for *C. parapsilosis* group II intron and $IC_{50}$ values for cytotoxicity in HEK-293 cells are shown next to each molecule. Changes that were introduced for optimization of inhibitory activity are indicated with an asterisk (*).

As part of an initial strategy to optimize the early leads, a series of compounds was selected to determine the critical structural components required for activity: the pharmacophore. Three regions of CAS 3260-50-2 (A, B and C) were defined and substituents in these sections of the molecule were evaluated for their effect on inhibition (FIG. 24). In region A, replacing any of the hydroxyl groups with hydrogen or methoxy or boronic acid substituents (compounds APY-007, APY-014, APY-001, APY-098; Table 2.) all resulted in nearly complete loss of activity. Notably, when the trihydroxyl was replaced with a dihydroxyl catechol moiety, the molecule was inactivated both in vitro and in vivo (APY-007, Table 2), indicating that presence of the catechol motif by itself cannot explain reactivity of the group II intron inhibitors, unlike certain classes of promiscuous molecules that are collectively classified as "PAINS" compounds.

In contrast, each of the hydroxyl groups in region C could be removed or replaced with halogen atoms without significant loss of function (compounds APY-019, APY-024, APY-083, FIG. 24, Table 2). To minimize any risk of reactivity from the α,β-unsaturated ketone, the 2-benzylidenebenzofuran-3(2H)-one moiety was replaced with a more chemically and metabolically stable benzofuran-2-yl(phenyl)methanone (region B), This more drug-like molecular template resulted in a 2-fold increase in in vitro potency (APY-068, FIG. 24, Table Other attempts to introduce changes in this region (for example, amide or thiazole derivatives) resulted in a substantial loss of activity (compounds APY-077 and APY-093, Table 2). The fact that potency was sensitive to certain modifications in Region B, and in distal parts of Region C (Table 2), indicates that inhibitory activity is not solely attributable to functional groups in Region A.

With the new lead structure (APY-068) in hand, additional substituents were added to the benzofuran moiety to further develop the structure-activity relationship for the series. Introduction of a wide variety of substituents, including aryl, heteroaryl, amino or halogens at the 5' or 6'-positions were all generally tolerated (compounds APY-083, APY-081, APY-084, APY-090, APY-091, APY-094, APY-097, Intronistat A, and Intronistat B, FIG. 24, Table 2). Notably, the data suggest that adding large substituents or positively charged residues to region C can increase inhibitory activity (lower the $K_i$) of the respective compounds (FIG. 24, Table 2), Examples of such effects are observed for compounds APY-084, APY-090 and NED-2020 (FIG. 24, Table 2).

Reversibility of inhibitor binding to the intron was established using pulse-chase dilution experiments (FIG. 25D). The clear reactivity patterns evident from this SAR analysis, together with facile reversibility of compound binding and inhibition are consistent with selective behavior.

TABLE 2

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, µM | $K_i$ ai5γ intron, µM | MIC *C. parapsilosis*, µg/ml | $IC_{50}$ HEK-293, µg/ml |
|---|---|---|---|---|---|---|
| APY-001 | 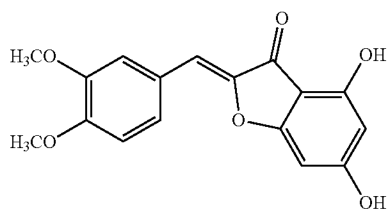 [SMILES: COc1ccc(/C=C2\Oc3cc(O)cc(O)c3C2=O)cc1OC] | 314.29 | >100[1] | >1000 | >128 | >128 |
| Compound 1 (CAS 3260-50-2) | 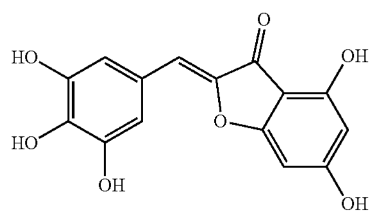 [SMILES: O=C1/C(=C/c2cc(O)c(O)c(O)c2)Oc2cc(O)cc(O)c21] | 302.24 | 2.3 ± 0.4 | 2.1 ± 0.6 | *16* | 34 ± 5 |
| APY-007 | 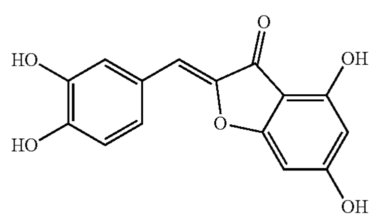 [SMILES: O=C1/C(=C/c2ccc(O)c(O)c2)Oc2cc(O)cc(O)c21] | 286.24 | >100[1] | 156 ± 34 | >128 | >128 |
| APY-014 | 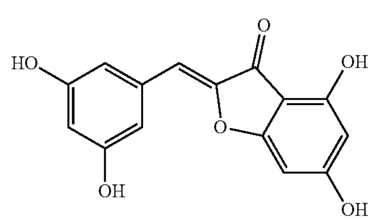 [SMILES: O=C1/C(=C/c2cc(O)cc(O)c2)Oc2cc(O)cc(O)c21] | 286.24 | 266 ± 37 | 251 ± 31 | >128 | >64 |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, µM | $K_i$ ai5γ intron, µM | MIC *C. parapsilosis*, µg/ml | $IC_{50}$ HEK-293, µg/ml |
|---|---|---|---|---|---|---|
| APY-019 | 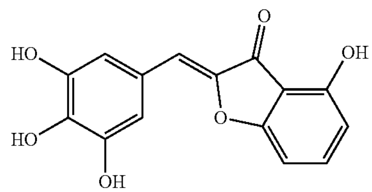 [SMILES: O=C1/C(=C/c2cc(O)c(O)c(O)c2)Oc2cccc(O)c21] | 286.24 | 8 ± 2 | 4.4 ± 0.4 | *16* | >32 |
| APY-024 | 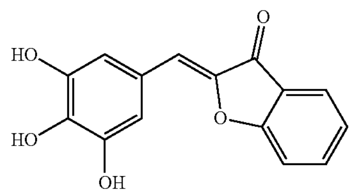 [SMILES: O=C1/C(=C/c2cc(O)c(O)c(O)c2)Oc2ccccc21] | 270.24 | 7 ± 1 | 5.8 ± 0.2 | *8* | 23 ± 2 |
| APY-068 | 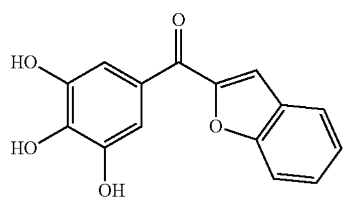 [SMILES: O=C(c1cc(O)c(O)c(O)c1)c1cc2ccccc2o1] | 270.24 | 3.7 ± 0.6 | 1.94 ± 0.02 | *16* | 1.3 ± 0.3 |
| APY-077 | 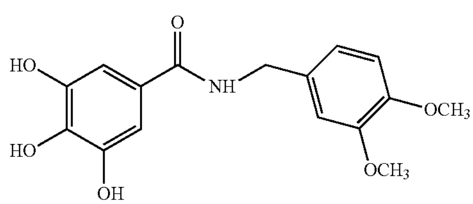 [SMILES: COc1ccc(CNC(=O)c2cc(O)c(O)c(O)c2)cc1OC] | 319.31 | 30 ± 4 | 44 ± 11 | *64* | >32 |
| APY-081 | 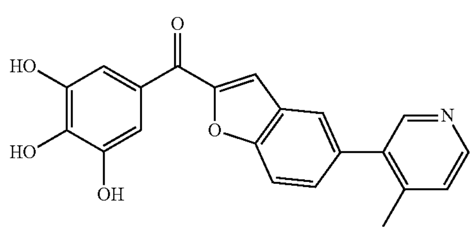 [SMILES: Cc1ccncc1-c1ccc2oc(C(=O)c3cc(O)c(O)c(O)c3)cc2c1] | 349.13 | 6.8 ± 1.1 | 5.3 ± 0.2 | *4-8* | >128 |
| APY-083 | 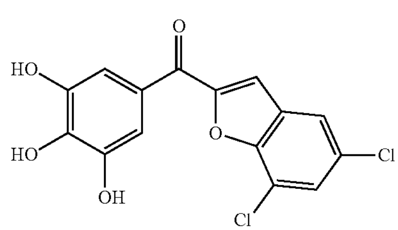 [SMILES: O=C(c1cc(O)c(O)c(O)c1)c1cc2cc(Cl)cc(Cl)c2o1] | 339.13 | 3.3 ± 0.3 | 0.9 ± 0.1 | *8* | 0.5 ± 0.1 |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| APY-084 | 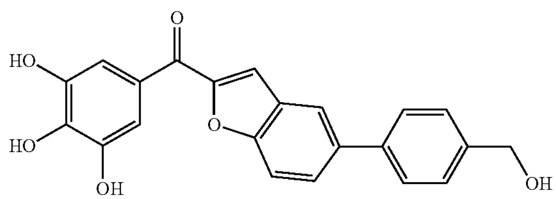 [SMILES: O=C(c1cc(O)c(O)c(O)c1)c1cc2cc(-c3ccc(CO)cc3)ccc2o1] | 376.36 | 0.9 ± 0.1 | 1.3 ± 0.4 | *2-4* | 1.1 ± 0.1 |
| APY-090 | 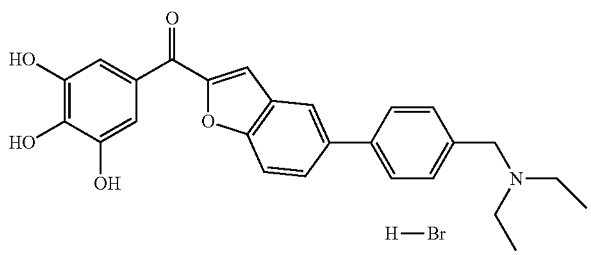 | 512.39 | 2.1 ± 0.4 | 0.37 ± 0.04 | *4-8* | 1.7 ± 0.6 |
| APY-091 | 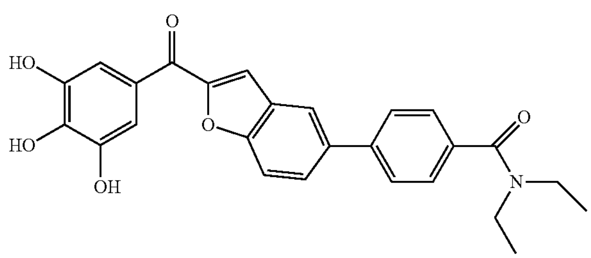 [SMILES: CCN(CC)C(=O)c1ccc(-c2ccc3oc(C(=O)c4cc(O)c(O)c(O)c4)cc3c2)cc1] | 445.46 | 2.4 ± 0.4 | 4.5 ± 0.9 | *8* | 5.35 ± 0.05 |
| APY-093 | 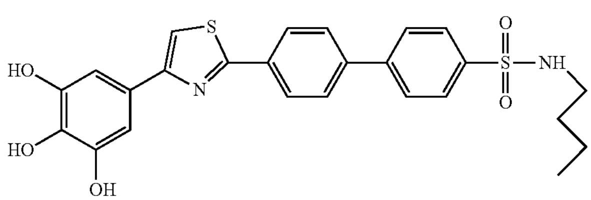 [SMILES: CCCCNS(=O)(=O)c1ccc(-c2ccc(-c3nc(-c4cc(O)c(O)c(O)c4)cs3)cc2)cc1] | 496.6 | 86 ± 3 | 53 ± 5 | *32-64* | 7.2 ± 1.5 |
| APY-094 | 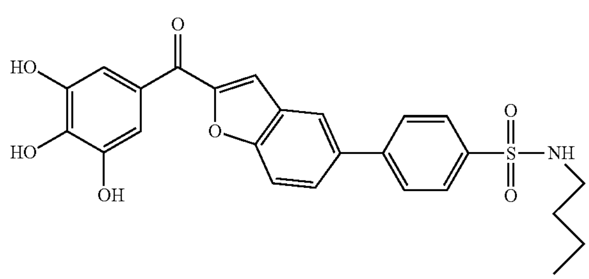 [SMILES: CCCCNS(=O)(=O)c1ccc(-c2ccc3oc(C(=O)c4cc(O)c(O)c(O)c4)cc3c2)cc1] | 481.52 | 9.9 ± 0.7 | 3.39 ± 0.01 | *8-16* | 15 ± 4 |
| APY-097 | 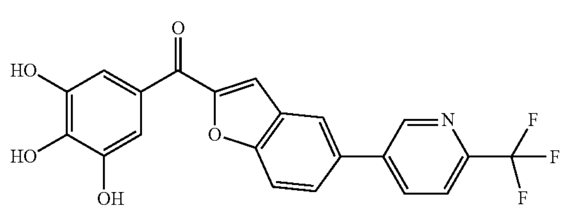 [SMILES: O=C(c1cc(O)c(O)c(O)c1)c1cc2cc(-c3ccc(C(F)(F)F)nc3)ccc2o1] | 415.2 | 2.8 ± 0.2 | 3.9 ± 0.5 | *8* | 5.4 ± 0.6 |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| APY-098 | 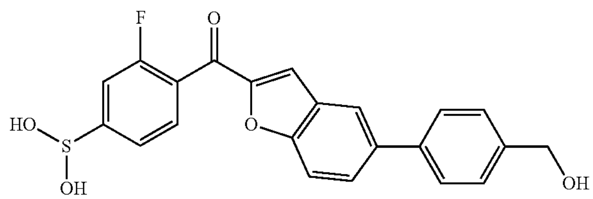 | 390.17 | >1000 | >1000 | >128 | 11 ± 3 |
| APY-101 (Intronistat B) | 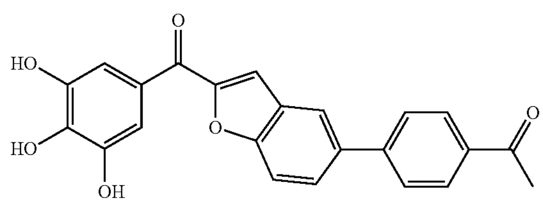 [SMILES: CC(=O)c1ccc(-c2ccc3oc(C(=O)c4cc(O)c(O)c(O)c4)cc3c2)cc1] | 388.37 | 1.5 ± 0.1 | 2.1 ± 0.2 | *2-4* | >128 |
| NED-2020 (Intronistat B) | 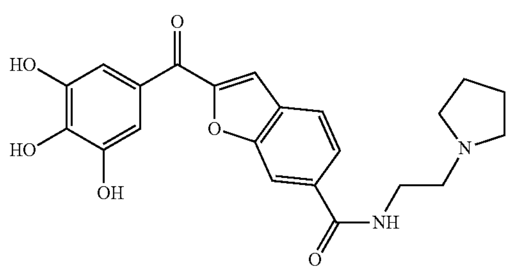 [SMILES: O=C(NCCN1CCCC1)c1ccc2cc(C(=O)c3cc(O)c(O)c(O)c3)oc2c1] | 410.43 | 3.8 ± 0.5 | 0.36 ± 0.02 | *2-4* | >64 |
| "Compound 2" | 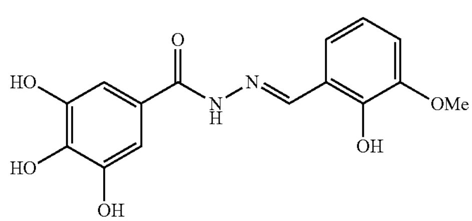 [SMILES: COc1cccc(/C=N/NC(=O)c2cc(O)c(O)c(O)c2)c1O] | 318.28 | 7.3 | 8 | 32 | 34 |
| APY-003 | 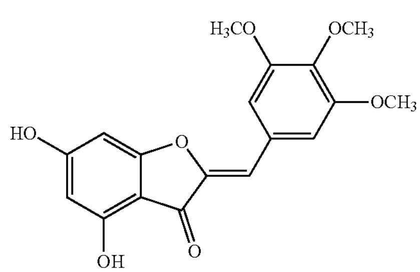 [SMILES: COc1cc(/C=C2\Oc3cc(O)cc(O)c3C2=O)cc(OC)c1OC] | 344.32 | >500 | | >128 | >64 |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| APY-006 | 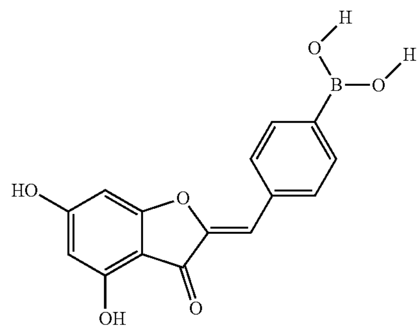 [SMILES: O=C1/C(=C/c2ccc(B(O)O)cc2)Oc2cc(O)cc(O)c21] | 298.06 | not determined | 55 | | |
| APY-010 | 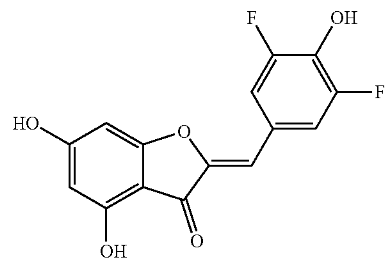 [SMILES: O=C1/C(=C/c2cc(F)c(O)c(F)c2)Oc2cc(O)cc(O)c21] | 306.22 | not determined | 140 | >128 | 0.55 |
| APY-012 | 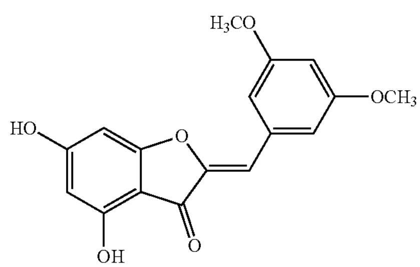 [SMILES: COc1cc(/C=C2\Oc3cc(O)cc(O)c3C2=O)cc(OC)c1] | 314.29 | >500 | | >128 | |
| APY-013 | 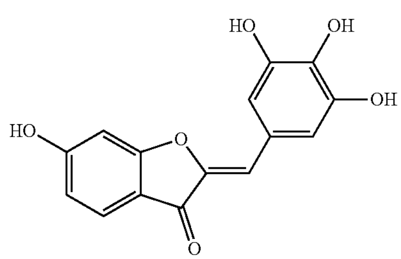 [SMILES: O=C1/C(=C/c2cc(O)c(O)c(O)c2)Oc2cc(O)ccc21] | 286.24 | 16.7 | 16.5 | 32 | 19 |
| APY-018 | 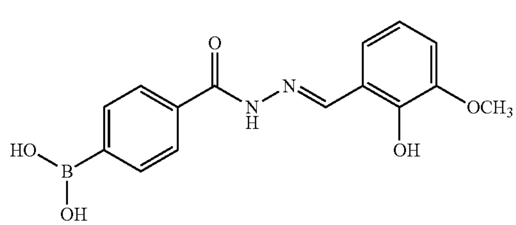 [SMILES: COc1cccc(/C=N/NC(=O)c2ccc(B(O)O)cc2)c1O] | 314.1 | not determined | 660 | | |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| APY-021 | 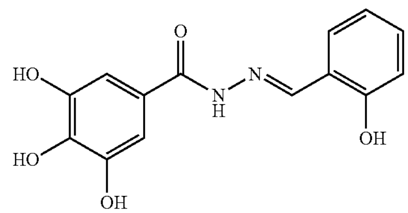 [SMILES: O=C(N/N=C/c1ccccc1O)c1cc(O)c(O)c(O)c1] | 288.26 | 14 | 9.4 | 32 | |
| APY-022 | 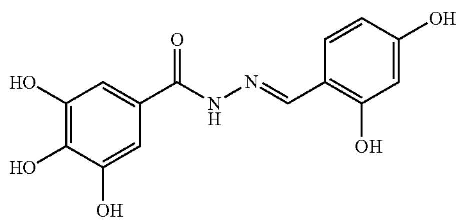 | 304.26 | 5.5 | 6.5 | 32 | 17.6 |
| APY-031 | 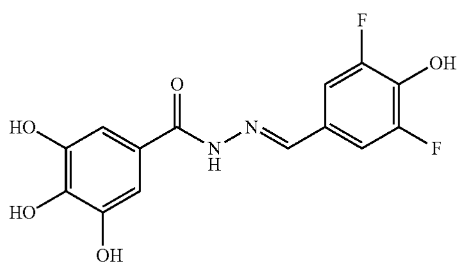 [SMILES: O=C(N/N=C/c1cc(F)c(O)c(F)c1)c1cc(O)c(O)c(O)c1] | 324.24 | 6.3 | | 32 | 47.8 |
| APY-032 | 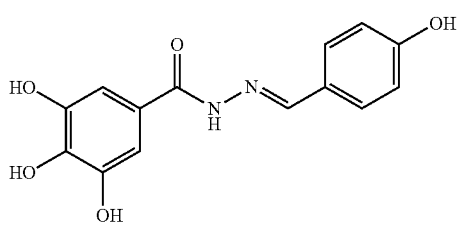 [SMILES: O=C(N/N=C/c1ccc(O)cc1)c1cc(O)c(O)c(O)c1] | 288.26 | 10.6 | | 8 | 4.14 |
| APY-033 | 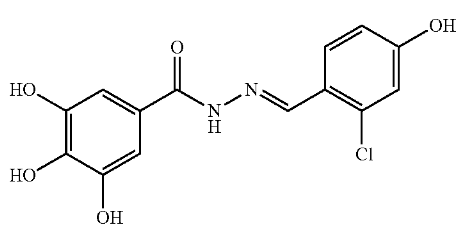 [SMILES: O=C(N/N=C/c1ccc(O)cc1Cl)c1cc(O)c(O)c(O)c1] | 322.7 | 6.5 | | 8 | 50 |
| APY-034 | 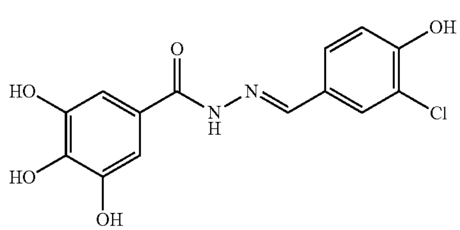 [SMILES: O=C(N/N=C/c1ccc(O)c(Cl)c1)c1cc(O)c(O)c(O)c1] | 322.7 | 4.7 | | 8 | 54.5 |

TABLE 2-continued

Structure-activity relationships of representative Group II intron inhibitors. In vitro data (IC$_{50}$ and K$_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | IC$_{50}$ ai5γ intron, μM | K$_i$ ai5γ intron, μM | MIC *C. parapsilosis*, μg/ml | IC$_{50}$ HEK-293, μg/ml |
|---|---|---|---|---|---|---|
| APY-035 | 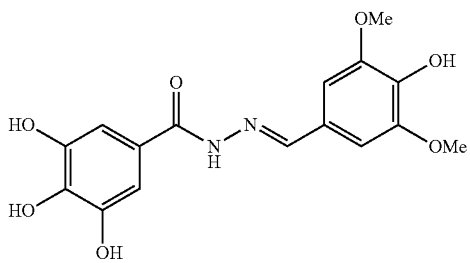 [SMILES: COc1cc(/C=N/NC(=O)c2cc(O)c(O)c(O)c2)cc(OC)c1O] | 348.31 | 7.7 | | 4 | 39.3 |
| APY-036 | 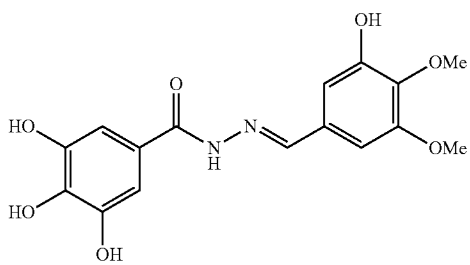 [SMILES: COc1cc(/C=N/NC(=O)c2cc(O)c(O)c(O)c2)cc(O)c1OC] | 348.31 | 7.7 | | 4 | 10.4 |
| APY-037 | 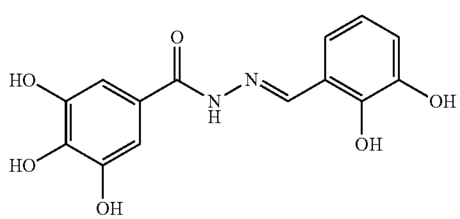 [SMILES: O=C(N/N=C/c1cccc(O)c1O)c1cc(O)c(O)c(O)c1] | 304.26 | 3.7 | | 8 | 5.4 |
| APY-038 | 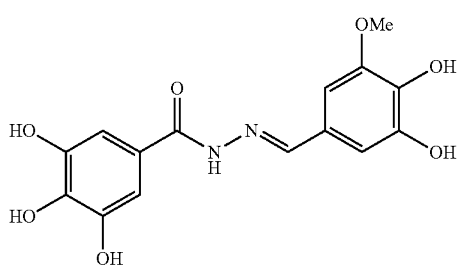 [SMILES: COc1cc(/C=N/NC(=O)c2cc(O)c(O)c(O)c2)cc(O)c1O] | 334.28 | 1.3 | 1.1 | 8 | 15.9 |
| APY-040 | 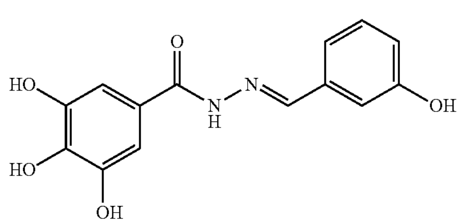 [SMILES: O=C(N/N=C/c1cccc(O)c1)c1cc(O)c(O)c(O)c1] | 288.26 | 9.9 | | 8 | 30.1 |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| APY-041 | 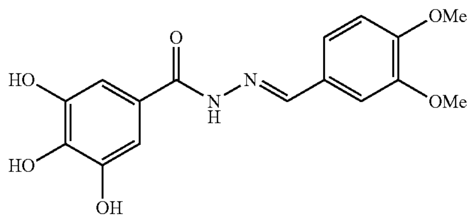 [SMILES: COc1ccc(/C=N/NC(=O)c2cc(O)c(O)c(O)c2)cc1OC] | 332.31 | 3.8 | | 8 | 49.5 |
| APY-054 | 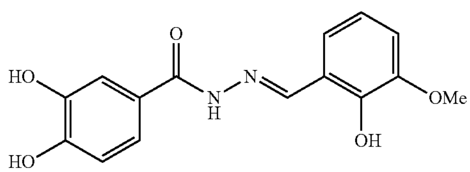 [SMILES: COc1cccc(/C=N/NC(=O)c2ccc(O)c(O)c2)c1O] | 302.29 | >500 | | >128 | >64 |
| APY-056 | 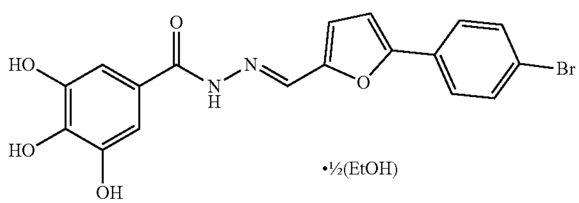 [SMILES: O=C(N/N=C/c1ccc(-c2ccc(Br)cc2)o1)c1cc(O)c(O)c(O)c1] | fw = 440.24 | 2.7 ± 0.5 | 1.7 | 32 | 1.1 |
| APY-057 | 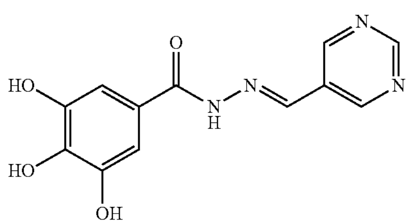 [SMILES: O=C(N/N=C/c1cncnc1)c1cc(O)c(O)c(O)c1] | 274.24 | 12.9 | | 16 | 39.4 |
| APY-058 | 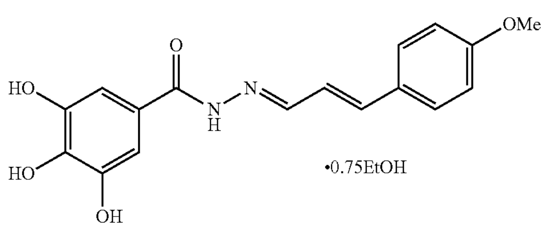 [SMILES: COc1ccc(/C=C/C=N/NC(=O)c2cc(O)c(O)c(O)c2)cc1] | fw = 362.87 | 10.1 | | 4 | 23 |
| APY-069 | 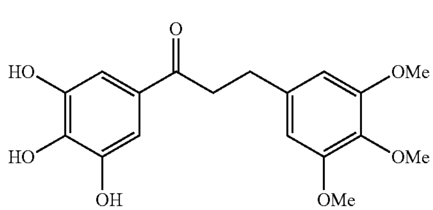 [SMILES: COc1cc(CCC(=O)c2cc(O)c(O)c(O)c2)cc(OC)c1OC] | 348.35 | 27 | 29 | 32 | >128 |

TABLE 2-continued

Structure-activity relationships of representative Group II intron inhibitors. In vitro data (IC$_{50}$ and K$_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | IC$_{50}$ ai5γ intron, μM | K$_i$ ai5γ intron, μM | MIC *C. parapsilosis*, μg/ml | IC$_{50}$ HEK-293, μg/ml |
|---|---|---|---|---|---|---|
| APY-070 | 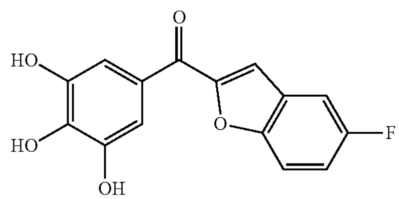 [SMILES: O=C(c1cc(O)c(O)c(O)c1)c1cc2cc(F)ccc2o1] | 288.23 | 4.2 | 1 | 32 | >128 |
| APY-071 | 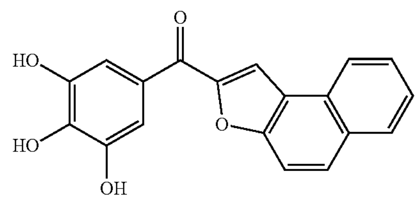 [SMILES: O=C(c1cc(O)c(O)c(O)c1)c1cc2c(ccc3ccccc32)o1] | 320.3 | 0.3 | 0.15 | 16 | 6 |
| APY-076 | 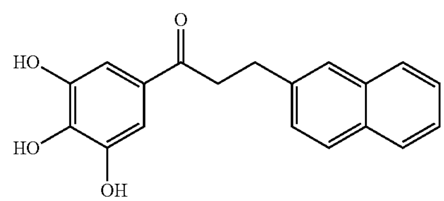 [SMILES: O=C(CCc1ccc2ccccc2c1)c1cc(O)c(O)c(O)c1] | 308.33 | 8 | 5.4 | 16 | 7 |
| APY-078 | 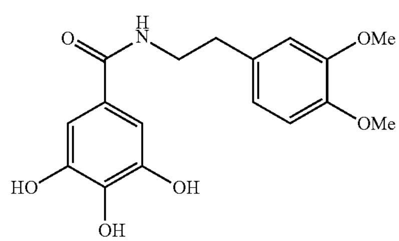 [SMILES: COc1ccc(CCNC(=O)c2cc(O)c(O)c(O)c2)cc1OC] | 333.34 | 27 | 16 | 64 | >128 |
| APY-079 | 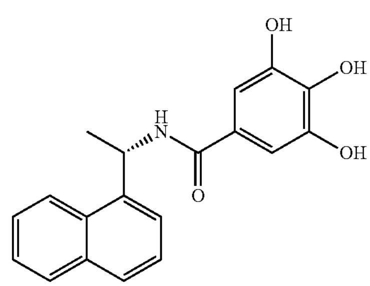 [SMILES: C[C@H](NC(=O)c1cc(O)c(O)c(O)c1)c1cccc2ccccc12] | 323.34 | 20 | 32 | 32 | 4.6 |
| APY-085 | 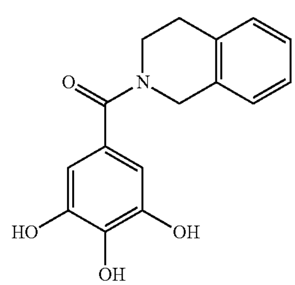 [SMILES: O=C(c1cc(O)c(O)c(O)c1)N1CCc2ccccc2C1] | 285.29 | 6.4 | | 32 | 18.7 |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| APY-086 | 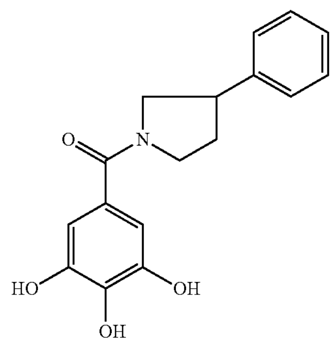 [SMILES: O=C(c1cc(O)c(O)c(O)c1)N1CCC(c2ccccc2)C1] | 299.32 | 61 | | 64 | 43.7 |
| APY-087 | 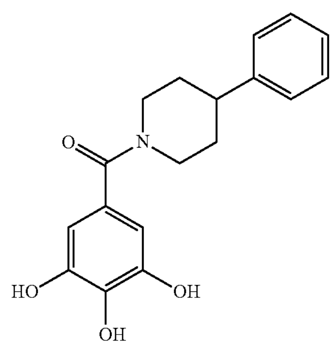 [SMILES: O=C(c1cc(O)c(O)c(O)c1)N1CCC(c2ccccc2)CC1] | 313.35 | 79 | | 32 | 8.4 |
| APY-088 | 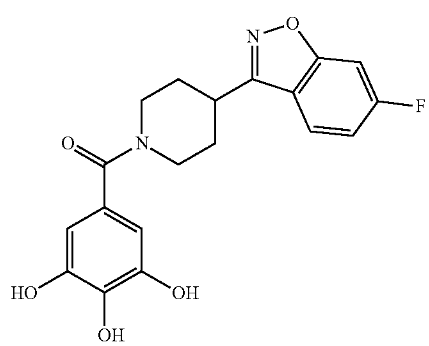 [SMILES: O=C(c1cc(O)c(O)c(O)c1)N1CCC(c2noc3cc(F)ccc23)CC1] | 372.35 | 24 | | 16 | 6.55 |
| APY-092 | 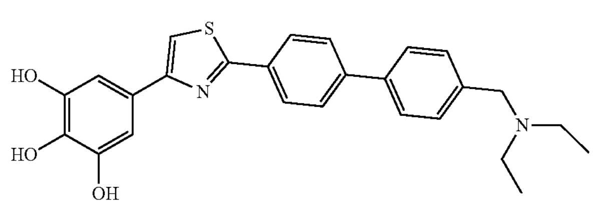 [SMILES: CCN(CC)Cc1ccc(-c2ccc(-c3nc(-c4cc(O)c(O)c(O)c4)cs3)cc2)cc1] | 446.56 | 1.3 | | 16 | 24.8 |
| APY-095 | 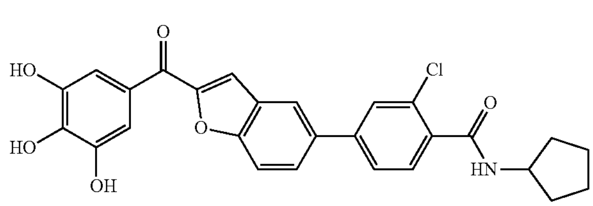 [SMILES: O=C(c1cc(O)c(O)c(O)c1)c1cc2cc(-c3ccc(C(=O)NC4CCCC4)c(Cl)c3)ccc2o1] | 491.92 | inconclusive (fluorescent molecule) | | 4-8 | 2.5 |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| APY-096 | 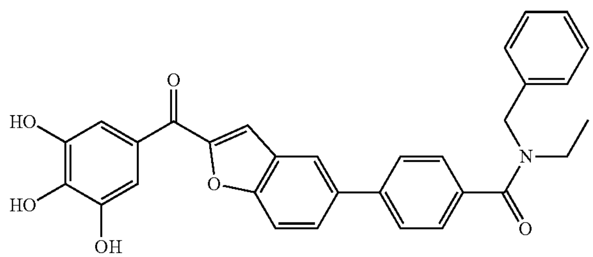 [SMILES: CCN(Cc1ccccc1)C(=O)c1ccc(-c2ccc3oc(C(=O)c4cc(O)c(O)c(O)c4)cc3c2)cc1] | 507.53 | inconclusive (fluorescent molecule) | | 2-4 | 1.4 |
| APY-099 | 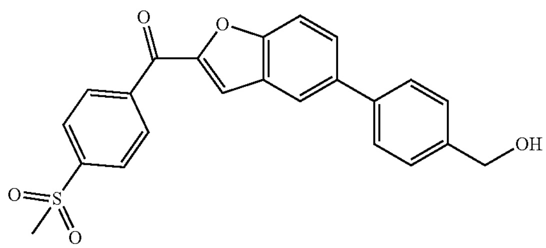 [SMILES: CS(=O)(=O)c1ccc(C(=O)c2cc3cc(-c4ccc(CO)cc4)ccc3o2)cc1] | 406.45 | >1000 | | >128 | 8.2 |
| APY-100 | 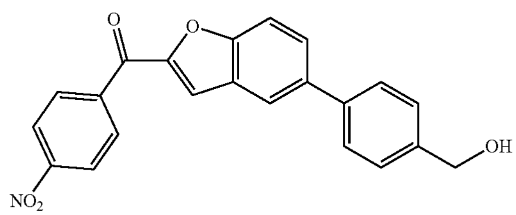 [SMILES: O=C(c1ccc([N+](=O)[O-])cc1)c1cc2cc(-c3ccc(CO)cc3)ccc2o1] | 373.36 | >1000 | | >128 | >128 |
| NED-2014 | 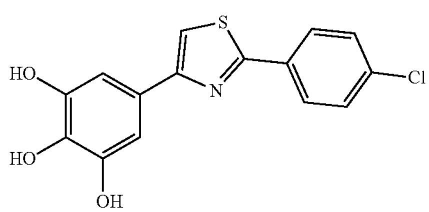 [SMILES: Oc1cc(-c2csc(-c3ccc(Cl)cc3)n2)cc(O)c1O] | 319.76 | 46 ± 2 | not determined | 8 | 0.6 |
| NED-2015 | 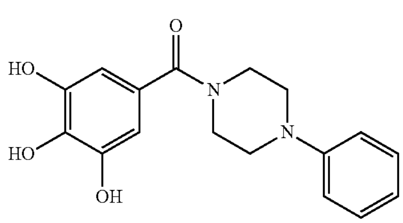 [SMILES: O=C(c1cc(O)c(O)c(O)c1)N1CCN(c2ccccc2)CC1] | 314.34 | >1000 | not determined | 16-32 | 4.4 |
| NED-2016 | 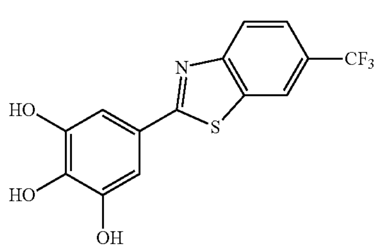 [SMILES: Oc1cc(-c2nc3ccc(C(F)(F)F)cc3s2)cc(O)c1O] | 327.28 | >1000 | not determined | 4 | 1.5 |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| NED-2017 | 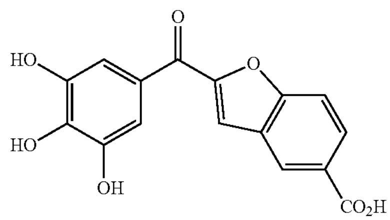 [SMILES: O=C(O)c1ccc2oc(C(=O)c3cc(O)c(O)c(O)c3)cc2c1] | 314.25 | >1000 | not determined | 16-32 | |
| NED-2018 | 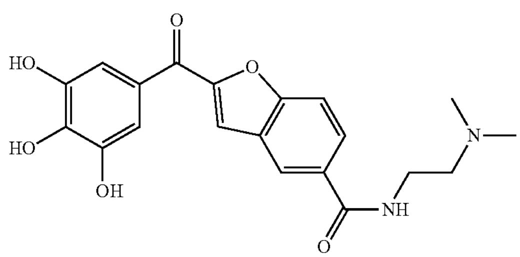 [SMILES: CN(C)CCNC(=O)c1ccc2oc(C(=O)c3cc(O)c(O)c(O)c3)cc2c1] | 384.39 | 9 ± 4 | 0.62 ± 0.03 | 16 | >128 |
| NED-2019 | 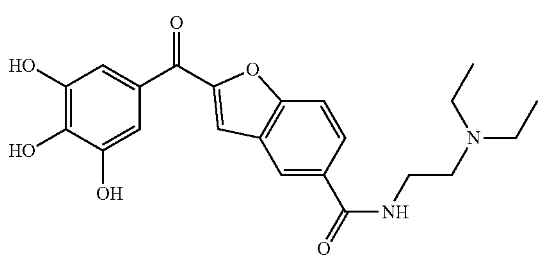 [SMILES: CCN(CC)CCNC(=O)c1ccc2oc(C(=O)c3cc(O)c(O)c(O)c3)cc2c1] | 412.44 | 4.8 ± 0.5 | 0.49 ± 0.03 | 8 | >64 |
| NED-2021 | 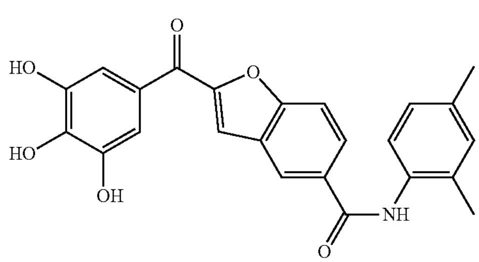 [SMILES: Cc1ccc(NC(=O)c2ccc3oc(C(=O)c4cc(O)c(O)c(O)c4)cc3c2)c(C)c1] | 417.42 | >1000 | not determined | 32-64 | |
| NED-2022 | 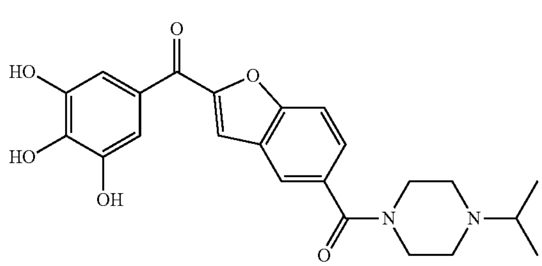 [SMILES: CC(C)N1CCN(C(=O)c2ccc3oc(C(=O)c4cc(O)c(O)c(O)c4)cc3c2)CC1] | 424.45 | 52 ± 12 | not determined | 16 | |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| NED-2023 | 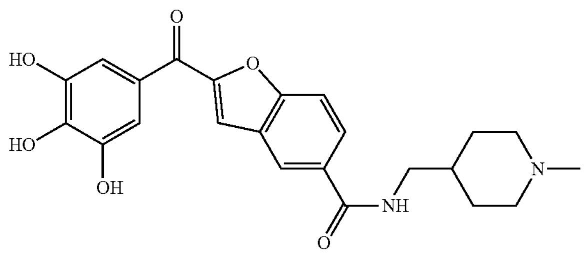 [SMILES: CN1CCC(CNC(=O)c2ccc3oc(C(=O)c4cc(O)c(O)c(O)c4)cc3c2)CC1] | 425.45 | 6 ± 2 | not determined | 16 | 36 |
| NED-2034 | 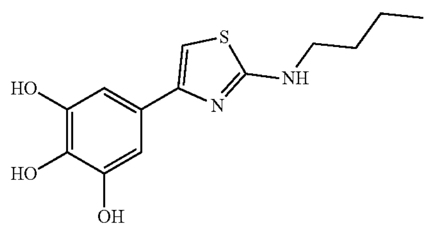 [SMILES: CCCCNc1nc(-c2cc(O)c(O)c(O)c2)cs1] | 280.34 | >1000 | not determined | 8-16 | 22 |
| NED-2035 | 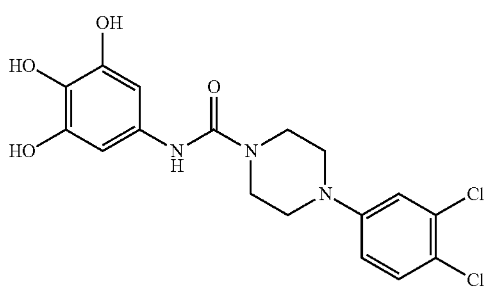 [SMILES: O=C(Nc1cc(O)c(O)c(O)c1)N1CCN(c2ccc(Cl)c(Cl)c2)CC1] | 398.24 | 55 ± 4 | not determined | >128 | 1.6 |
| NED-2036 | 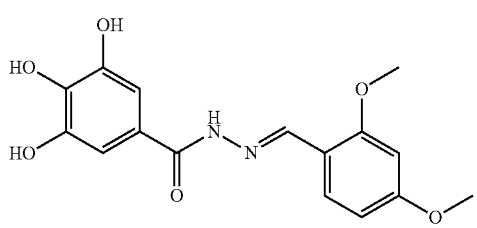 [SMILES: COc1ccc(/C=N/NC(=O)c2cc(O)c(O)c(O)c2)c(OC)c1] | 332.31 | 14 ± 1 | not determined | 8 | 8.2 |
| NED-2037 | 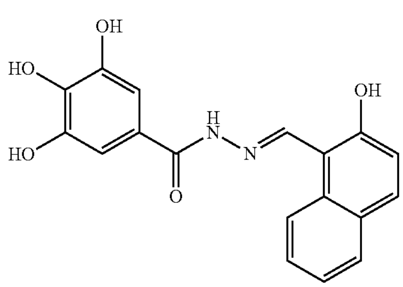 [SMILES: O=C(N/N=C/c1c(O)ccc2ccccc12)c1cc(O)c(O)c(O)c1] | 338.32 | 1.8 ± 0.5 | not determined | 16 | 2.8 |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| NED-2038 | 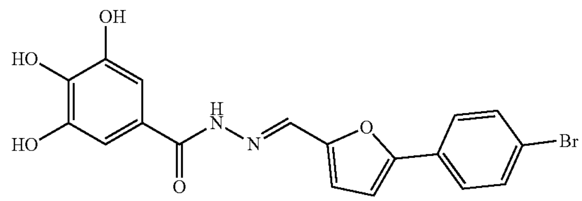 [SMILES: O=C(N/N=C/c1ccc(-c2ccc(Br)cc2)o1)c1cc(O)c(O)c(O)c1] | 417.22 | 2.7 ± 0.5 | 1.7 | 32 | 1.1 |
| NED-2039 | 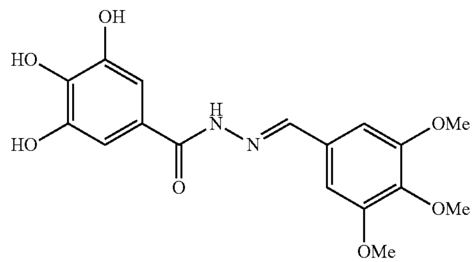 [SMILES: COc1cc(/C=N/NC(=O)c2cc(O)c(O)c(O)c2)cc(OC)c1OC] | 362.34 | 6 ± 1 | not determined | 8 | |
| NED-2040 | 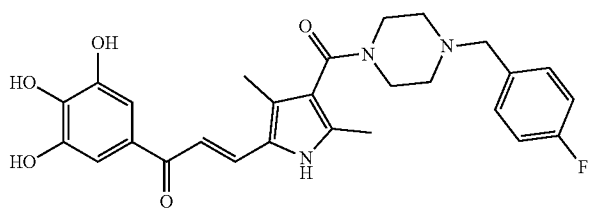 [SMILES: Cc1[nH]c(/C=C/C(=O)c2cc(O)c(O)c(O)c2)c(C)c1C(=O)N1CCN(Cc2ccc(F)cc2)CC1] | 493.53 | >1000 | not determined | 8 | 7.5 |
| NED-2041 | 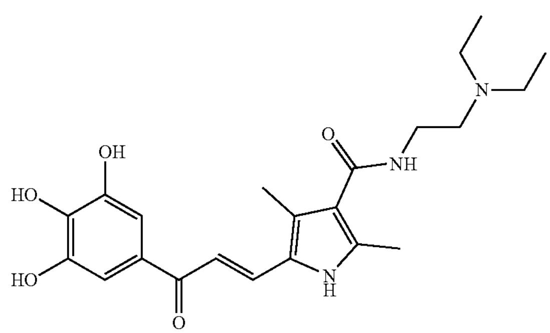 [SMILES: CCN(CC)CCNC(=O)c1c(C)[nH]c(/C=C/C(=O)c2cc(O)c(O)c(O)c2)c1C] | 415.48 | 12 ± 4 | not determined | 32 | |
| NED-2042 | 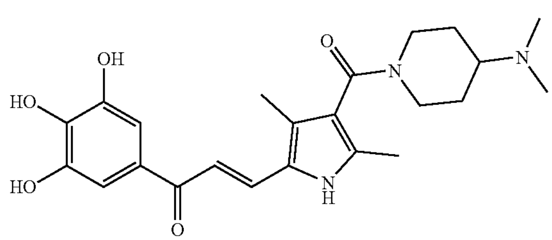 [SMILES: Cc1[nH]c(/C=C/C(=O)c2cc(O)c(O)c(O)c2)c(C)c1C(=O)N1CCC(N(C)C)CC1] | 427.49 | >1000 | not determined | 16 | |
| NED-2047 | 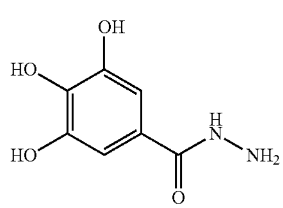 [SMILES: NNC(=O)c1cc(O)c(O)c(O)c1] | 184.15 | 77 ± 3 | not determined | 16-32 | |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| NED-2048 | 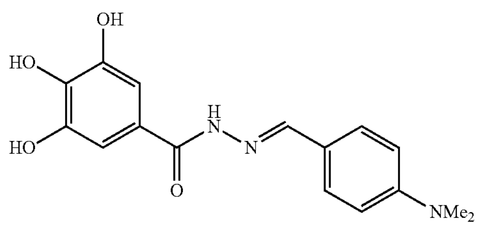 [SMILES: CN(C)c1ccc(/C=N/NC(=O)c2cc(O)c(O)c(O)c2)cc1] | 315.33 | 4 ± 1 | not determined | 4-8 | 9.8 |
| NED-2134 | 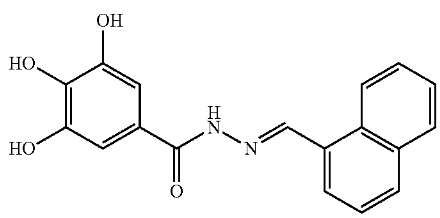 [SMILES: O=C(N/N=C/c1cccc2ccccc12)c1cc(O)c(O)c(O)c1] | 322.32 | 3.3 ± 1 | not determined | 2-4 | 4.2 |
| NED-2135 | 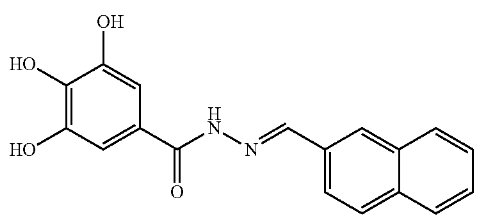 [SMILES: O=C(N/N=C/c1ccc2ccccc2c1)c1cc(O)c(O)c(O)c1] | 332.31 | 0.8 ± 0.2 | not determined | 2 | 2.4 |
| NED-2136 | 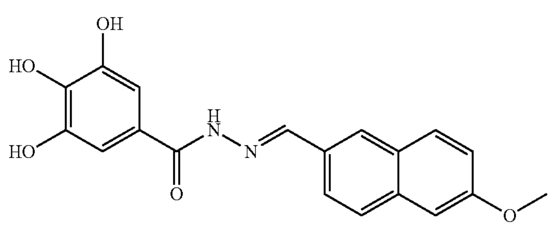 [SMILES: COc1ccc2cc(/C=N/NC(=O)c3cc(O)c(O)c(O)c3)ccc2c1] | 332.31 | 1.35 ± 0.15 | not determined | 2 | 1 |
| NED-2173 | 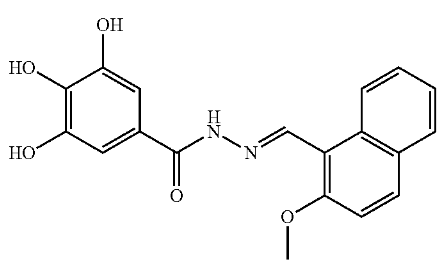 [SMILES: COc1ccc2ccccc2c1/C=N/NC(=O)c1cc(O)c(O)c(O)c1] | 352.35 | 6 ± 1 | not determined | 8 | 8.6 |

TABLE 2-continued

Structure-activity relationships of representative Group II intron inhibitors. In vitro data ($IC_{50}$ and $K_i$ values) are highlighted in bold, and MICs for *C. parapsilosis* are highlighted in italic. Rows showing positive correlation between in vitro data and MICs are highlighted in bold. Rows showing negative correlation between in vitro data and MIC are shown in regular non-bold. A few cases of anticorrelated data were observed, but only for highly hydrophobic molecules expected to participate in pleiotropic interactions in the cell.

| Compound name or CAS number | Structure | MW | $IC_{50}$ ai5γ intron, μM | $K_i$ ai5γ intron, μM | MIC *C. parapsilosis*, μg/ml | $IC_{50}$ HEK-293, μg/ml |
|---|---|---|---|---|---|---|
| NED-2174 | 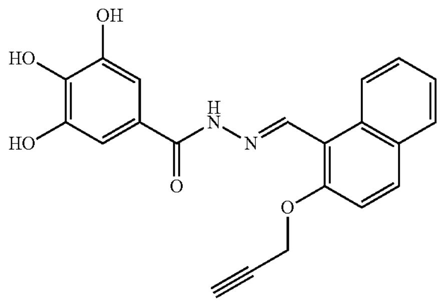 [SMILES: C#CCOc1ccc2ccccc2c1/C=N/NC(=O)c1cc(O)c(O)c(O)c1] | 376.37 | 5 ± 1 | not determined | 4-8 | 2.7 |
| NED-2175 | 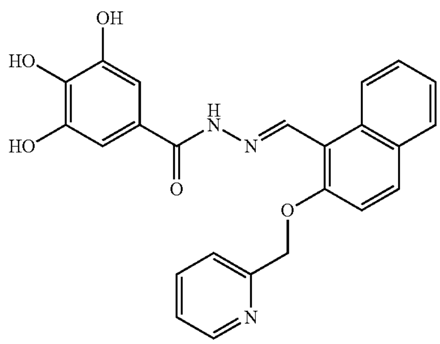 [SMILES: O=C(N/N=C/c1c(OCc2ccccn2)ccc2ccccc12)c1cc(O)c(O)c(O)c1] | 429.43 | 2.3 ± 0.8 | not determined | 4-8 | 14 |
| NED-2251 | 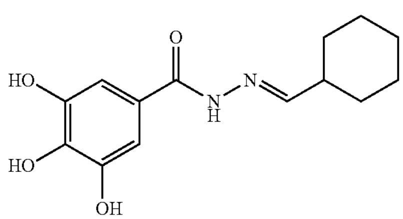 [SMILES: O=C(N/N=C/C1CCCCC1)c1cc(O)c(O)c(O)c1] | 278.31 | not determined | not determined | | 16-32 |

[1]No activity was detected between 5 nM and 100 μM of the compound. Measurements at concentrations above 100 μM were precluded by fluorescence of the compound at high concentrations.

Inhibition of Group II Splicing in *S. cerevisiae* In Vivo.

It was important to determine whether compounds that disrupt splicing of the ai5γ intron in vitro can also inhibit splicing of this intron in vivo. The ai5γ group II intron interrupts a gene encoding the first subunit of the cytochrome oxidase (COX1) in *S. cerevisiae*, and respiratory-deficient petite colonies are therefore formed when ai5γ intron splicing is disrupted. These colonies cannot grow on non-fermentable carbon sources like glycerol, but they exhibit growth on glucose (Perlman, 1990, Methods in enzymology, 181:539-558). To determine whether the inhibitory compounds might induce a respiratory defect, the growth of *S. cerevisiae* was compared in both YPD and YPGE media in the presence of a panel of inhibitors. Growth of *S. cerevisiae* in the presence of inhibitory small molecules is inhibited in glycerol/ethanol medium (YPGE), but not in glucose medium (YPD) (Table 1), which is consistent with the expected respiratory detect.

Figure 26B:
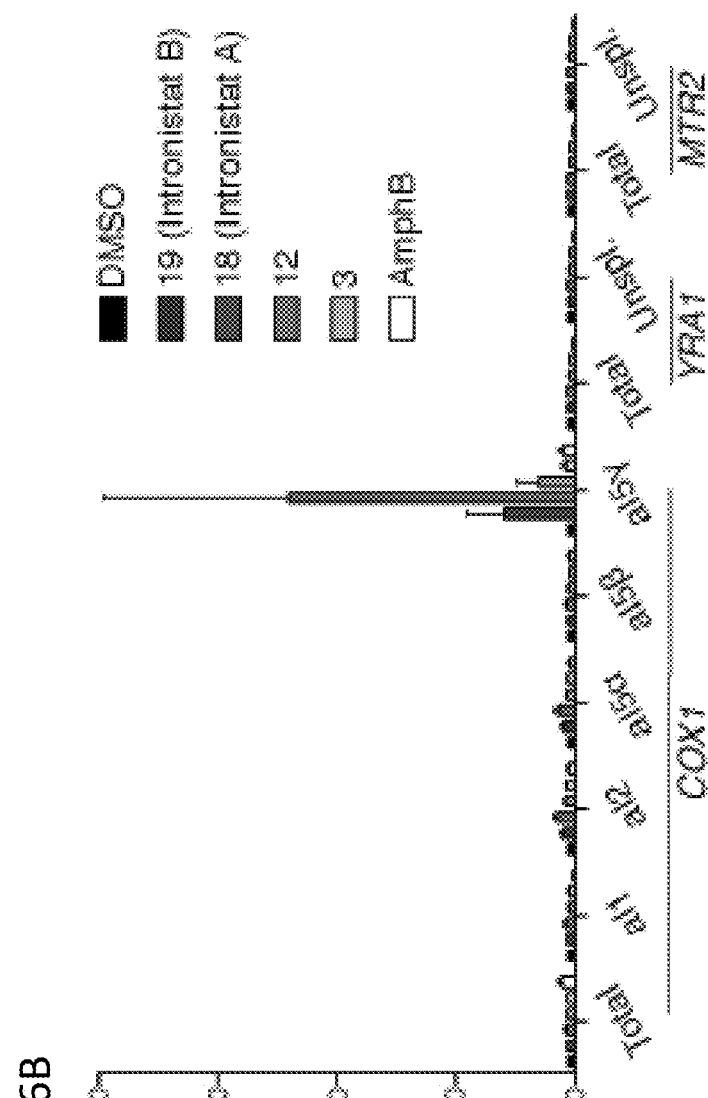
FIGS. 26A-26B depict exemplary experimental results demonstrating that active compounds selectively inhibit group II splicing in vivo.
Figure 26A:
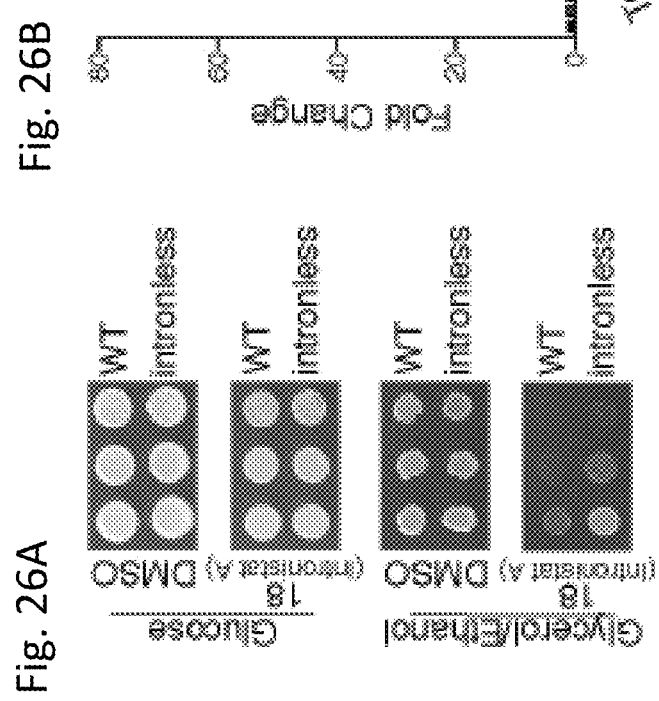
Figures 27A, 27B, 27C:
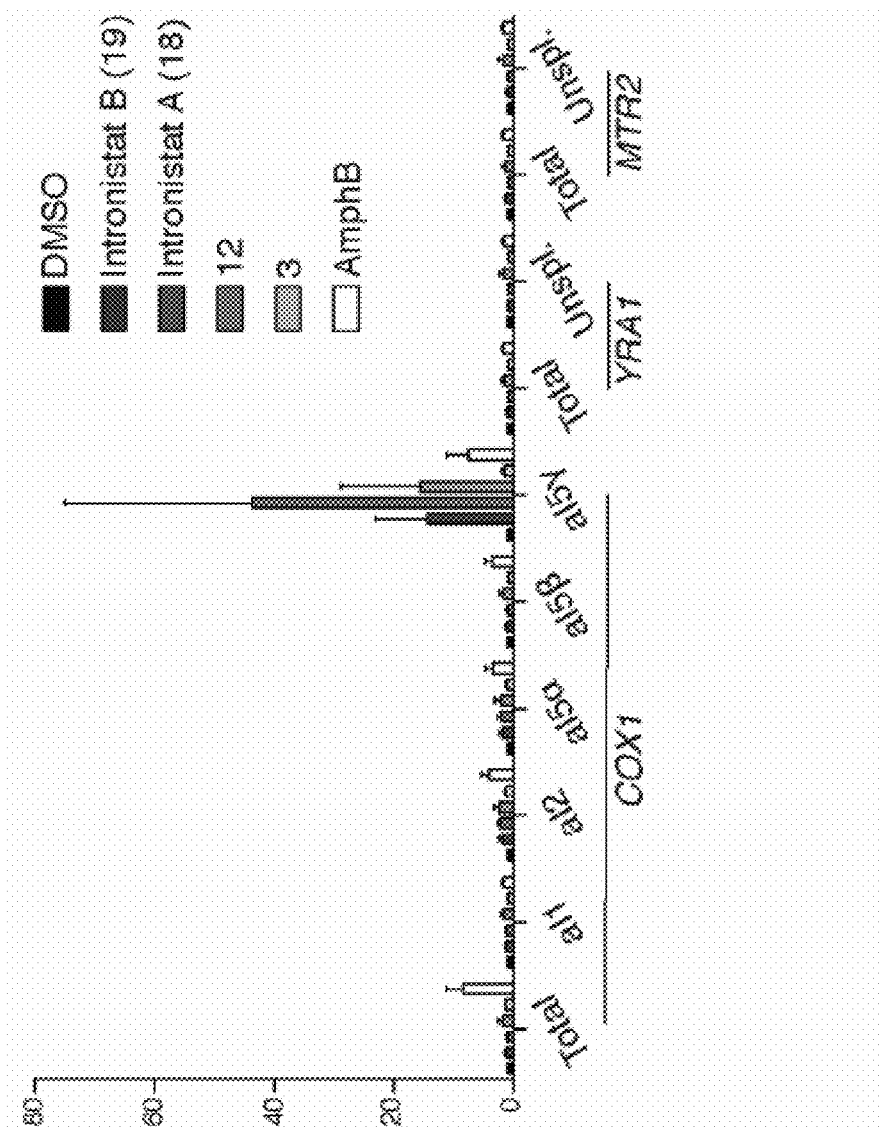
FIGS. 27A-27B depict exemplary experimental results demonstrating that small molecules that are active in vitro cause a severe in vivo splicing defect as evident from significant accumulation of precursor RNA molecules containing 5'-exon-intron junction.
FIG. 27C depicts that *C. parapsilosis* COX1 exhibits a mild splicing defect in the presence of active compound. *C. parapsilosis* were grown in the presence of DMSO vehicle, active compound Intronistat B, or inactive compound APY-001. Relative levels of total and unspliced levels of C.p.COX1 indicated by qRT-PCR quantification of amplicons covering the exon (total) or the intron-exon junction from the group JIB intron. Mean values and s.e.m. from n=3 independent experiments are shown with PGK1 as a standard.

To analyze whether the growth defect Observed in the presence of inhibitor is specifically due to defective splicing of the ai5 g intron, whether the compounds inhibited growth of an "intronless strain", which contains an intact COX1 subunit gene from which the intron has been removed, thereby obviating the requirement for splicing (Perez-Martinez et al., 2003, EMBO J, 22:5951-5961) was examined. A clear difference was observed in growth in between the intronless strain and the wild-type strain in the presence of tritronistat A, revealing that the intronless strain is much more resistant to Intronistat A in YPGE medium (FIGS. 26A-26B, FIG. 27A). This behavior is consistent with specific inhibition of the ai5γ intron in vivo. That said, growth of the intronless strain is somewhat slower in the presence of inhibitor, suggesting that Intronistat A may cause certain off-target effects.

To directly monitor the effect of the most potent compounds on group II intron splicing in vivo, a qRT-PCR. assay was developed for monitoring the splicing of the ai5γ intron in *S. cerevisiae* in the presence of small molecules. Small molecules that are active in vitro cause a severe in vivo splicing defect as evident from significant accumulation of precursor RNA molecules containing 5'-exon-intron junction (FIGS. 26A-26B and FIGS. 27A-27B). Importantly, unspliced COX1 transcripts are targeted for rapid degradation in cells (Dziembowski et al., 2003, J Biol Chem, 278:1603-1611), so the direct observation of substantial precursor accumulation suggests a considerable effect on splicing. Taken together, these results in cells demonstrate that the highest-affinity compounds specifically target the ai5γ intron in vivo, selectively disrupting splicing of the COM gene and thereby reducing yeast growth.

Selectivity of the Group II Intron Inhibitors.

Figures 23A, 23B:
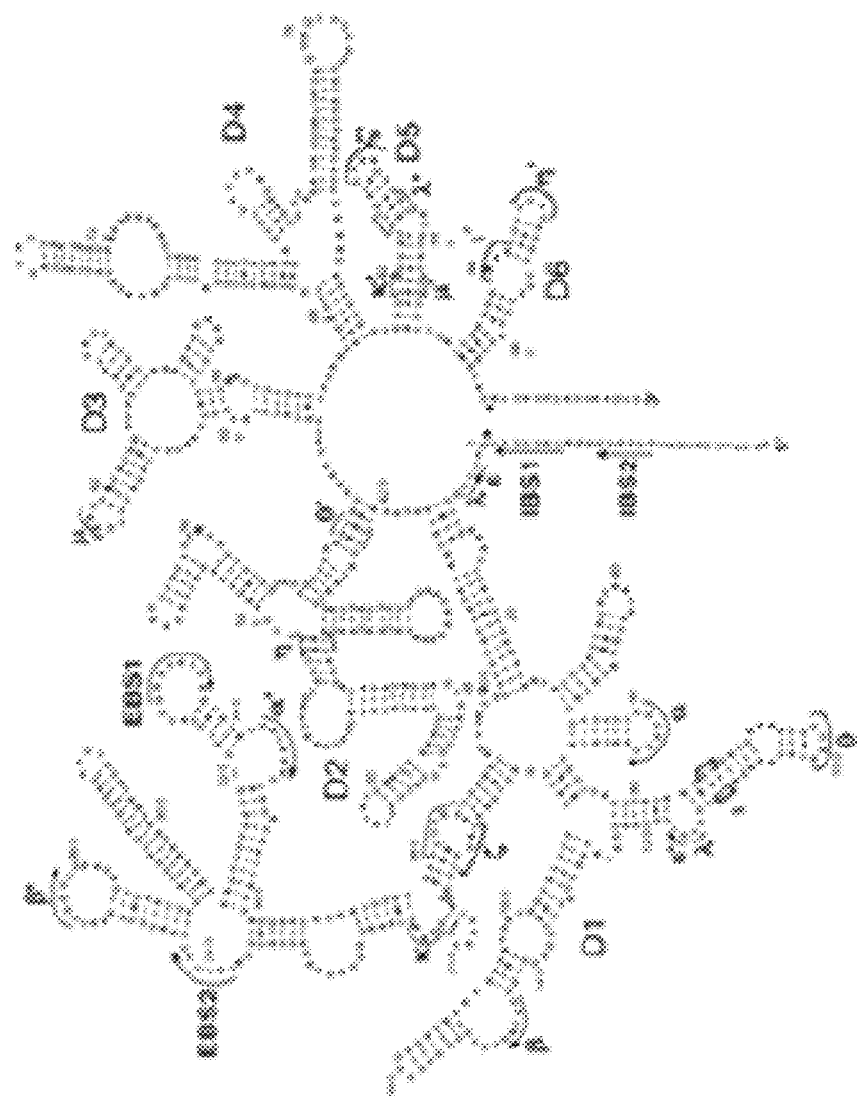
FIGS. 23A-23B depict an exemplary analysis of the secondary structure of a representative yeast intron, in this case the ai5γ group II intron, which is located within the COX1 gene of *Saccharomyces cerevisiae* (S.c.).
Figure 28A:
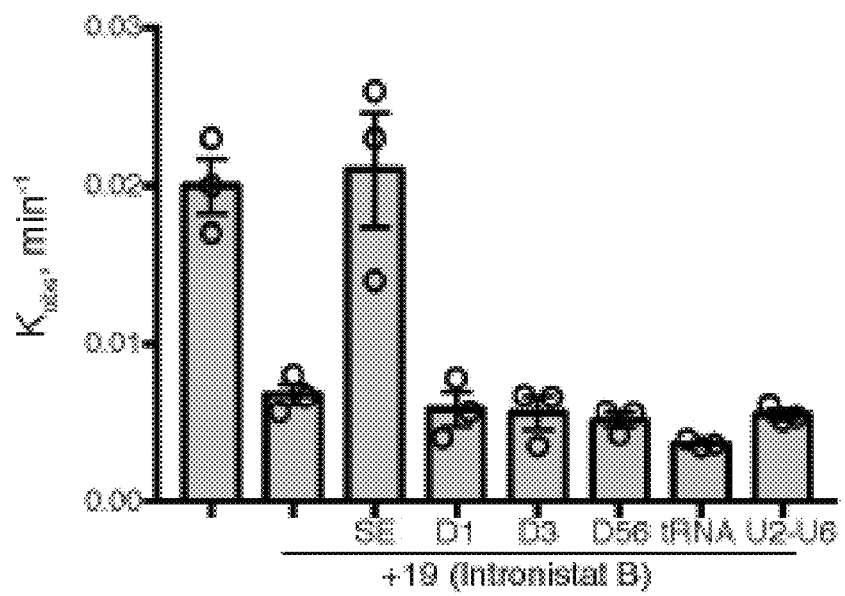
FIGS. 28A-28B depict exemplary experimental results demonstrating that active compounds selectively inhibit group II splicing in vitro.
Figure 28B:
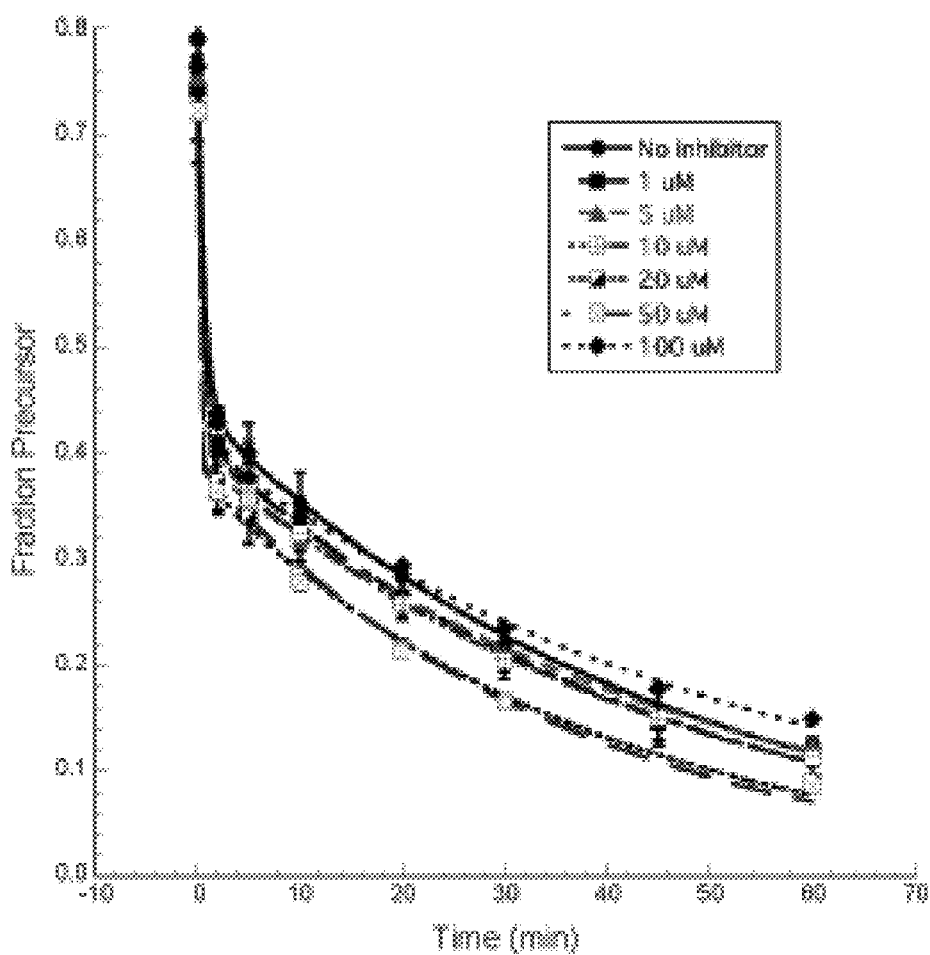

Although the SAR, reversibility analysis and gene specificity of the compounds are consistent with selectivity, it was important to determine whether the compounds can also bind other highly structured RNA molecules, and other RNA splicing systems. In addition, it was questioned whether activity requires the fully-folded group II intron RNA tertiary structure, or if individual intron domains can bind the inhibitors with high affinity. To this end, the inhibitory activity of one of the most promising compounds, Intronistat B, was monitored in the presence of a large excess of various RNAs, including separate ai5γ intron domains D1, D3, D56, the U2-U6 snRNA stemloop (analogous to group II intron D5), and yeast tRNA$_{Phe}$ (FIGS. 23A-23B). The latter was an important control because tRNA molecules possess many archetypal elements of RNA tertiary structure, such as kissing loops involving canonical and non-canonical base pairs, coaxially stacked helices, base triples and U-turn motifs, which make them commonly used specificity controls for RNA targeting (Luedtke et al., 2003, Biochemistry, 42:11391-11403). However, none of these RNAs, presented in a 1000-fold excess relative to intron RNA (2 nM), affect the inhibitory activity of Intronistat B (FIG. 28A). The only RNA that competed with radiolabeled SE group II intron RNA for binding of Intronistat B was the same unlabeled group IIB intron RNA added in excess (FIG. 28A). To evaluate inhibition of the other two known RNA splicing systems (group I and spliceosome) splicing of the Azoarcus pre-tRNA (Ile) group I intron was monitored (Tanner et al., 1996, RNA 2:74-83) in the presence of Intronistat B. Splicing of the Azoarcus intron is unaffected, even at 100 µM Intronistat B (FIG. 28B). In addition, qRT-PCR was used to monitor inhibition of group I intron and spliceosomal splicing in S. cerevisiae in vivo. Consistent with previous results, the inhibitors only affect splicing of the yeast ai5γ group II intron (FIG. 26B). Spliceosomal processing, group I intron splicing and even splicing of group II introns from subclasses that differ from subclass IIB are unaffected by the small molecule inhibitors. These results are consistent with the in vitro results and suggest that the inhibitors bind selectively to group IIB introns. The data also indicate that the inhibitors bind tertiary structural elements formed by the entire intron and not individual intronic domains.

Small Molecule Growth Inhibition of C. parapsilosis

Figure 29A:
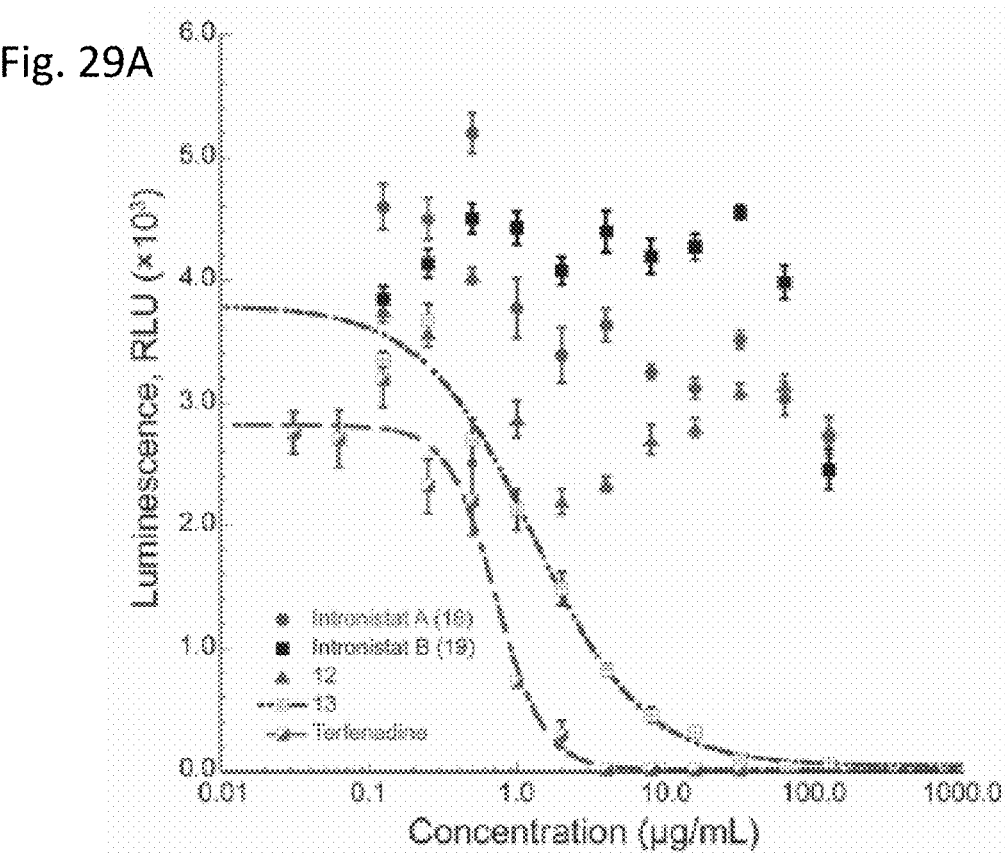
FIGS. 29A-29B exemplary experimental results demonstrating that active compound Intronistat B demonstrates minimal cytotoxicity.
Figure 29B:
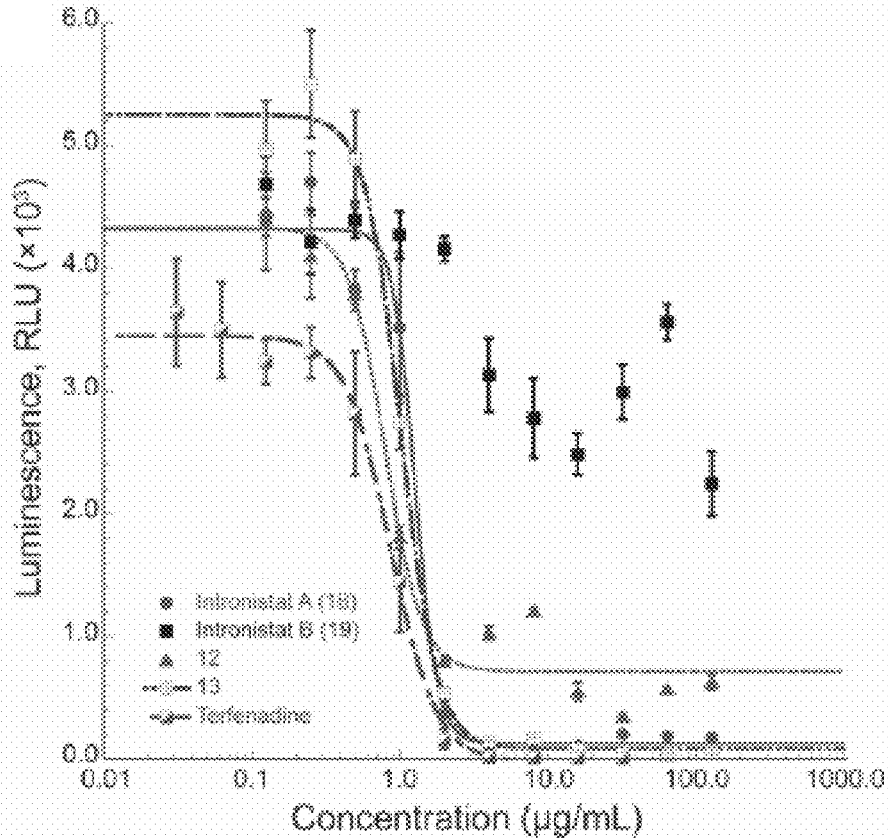

The yeast pathogen C. parapsilosis contains a single group IIB intron in its COX1 gene (Li et al., 2011, RNA, 17:1321-1335). The active site of this intron (D5) is almost identical to that of the ai5 g intron (FIG. 1B), suggesting that compounds that inhibit the S.c. ai5γ intron may also inhibit splicing by the group II intron in C. parapsilosis. To evaluate efficacy of the compounds against this pathogen, the minimum inhibitory concentrations (MIC values) required for growth inhibition of C. parapsilosis were evaluated. The high affinity ai5γ intron inhibitors significantly reduce the growth of C. parapsilosis (FIG. 24, Table 2). Correlations between $IC_{50}$, $K_i$ and MIC values suggest that these compounds employ the same mechanism of action both in vitro and in vivo (FIG. 24, Table 2). While many of the highest-affinity compounds displayed strong MIC values, compounds Intronistat A ($K_i$=2.1±0.2 µM) and Intronistat B ($K_i$=0.36±0.02 µM) were particularly notable because their MIC values (2-4 µg/ml) are comparable to that of Amphotericin B, which is still commonly used for acute C. parapsilosis infection (Moen et al., 2009, Drugs, 69:361-92) (MIC is 0.5-1 µg/ml) (FIG. 24, Table 2). Given their potency and antifungal effects, compound APY-101 has been named Intronistat A, and compound NED-2020 Intronistat B. To directly monitor behavior of the compounds in vivo, qRT-PCR was used to quantify levels of splicing for the C. parapsilosis COX1 precursor mRNA (which contains the group IIB intron) in the presence of Intronistat B and inactive APY-001. A moderate splicing defect caused by Intronistat B was identified as indicated by increased levels of unspliced C.p.COX1 relative to total, and this effect was not observed in the presence of inactive APY-001 (FIG. 27C). To determine whether inhibition is specific to yeast, the toxicity of the most potent compounds in human cells was evaluated, determining the $IC_{50}$ for inhibition of HEK-293T cells (FIG. 24, FIGS. 29A-29B, Table 2). While some of the compounds are broadly toxic to all eukaryotic cells tested, the most potent compounds, including Intronistat A and Intronistat B, did not show toxicity in human cells after 24 hours incubation (FIG. 24, FIG. 29A, Table 2). Even after 72 hours incubation Intronistat B had only mild effects on cell viability (FIG. 29B), suggesting that this compound specifically targets yeast strains that contain group II introns in an essential gene and that it lacks cross-reactivity with the nuclear spliceosome, or other targets, in yeast and humans.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound selected from the group consisting of:

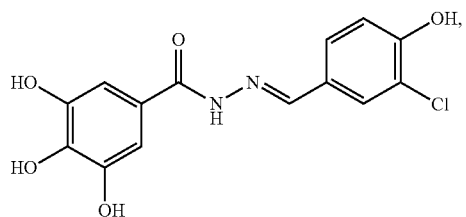

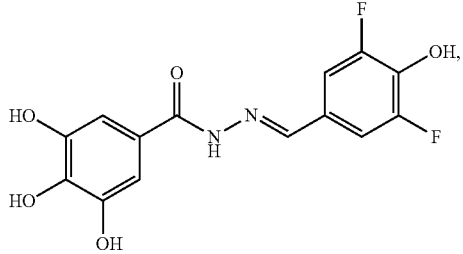

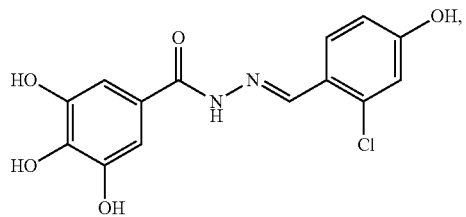

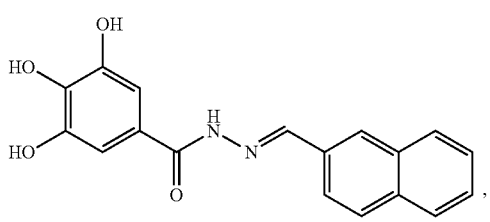

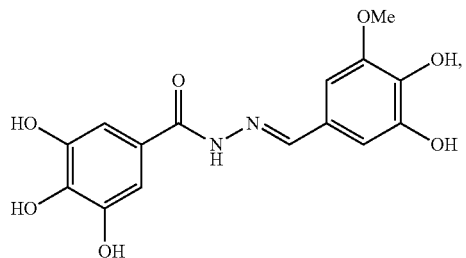

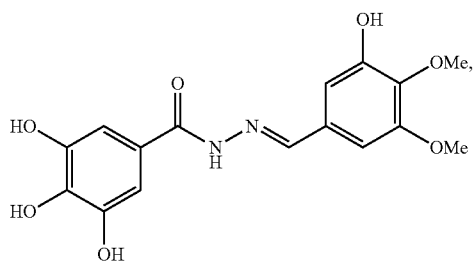

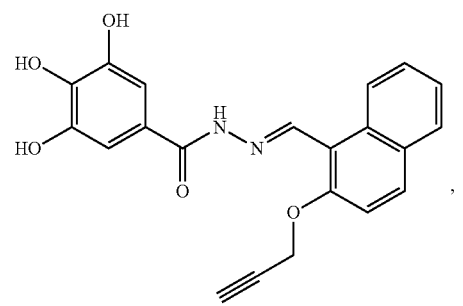

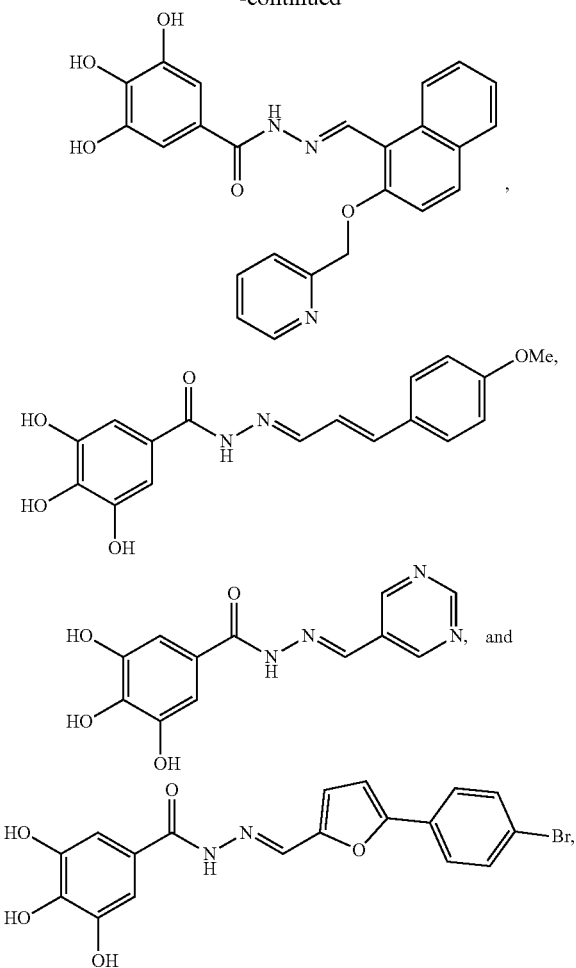

or a salt thereof.

2. A method of reducing, or preventing growth of an organism harboring an active group II intron, wherein the organism is selected from the group consisting of a bacteria, a yeast, a fungus, a protist, a parasite, and a plant, the method comprising contacting the organism with an effective amount of an inhibitor of group II intron splicing selected from the group consisting of:

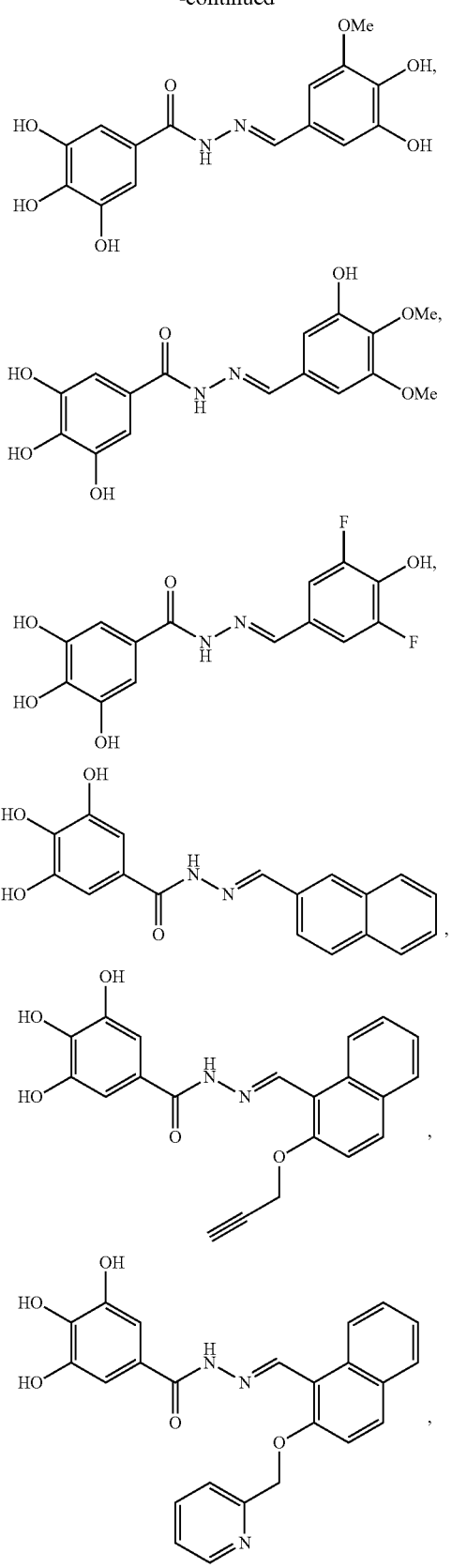

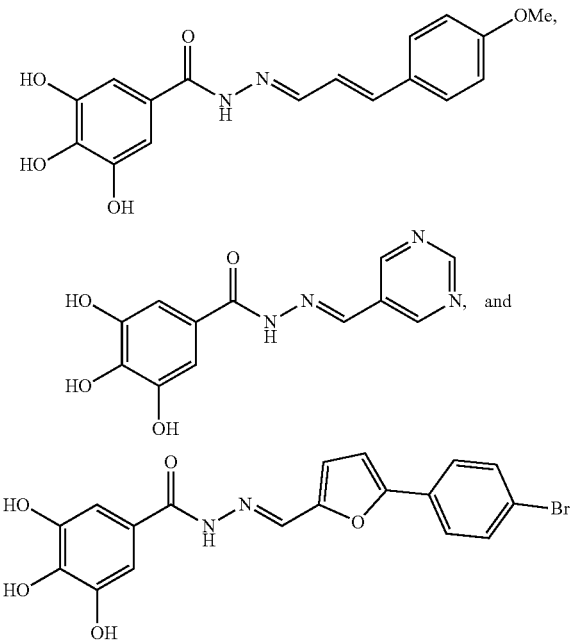

or a salt thereof.

3. A method of treating or ameliorating a disease associated with an organism harboring an active group II intron in a subject, wherein the disease or disorder is selected from the group consisting of a bacterial infection, a yeast infection, a fungal infection, and a parasite infection, the method comprising administering to the subject an effective amount of an inhibitor of group II intron splicing selected from the group consisting of:

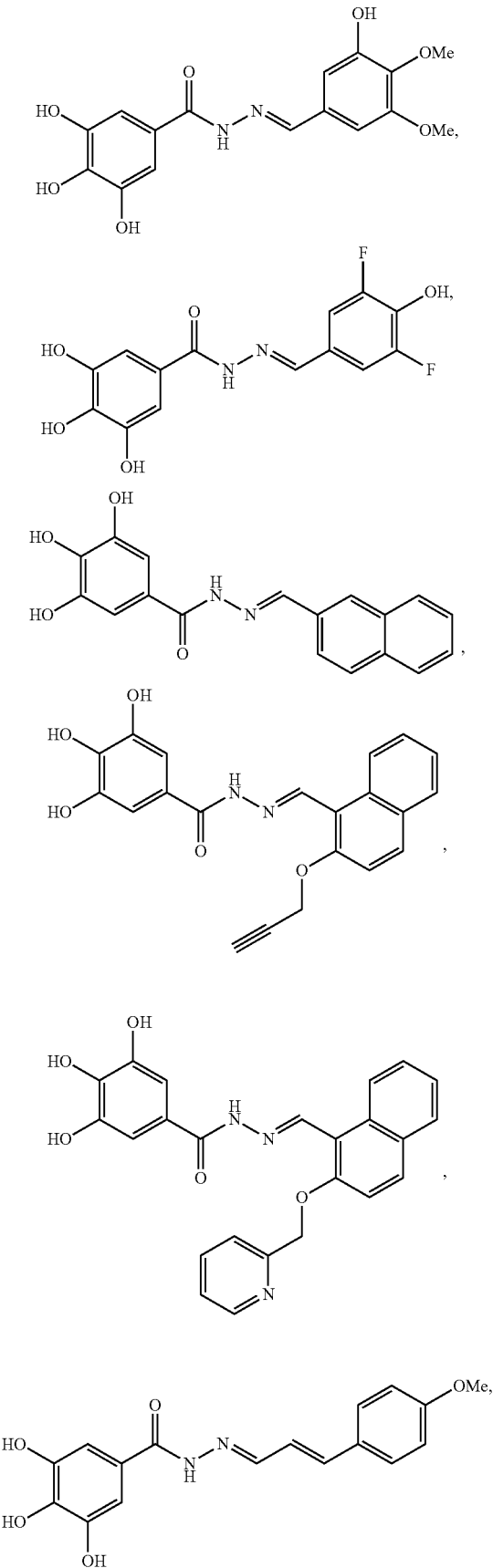

-continued
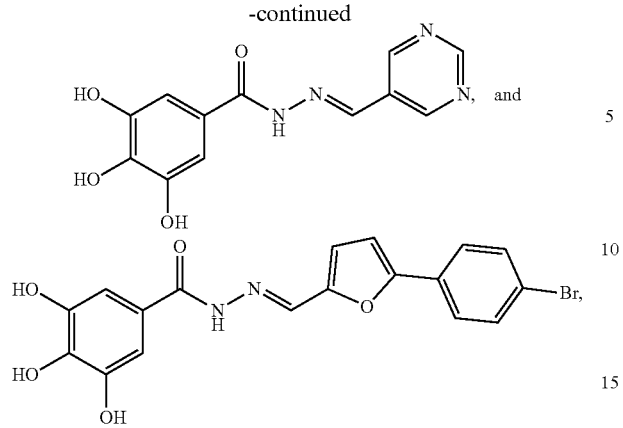
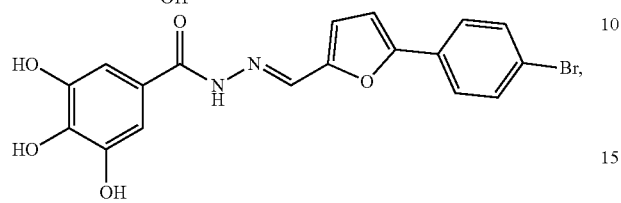
or a salt thereof.
4. The method of claim 3, wherein the subject is a mammal.
5. The method of claim 4, wherein the mammal is a human.
* * * * *